United States Patent
Welker et al.

(10) Patent No.: US 9,359,470 B2
(45) Date of Patent: Jun. 7, 2016

(54) DITHIENOBENZOFURAN POLYMERS AND SMALL MOLECULES FOR ELECTRONIC APPLICATION

(71) Applicant: BASF SE, Ludwigshafen (DE)

(72) Inventors: Matthias Welker, St. Louis (FR); Mathieu G. R. Turbiez, Rixheim (FR); Natalia Chebotareva, Hagenthal le Bas (FR); Hans Juerg Kirner, Basel (CH); Thomas Schaefer, Liestal (CH)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/414,527

(22) PCT Filed: Jul. 19, 2013

(86) PCT No.: PCT/EP2013/065313
§ 371 (c)(1),
(2) Date: Jan. 13, 2015

(87) PCT Pub. No.: WO2014/016219
PCT Pub. Date: Jan. 30, 2014

(65) Prior Publication Data
US 2015/0132887 A1    May 14, 2015

Related U.S. Application Data

(60) Provisional application No. 61/674,399, filed on Jul. 23, 2012.

(30) Foreign Application Priority Data

Jul. 23, 2012 (EP) .................................. 12177408

(51) Int. Cl.
*C08G 75/00* (2006.01)
*C08G 61/12* (2006.01)
*C07D 495/14* (2006.01)
*C07D 519/00* (2006.01)
*H01B 1/12* (2006.01)
*H01L 51/00* (2006.01)
(Continued)

(52) U.S. Cl.
CPC ............ *C08G 61/126* (2013.01); *C07D 495/14* (2013.01); *C07D 519/00* (2013.01); *C07F 5/04* (2013.01); *C08G 61/125* (2013.01); *C09B 57/00* (2013.01); *C09B 57/004* (2013.01); *C09B 69/109* (2013.01); *H01B 1/124* (2013.01); *H01L 51/0002* (2013.01); *H01L 51/0035* (2013.01); *H01L 51/0036* (2013.01); *H01L 51/0043* (2013.01); *H01L 51/0558* (2013.01); *H01L 51/4253* (2013.01); *C08G 2261/12* (2013.01); *C08G 2261/124* (2013.01);
(Continued)

(58) Field of Classification Search
CPC .. C08G 61/126; C08G 61/125; C07D 519/00; C07D 495/14; H01L 51/0043; H01L 51/46
USPC .......................................... 528/377, 373, 380
See application file for complete search history.

(56) References Cited

U.S. PATENT DOCUMENTS

| | | | |
|---|---|---|---|
| 6,451,459 | B1 | 9/2002 | Tieke et al. |
| 6,690,029 | B1 | 2/2004 | Anthony et al. |

(Continued)

FOREIGN PATENT DOCUMENTS

| | | |
|---|---|---|
| EP | 1 179 840 A1 | 2/2002 |
| EP | 2 006 291 A1 | 12/2008 |

(Continued)

OTHER PUBLICATIONS

International Search Report issued Nov. 26, 2013 in PCT/EP2013/065313.
(Continued)

*Primary Examiner* — Shane Fang
(74) *Attorney, Agent, or Firm* — Oblon, McClelland, Maier & Neustadt, L.L.P.

(57) ABSTRACT

The present invention relates to polymers comprising a repeating unit of the formula (I), and compounds of formula (VIII), or (IX), wherein Y, $Y^{15}$, $Y^{16}$ and $Y^{17}$ are independently of each other a group of formula (I), and their use as organic semiconductor in organic electronic devices, especially in organic photovoltaics and photodiodes, or in a device containing a diode and/or an organic field effect transistor. The polymers and compounds according to the invention can have excellent solubility in organic solvents and excellent film-forming properties. In addition, high efficiency of energy conversion, excellent field-effect mobility, good on/off current ratios and/or excellent stability can be observed, when the polymers and compounds according to the invention are used in organic field effect transistors, organic photovoltaics (solar cells) and photodiodes.

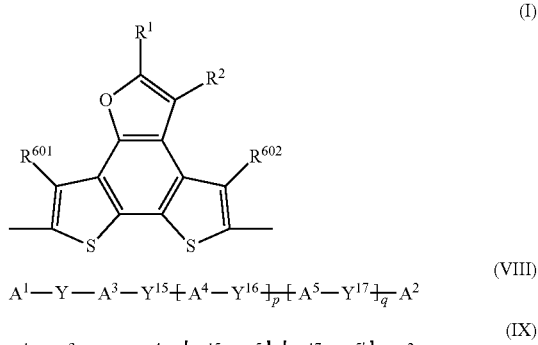

14 Claims, No Drawings

(51) Int. Cl.
*H01L 51/05* (2006.01)
*H01L 51/42* (2006.01)
*C09B 57/00* (2006.01)
*C09B 69/10* (2006.01)
*C07F 5/04* (2006.01)

(52) U.S. Cl.
CPC . *C08G 2261/148* (2013.01); *C08G 2261/3242* (2013.01); *C08G 2261/3243* (2013.01); *C08G 2261/3247* (2013.01); *C08G 2261/411* (2013.01); *C08G 2261/51* (2013.01); *C08G 2261/91* (2013.01); *C08G 2261/92* (2013.01); *H01L 51/05* (2013.01); *H01L 51/42* (2013.01); *Y02E 10/549* (2013.01)

(56) References Cited

U.S. PATENT DOCUMENTS

| | | |
|---|---|---|
| 2003/0021913 A1 | 1/2003 | O'Neill et al. |
| 2006/0013549 A1 | 1/2006 | Shtein et al. |
| 2007/0079867 A1 | 4/2007 | Chittibabu et al. |
| 2010/0326225 A1 | 12/2010 | Fischbein |
| 2011/0006287 A1 | 1/2011 | You et al. |
| 2011/0028644 A1 | 2/2011 | Brown et al. |
| 2011/0240973 A1* | 10/2011 | Dueggeli ............. B82Y 10/00 257/40 |
| 2012/0097935 A1 | 4/2012 | Kirner et al. |
| 2015/0029638 A1 | 1/2015 | Hans Juerg Kirner et al. |

FOREIGN PATENT DOCUMENTS

| | | |
|---|---|---|
| EP | 2 034 537 A2 | 3/2009 |
| EP | 2 075 274 A1 | 7/2009 |
| WO | WO 03/052841 A1 | 6/2003 |
| WO | WO 2004/101581 A2 | 11/2004 |
| WO | WO 2004/112161 A2 | 12/2004 |
| WO | WO 2005/049695 A1 | 6/2005 |
| WO | WO 2007/082584 A1 | 7/2007 |
| WO | WO 2008/000664 A1 | 1/2008 |
| WO | WO 2008/001123 A1 | 1/2008 |
| WO | WO 2008/107089 A1 | 9/2008 |
| WO | WO 2009/047104 A2 | 4/2009 |
| WO | WO 2009/115413 A2 | 9/2009 |
| WO | WO 2010/049321 A1 | 5/2010 |
| WO | WO 2010/049323 A1 | 5/2010 |
| WO | WO 2010/108873 A1 | 9/2010 |
| WO | WO 2010/115767 A1 | 10/2010 |
| WO | WO 2010/136352 A1 | 12/2010 |
| WO | WO 2010/136353 A1 | 12/2010 |
| WO | WO 2010/136401 A2 | 12/2010 |
| WO | WO 2011/002927 A2 | 1/2011 |
| WO | WO 2011/025454 A1 | 3/2011 |
| WO | WO 2011/144566 A2 | 11/2011 |
| WO | WO 2012/175530 A1 | 12/2012 |
| WO | WO 2013/149897 A1 | 10/2013 |

OTHER PUBLICATIONS

K.G. Lewis et al., "Aspects of the Formation and Use of Stenhouse Salts and Related Compounds", Tetrahedron, vol. 33, No. 5, XP-055045617, Jan. 1, 1977, pp. 463-475.

Stoichko D. Dimitrov et al., "Efficient Charge Photogeneration by the Dissociation of $PC_{70}BM$ Excitons in Polymer/Fullerene Solar Cells", J. Phys. Chem., Lett. 3, 2012, pp. 140-144.

B.C. Schroeder et al., "Benzotrithiophene Co-polymers with High Charge Carrier Mobilities in Field-Effect Transistors", Chemistry of Materials, 23, 2011, pp. 4025-4031.

U.S. Appl. No. 14/385,696, filed Sep. 16, 2014, Welker, et al.

* cited by examiner

DITHIENOBENZOFURAN POLYMERS AND SMALL MOLECULES FOR ELECTRONIC APPLICATION

The present invention relates to polymers comprising a repeating unit of the formula (I) and compounds of formula (VIII), or (IX), wherein Y, $Y^{15}$, $Y^{16}$ and $Y^{17}$ are independently of each other a group of formula (I), and their use as organic semiconductor in organic electronic devices, especially in organic photovoltaics (solar cells) and photodiodes, or in a device containing a diode and/or an organic field effect transistor. The polymers and compounds according to the invention can have excellent solubility in organic solvents and excellent film-forming properties. In addition, high efficiency of energy conversion, excellent field-effect mobility, good on/off current ratios and/or excellent stability can be observed, when the polymers and compounds according to the invention are used in organic field effect transistors, organic photovoltaics (solar cells) and photodiodes.

WO2010136401 relates to polycyclic dithiophenes of the following formula

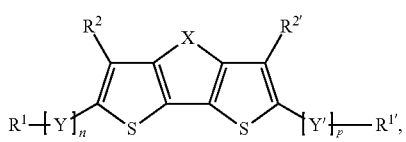

wherein $R^1$ and $R^{1'}$ independently of each other are H or a substituent, halogen or $SiR^6R^4R^5$;

$R^2$ and $R^{2'}$ may be the same or different and are selected from $C_1$-$C_{25}$alkyl, $C_3$-$C_{12}$cycloalkyl, $C_2$-$C_{25}$alkenyl, $C_2$-$C_{25}$alkynyl, $C_4$-$C_{25}$aryl, $C_5$-$C_{25}$alkylaryl or $C_5$-$C_{25}$aralkyl, each of which is unsubstituted or substituted, and if $R^3$ and $R^{3'}$ within the definition of X together complete a ring structure, or X is a bridging group conforming to one of the formulae

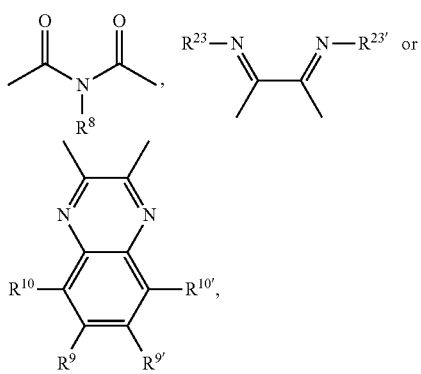

$R^2$ and/or $R^{2'}$ may also be halogen or hydrogen;

X is a divalent linking group selected from

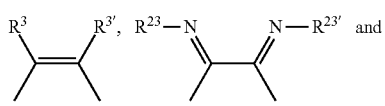

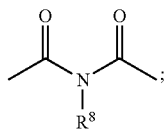

Y and Y' independently are selected from

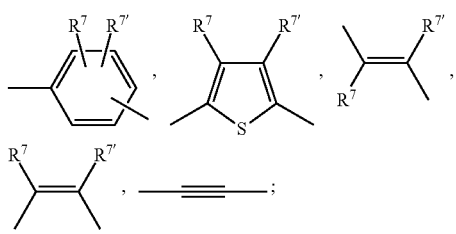

n and p independently range from 0 to 6;

$R^3$ and $R^{3'}$ independently are hydrogen or a substituent, or are amino, or together, with the carbon atoms they are attached to, complete a 5- or 6-membered unsubstituted or substituted hydrocarbon ring, or a 5-membered unsubstituted or substituted heterocyclic ring comprising at least one hetero atom selected from N, O, or S; as well as oligomers, polymers or copolymers comprising at least 2 structural units of the formula

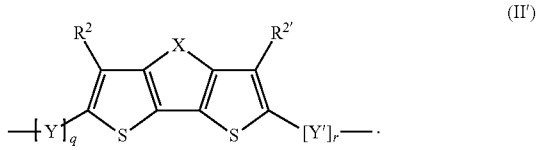

The substances described in WO2010136401 are used in organic field effect transistors, organic photovoltaics (solar cells) and photodiodes.

WO2011002927 relates to is directed to a (copolymer) composition comprising at least one donor acceptor copolymer, said at least one copolymer comprising at least one first bithiophene repeat unit (donor) represented by formula

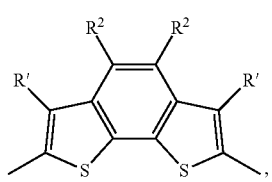

wherein $R_1$, $R_2$ and R' are solubilizing groups or hydrogen. According to claim 8 of WO2011002927 $R^1$ and $R^2$ may form a heterocyclic ring.

In addition, polymers comprising a bithiophene repeating unit are described in EP2006291A1, US20110006287 and WO2011025454.

PCT/EP2013/056463 relates to organic electronic devices comprising polymers or small molecules comprising at least one (repeating) unit of the formulas (I) and (II)

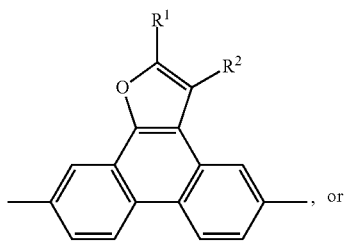, or

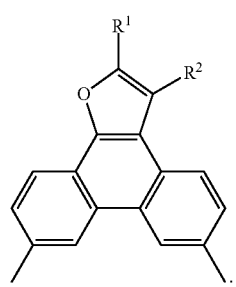.

Schroeder B. C. et al., Chem. Mater., 23 (2011) 4025-4031 describe the use of polymers comprising monomers units of formula M1 and M2 in manic field effect transistors:

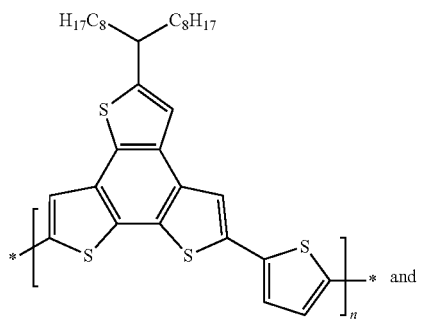 M1

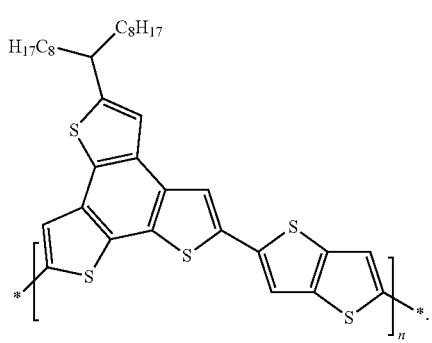 M2

James R. Durrant et al., J. Phys. Chem. Lett. 2012, 3, 140-144 report on the contribution of photoinduced hole transfer to the device photocurrent for an OPV device with an active layer comprising a blend film of the small bandgap polymer

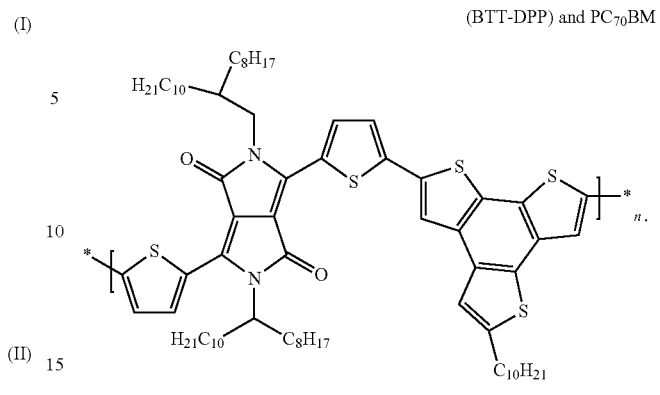

(BTT-DPP) and PC$_{70}$BM

It is one object of the present invention to provide polymers, which show high efficiency of energy conversion, excellent field-effect mobility, good on/off current ratios and/or excellent stability, when used in organic field effect transistors, organic photovoltaics (solar cells) and photodiodes.

Said object has been solved by polymers, comprising a repeating unit of the formula

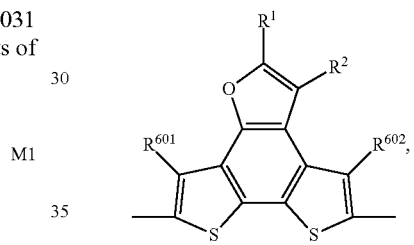 (I)

wherein $R^1$ and $R^2$ are independently of each other H, F, $C_1$-$C_{18}$alkyl, $C_1$-$C_{18}$alkyl which is substituted by E' and/or interrupted by D', $C_6$-$C_{24}$aryl, $C_6$-$C_{24}$aryl which is substituted by G', $C_2$-$C_{20}$heteroaryl, $C_2$-$C_{20}$heteroaryl which is substituted by G', or $R^1$ and $R^2$ form together a group

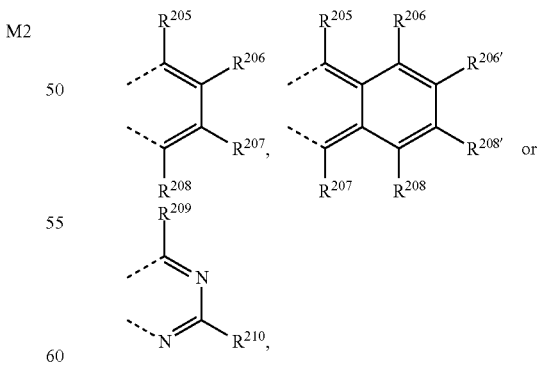

wherein $R^{205}$, $R^{206}$, $R^{206'}$, $R^{207}$, $R^{208}$, $R^{208'}$, $R^{209}$ and $R^{210}$ are independently of each other H, $C_1$-$C_{18}$alkyl, $C_1$-$C_{18}$alkyl which is substituted by E' and/or interrupted by D', $C_1$-$C_{18}$alkoxy, or $C_1$-$C_{18}$alkoxy which is substituted by E' and/or interrupted by D', $C_1$-$C_{18}$fluoroalkyl, $C_6$-$C_{24}$aryl, $C_6$-$C_{24}$aryl which is substituted by G', $C_2$-$C_{20}$heteroaryl, $C_2$-$C_{20}$heteroaryl which is substituted by G', $C_2$-$C_{18}$alkenyl, $C_2$-$C_{18}$alkynyl, $C_7$-$C_{25}$aralkyl, $C_7$-$C_{25}$aralkyl which is substituted by G'; CN, or —CO—$R^{28}$, $R^{601}$ and $R^{602}$ are independently of each other H, halogen, $C_1$-$C_{25}$alkyl, $C_3$-$C_{12}$cycloalkyl, $C_2$-$C_{25}$alkenyl, $C_2$-$C_{25}$alkynyl, $C_6$-$C_{24}$aryl, $C_6$-$C_{24}$aryl which is substituted by G', $C_7$-$C_{25}$aralkyl, or $C_7$-$C_{25}$aralkyl which is substituted by G';

D' is —CO—, —COO—, —S—, —SO—, —$SO_2$—, —O—, —$NR^{65}$—, —$SiR^{70}R^{71}$—, —$POR^{72}$—, —$CR^{63}$=$CR^{64}$—, or —C≡C—, and E' is —$OR^{69}$, —$SR^{69}$, —$NR^{65}R^{66}$, —$COR^{68}$, —$COOR^{67}$, —$CONR^{65}R^{66}$, —CN, $CF_3$, or halogen, G' is E', $C_1$-$C_{18}$alkyl, or $C_1$-$C_{18}$alkyl which is interrupted by —O—, $R^{28}$ is H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{63}$ and $R^{64}$ are independently of each other $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—;

$R^{65}$ and $R^{66}$ are independently of each other $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—; or $R^{65}$ and $R^{66}$ together form a five or six membered ring, $R^{67}$ is $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{68}$ is H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{69}$ is $C_6$-$C_{18}$aryl; $C_6$-$C_{18}$aryl, which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{70}$ and $R^{71}$ are independently of each other $C_1$-$C_{18}$alkyl, $C_6$-$C_{18}$aryl, or $C_6$-$C_{18}$aryl, which is substituted by $C_1$-$C_{18}$alkyl, and $R^{72}$ is $C_1$-$C_{18}$alkyl, $C_6$-$C_{18}$aryl, or $C_6$-$C_{18}$aryl, which is substituted by $C_1$-$C_{18}$alkyl.

Advantageously, the polymer of the present invention, or an organic semiconductor material, layer or component, comprising the polymer of the present invention, can be used in organic light emitting diodes (PLEDs, OLEDs), organic photovoltaics (solar cells) and photodiodes, or in an organic field effect transistor (OFET).

The polymers of this invention preferably have a weight average molecular weight of 4,000 Daltons or greater, especially 4,000 to 2,000,000 Daltons, more preferably 10,000 to 1,000,000 and most preferably 10,000 to 100,000 Daltons. Molecular weights are determined according to high-temperature gel permeation chromatography (HT-GPC) using polystyrene standards. The polymers of this invention preferably have a polydispersity of 1.01 to 10, more preferably 1.1 to 3.0, most preferred 1.5 to 2.5. The polymers of the present invention are preferably conjugated.

Oligomers of the present invention preferably have a weight average molecular weight below 4,000 Daltons.

In a preferred embodiment $R^1$ and $R^2$ form together a group

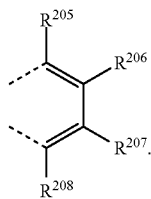

$R^{205}$, $R^{206}$, $R^{207}$ and $R^{208}$ are preferably H.

In another preferred embodiment $R^1$ and $R^2$ are a group of formula

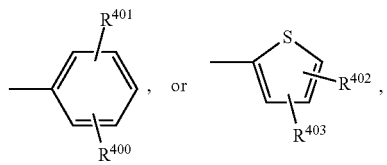

wherein $R^{400}$, $R^{401}$, $R^{402}$ and $R^{403}$ are independently of each other H, CN, F, $CF_3$, $C_1$-$C_{18}$alkoxy; $C_1$-$C_{18}$alkyl; or $C_1$-$C_{18}$alkyl which is interrupted by —O—. $R^{400}$, $R^{401}$, $R^{402}$ and $R^{403}$ are preferably H.

$R^1$ and $R^2$ may be different, but are preferably the same.

In a preferred embodiment the present invention is directed to polymers comprising a repeating unit of the formula

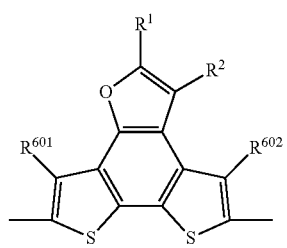

(I)

wherein $R^1$ and $R^2$ are independently of each other a group of formula

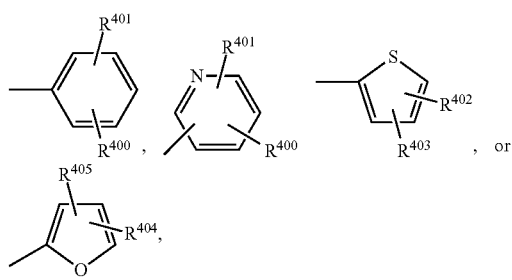

wherein $R^{400}$, $R^{401}$, $R^{402}$, $R^{403}$, $R^{404}$ and $R^{405}$ are independently of each other H, CN, F, $CF_3$, $C_1$-$C_{18}$alkoxy; $C_1$-$C_{18}$alkyl; or $C_1$-$C_{18}$alkyl which is interrupted by —O—, or $R^1$ and $R^2$ form together a group

[structure of a benzene ring with dashed bonds]

$R^{601}$ and $R^{602}$ may be the same or different and are selected from $C_1$-$C_{25}$alkyl, or hydrogen; especially hydrogen. $R^1$ and $R^2$ are especially a group of formula

[phenyl group with substituents $R^{401}$ and $R^{400}$], very especially

[phenyl group],

Among the repeating units of formula I repeating units of formula

[structure showing a fused ring system with two phenyl groups, an oxygen-containing central ring, and two thiophene rings with sulfur atoms]

(Ia) are preferred.

The polymer may be a homopolymer of formula $$*\!-\!\!\left[\!\!-\!A\!-\!\right]_{\!n}\!\!-\!*,$$

wherein A is a repeating unit of formula (I), n is usually in the range of 4 to 1000, especially 4 to 200, very especially 5 to 150.

Alternatively, the polymer may be a polymer, comprising repeating units of the formula $$*\!-\!\!\left[\!\!-\!A\!-\!\right]\!\!-\!*\quad\text{and}\quad *\!-\!\!\left[\!\!-\!COM^1\!-\!\right]\!\!-\!*,$$

especially $$*\!-\!\!\left[\!\!-\!A\!-\!\right]\!\!\left[\!\!-\!COM^1\!-\!\right]\!\!-\!*,$$

very especially a copolymer of formula $$*\!-\!\!\left[\!\left[\!-\!A\!-\!\right]\!\left[\!-\!COM^1\!-\!\right]\!\right]_{\!n}\!\!-\!*, \quad\text{(III)}$$

wherein n is usually in the range of 4 to 1000, especially 4 to 200, very especially 5 to 150.

A is a repeating unit of formula (I), and

—$COM^1$- is a repeating unit $$*\!-\!\!\left[\!-\!Ar^4\!-\!\right]_{\!k}\!\left[\!-\!Ar^5\!-\!\right]_{\!l}\!\left[\!-\!Ar^6\!-\!\right]_{\!r}\!\left[\!-\!Ar^7\!-\!\right]_{\!z}\!\!-\!*,$$

wherein k is 0, 1, 2, or 3; l is 1, 2, or 3; r is 0, 1, 2, or 3; z is 0, 1, 2, or 3;

$Ar^4$, $Ar^5$, $Ar^6$ and $Ar^7$ are independently of each other a group of formula and

[thiophene ring with $R^3$ and $R^{3'}$ substituents] (XIa)

[furan ring with $R^3$ and $R^{3'}$ substituents] (XIb)

[pyrrole ring with $R^3$, $R^{3'}$ and $R^8$ on N] (XIc)

[thiazole ring with $R^{3'}$] (XId)

[selenophene ring with $R^3$ and $R^{3'}$] (XIe)

[thieno[3,2-b]thiophene with $R^3$ and $R^{3'}$] (XIf)

[thieno[2,3-b]thiophene with $R^3$ and $R^{3'}$] (XIg)

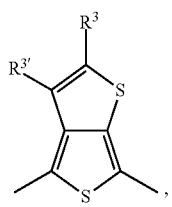 (XIh)
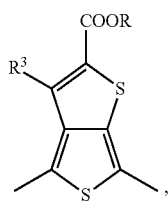 (XIi)
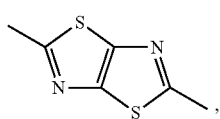 (XIj)
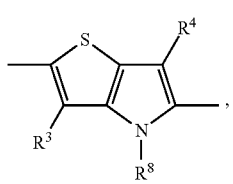 (XIk)
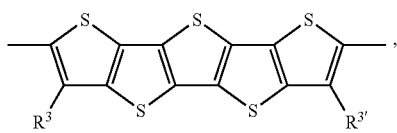 (XIl)
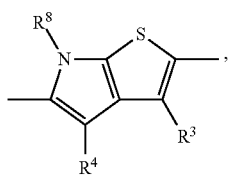 (XIm)
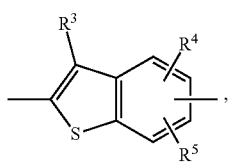 (XIn)
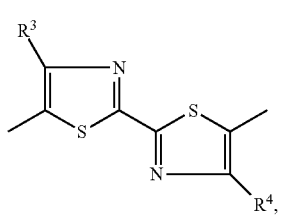 (XIo)
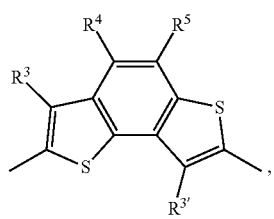 (XIpa)
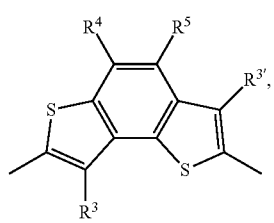 (XIpb)
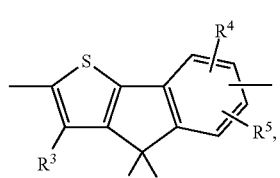 (XIq)
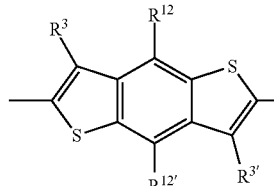 (XIr)
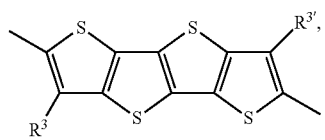 (XIs)
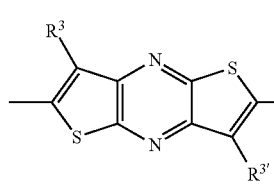 (XIt)
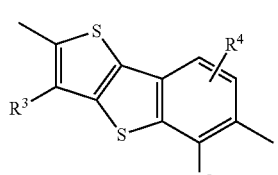 (XIu)
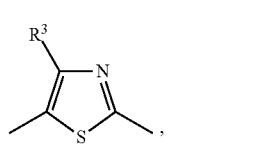 (XIv)

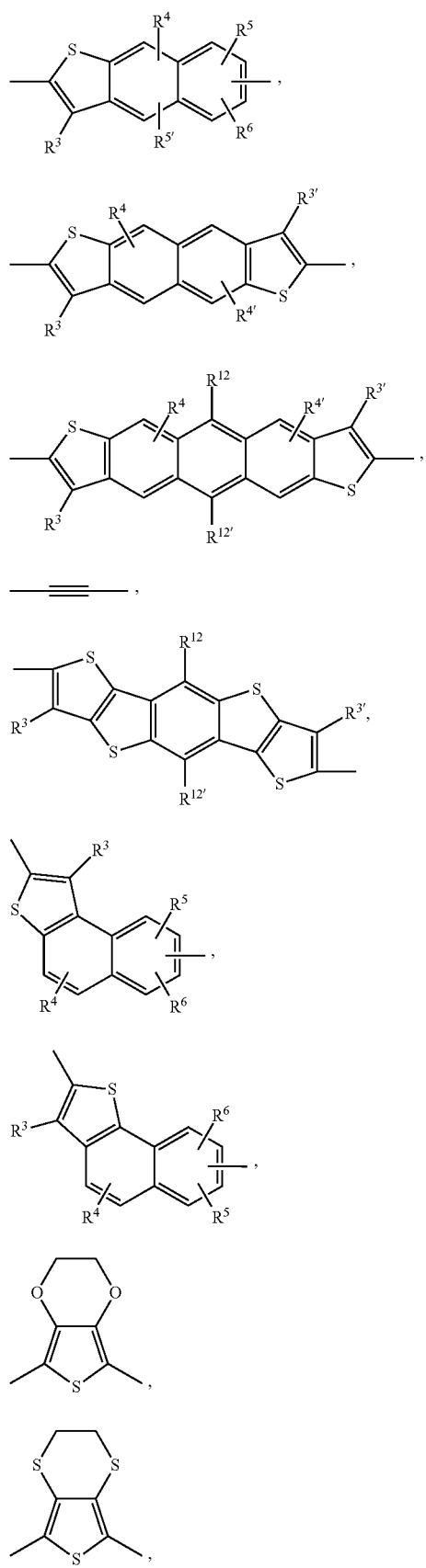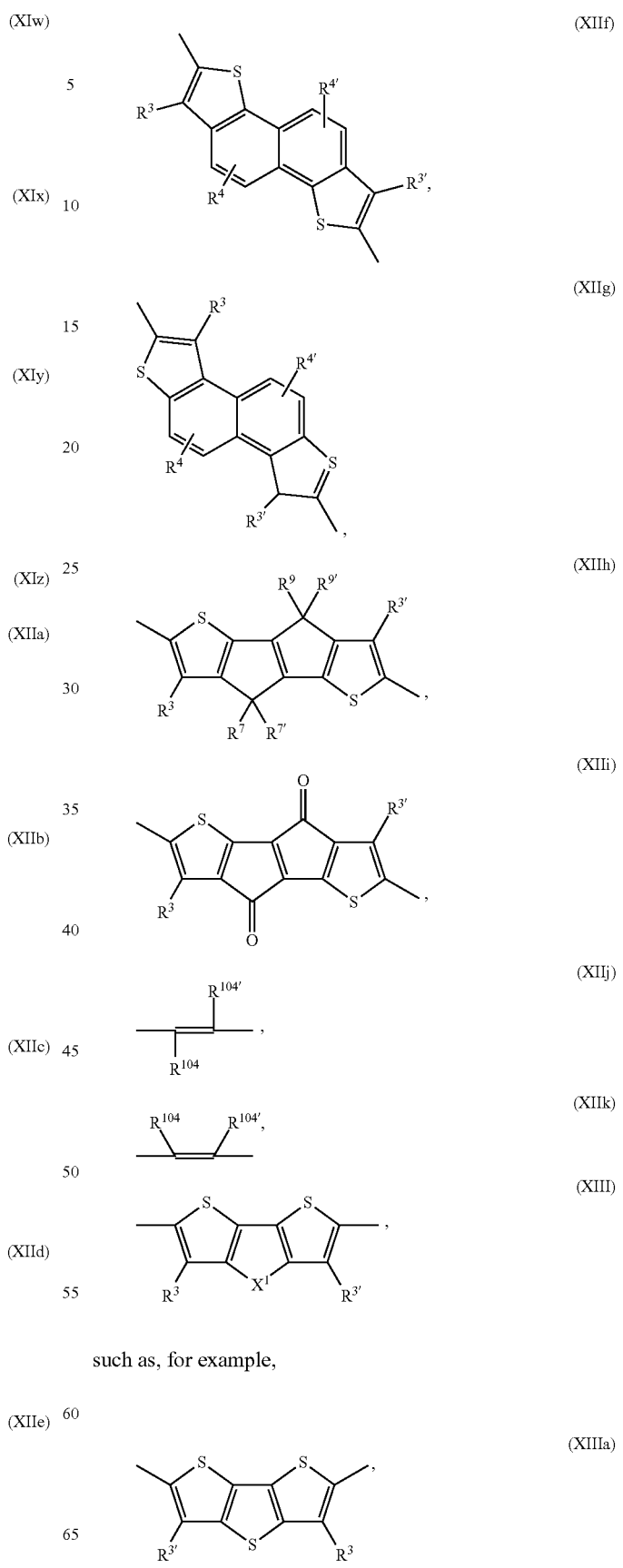
such as, for example,

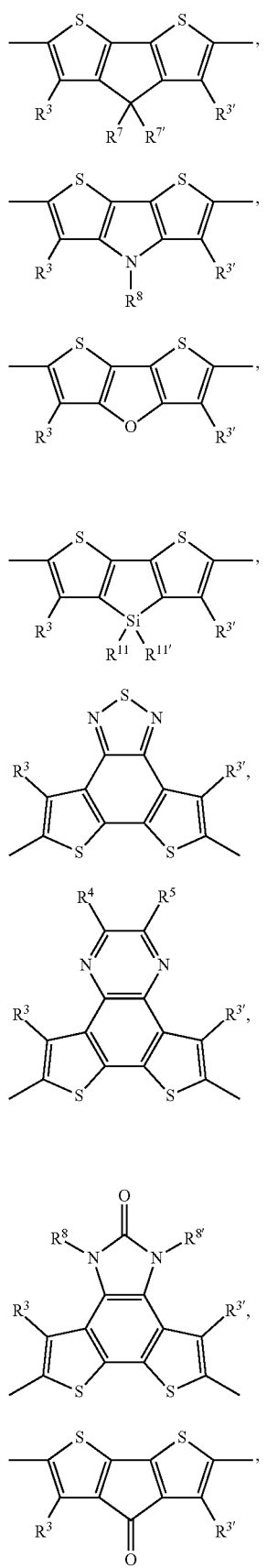
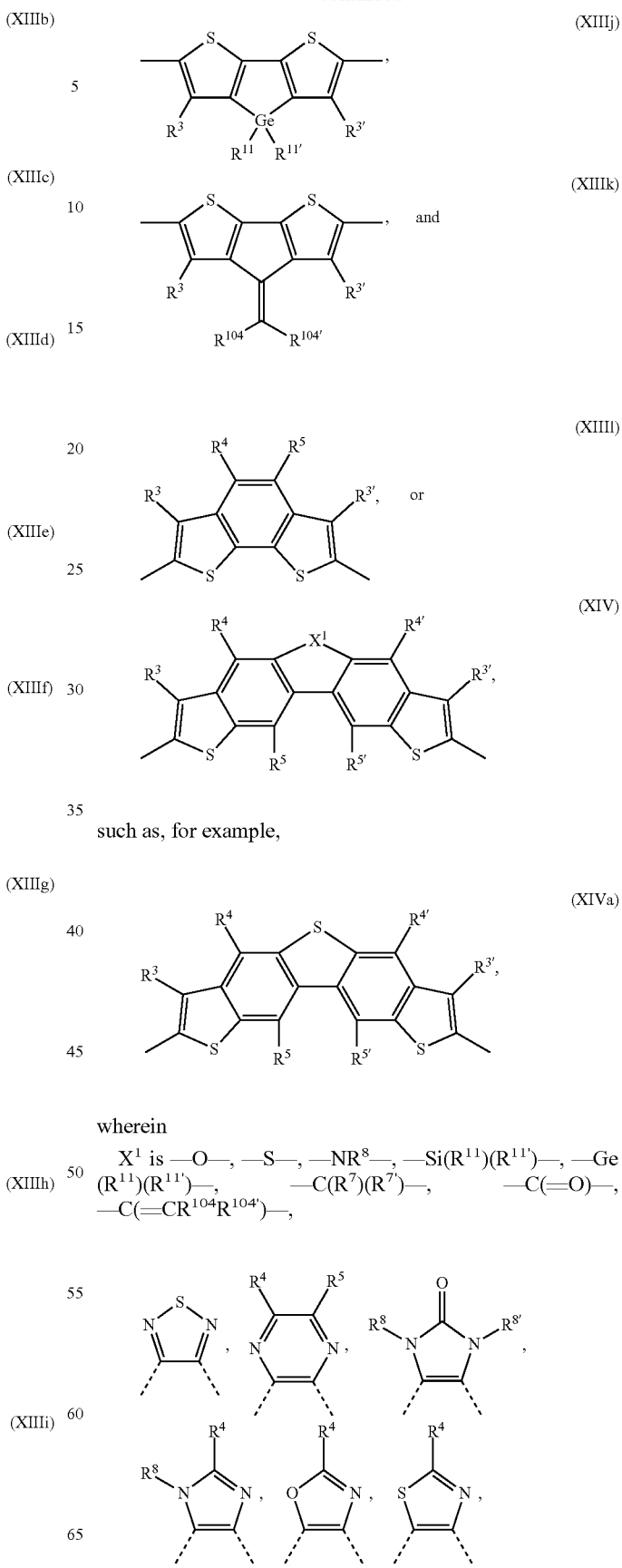
such as, for example,
wherein
X¹ is —O—, —S—, —NR⁸—, —Si(R¹¹)(R¹¹')—, —Ge(R¹¹)(R¹¹')—, —C(R⁷)(R⁷')—, —C(=O)—, —C(=CR¹⁰⁴R¹⁰⁴')—, -continued
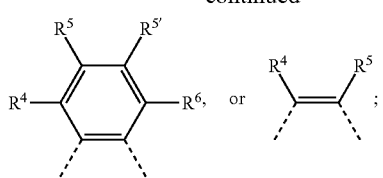
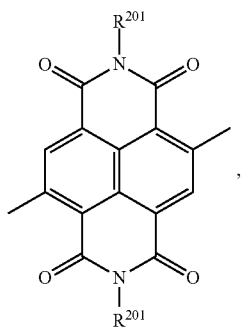
(XVa)
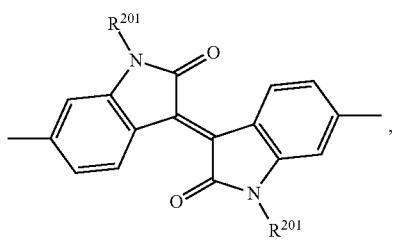
(XVb)
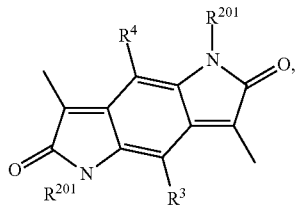
(XVc)
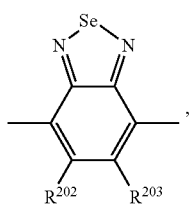
(XVd)
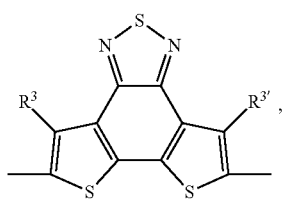
(XVe)
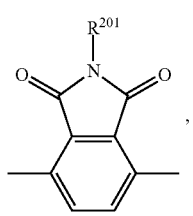
(XVf)
-continued
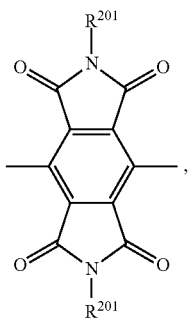
(XVg)
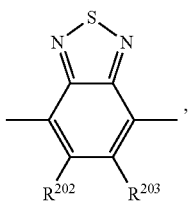
(XVh)
(XVi)
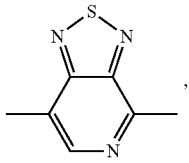
(XVj)
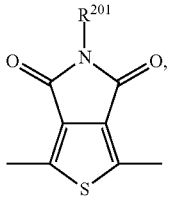
(XVk)
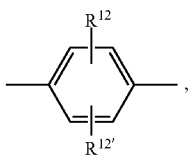
(XVl)
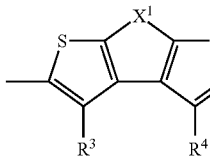
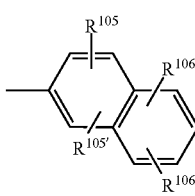
(XVm)

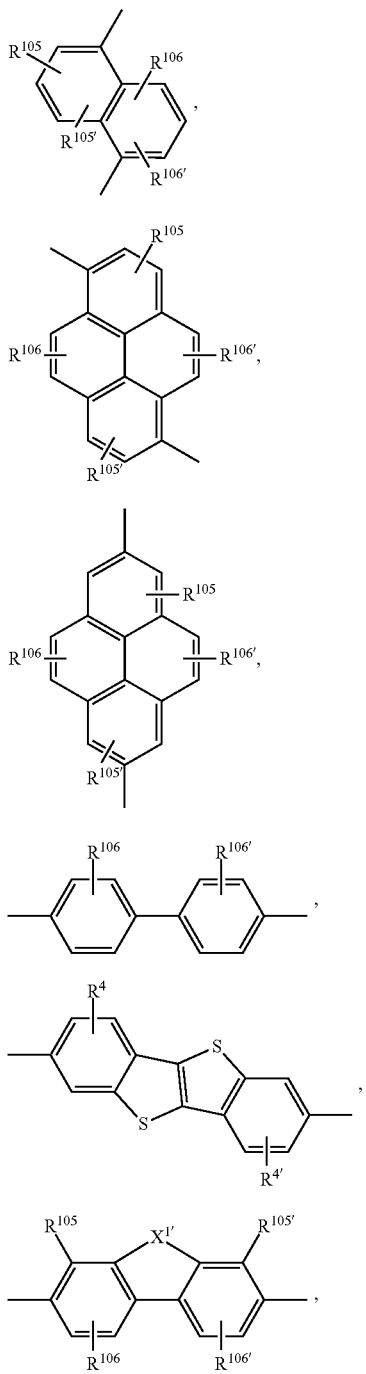
such as, for example,
wherein
X$^{1'}$ is S, O, NR$^{107}$—, —Si(R$^{117}$)(R$^{117'}$)—, —Ge(R$^{117}$)(R$^{117'}$)—, —C(R$^{106}$)(R$^{109}$)—, —C(=O)—, —C(=CR$^{104}$R$^{104'}$)—,

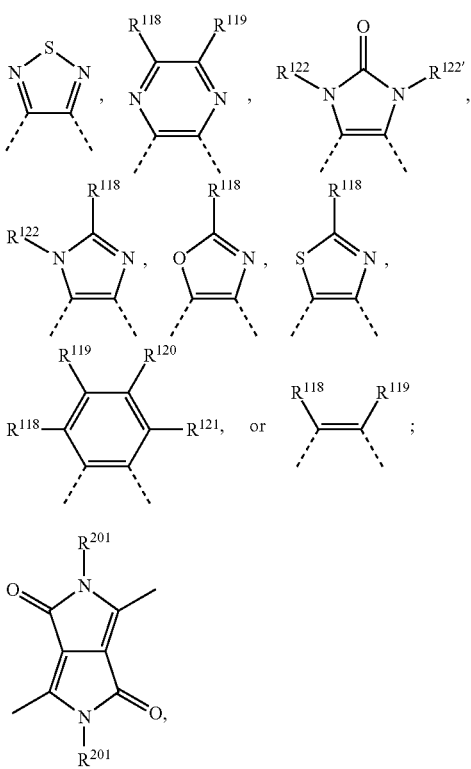

(XVu)

R³ and R³' are independently of each other hydrogen, halogen, halogenated $C_1$-$C_{25}$alkyl, cyano, $C_1$-$C_{25}$alkyl, which may optionally be interrupted by one or more oxygen or sulphur atoms; $C_7$-$C_{25}$arylalkyl, or $C_1$-$C_{25}$alkoxy;

$R^{104}$ and $R^{104'}$ are independently of each other hydrogen, cyano, COOR$^{103}$, a $C_1$-$C_{25}$alkyl group, or $C_6$-$C_{24}$aryl or $C_2$-$C_{20}$heteroaryl, $R^4$, $R^{4'}$, $R^5$, $R^{5'}$, $R^6$, and $R^{6'}$ are independently of each other hydrogen, halogen, halogenated $C_1$-$C_{25}$alkyl, cyano, $C_1$-$C_{25}$alkyl, which may optionally be interrupted by one or more oxygen or sulphur atoms; $C_7$-$C_{25}$arylalkyl, or $C_1$-$C_{25}$alkoxy;

$R^7$, $R^{7'}$, $R^9$ and $R^{9'}$ are independently of each other hydrogen, $C_1$-$C_{25}$alkyl, which may optionally be interrupted by one, or more oxygen, or sulphur atoms; or $C_7$-$C_{25}$arylalkyl, $R^8$ and $R^{8'}$ are independently of each other hydrogen, $C_6$-$C_{18}$aryl; $C_6$-$C_{18}$aryl which is substituted by $C_1$-$C_{18}$alkyl, or $C_1$-$C_{18}$alkoxy; or $C_1$-$C_{25}$alkyl, which may optionally be interrupted by one or more oxygen or sulphur atoms; or $C_7$-$C_{25}$arylalkyl, $R^{11}$ and $R^{11'}$ are independently of each other $C_1$-$C_{25}$alkyl group, $C_7$-$C_{25}$arylalkyl, or a phenyl group, which can be substituted one to three times with $C_1$-$C_8$alkyl and/or $C_1$-$C_8$alkoxy;

$R^{12}$ and $R^{12'}$ are independently of each other hydrogen, halogen, cyano, $C_1$-$C_{25}$alkyl, which may optionally be interrupted by one, or more oxygen, or sulphur atoms, $C_1$-$C_{25}$alkoxy, $C_7$-$C_{25}$arylalkyl, or

wherein $R^{13}$ is a $C_1$-$C_{10}$alkyl group, or a tri($C_1$-$C_8$alkyl)silyl group; or $R^{104}$ and $R^{104'}$ are independently of each other hydrogen, $C_1$-$C_{18}$alkyl, $C_6$-$C_{10}$aryl, which may optionally be substituted by G, or $C_2$-$C_8$heteroaryl, which may optionally be substituted by G, $R^{105}$, $R^{105'}$, $R^{106}$ and $R^{106'}$ are independently of each other hydrogen, halogen, cyano, $C_1$-$C_{25}$alkyl, which may optionally be interrupted by one or more oxygen or sulphur atoms; $C_7$-$C_{25}$arylalkyl, or $C_1$-$C_{18}$alkoxy, $R^{107}$ is hydrogen, $C_7$-$C_{25}$arylalkyl, $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$perfluoroalkyl; $C_1$-$C_{25}$alkyl; which may be interrupted by —O—, or —S—; or —COOR$^{103}$;

$R^{108}$ and $R^{109}$ are independently of each other H, $C_1$-$C_{25}$alkyl, $C_1$-$C_{25}$alkyl which is substituted by E and/or interrupted by D, $C_7$-$C_{25}$arylalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, or $C_7$-$C_{25}$aralkyl, or $R^{108}$ and $R^{109}$ together form a group of formula =CR$^{110}$R$^{111}$, wherein $R^{110}$ and $R^{111}$ are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, or $C_2$-$C_{20}$heteroaryl, or $C_2$-$C_{20}$heteroaryl which is substituted by G, or $R^{108}$ and $R^{109}$ together form a five or six membered ring, which optionally can be substituted by $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, or $C_7$-$C_{25}$aralkyl, D is —CO—, —COO—, —S—, —O—, or —NR$^{112'}$—, E is $C_1$-$C_8$thioalkoxy, $C_1$-$C_8$alkoxy, CN, —NR$^{112'}$R$^{113'}$, —CONR$^{112'}$R$^{113'}$, or halogen, G is E, or $C_1$-$C_{18}$alkyl, and $R^{112'}$ and $R^{113'}$ are independently of each other H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{115}$ and $R^{115'}$ are independently of each other hydrogen, halogen, cyano, $C_1$-$C_{25}$alkyl, which may optionally be interrupted by one, or more oxygen, or sulphur atoms, $C_1$-$C_{25}$alkoxy, $C_7$-$C_{25}$arylalkyl, or

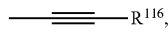

wherein $R^{116}$ is a $C_1$-$C_{10}$alkyl group, or a tri($C_1$-$C_8$alkyl)silyl group;

$R^{117}$ and $R^{117'}$ are independently of each other $C_1$-$C_{25}$alkyl group, $C_7$-$C_{25}$arylalkyl, or a phenyl group, which can be substituted one to three times with $C_1$-$C_8$alkyl and/or $C_1$-$C_8$alkoxy;

$R^{118}$, $R^{119}$, $R^{120}$ and $R^{121}$ are independently of each other hydrogen, halogen, halogenated $C_1$-$C_{25}$alkyl, cyano, $C_1$-$C_{25}$alkyl, which may optionally be interrupted by one or more oxygen or sulphur atoms; $C_7$-$C_{25}$arylalkyl, or $C_1$-$C_{25}$alkoxy;

$R^{122}$ and $R^{122'}$ are independently of each other hydrogen, $C_6$-$C_{18}$aryl; $C_6$-$C_{18}$aryl which is substituted by $C_1$-$C_{18}$alkyl, or $C_1$-$C_{18}$alkoxy; or $C_1$-$C_{25}$alkyl, which may optionally be interrupted by one or more oxygen or sulphur atoms; or $C_7$-$C_{25}$arylalkyl.

$R^{201}$ is selected from hydrogen, a $C_1$-$C_{100}$alkyl group, —COOR$^{103}$, a $C_1$-$C_{100}$alkyl group substituted by one or more halogen atoms, hydroxyl groups, nitro groups, —CN, or $C_6$-$C_{18}$aryl groups and/or interrupted by —O—, —COO—, —OCO— or —S—; a $C_7$-$C_{25}$arylalkyl group, a carbamoyl group, a $C_5$-$C_{12}$cycloalkyl group, which can be substituted one to three times with $C_1$-$C_{100}$alkyl and/or $C_1$-$C_{100}$alkoxy, a $C_6$-$C_{24}$aryl group, in particular phenyl or 1- or 2 naphtyl which can be substituted one to three times with $C_1$-$C_{100}$alkyl, $C_1$-$C_{100}$thioalkoxy, and/or $C_1$-$C_{100}$alkoxy; and pentafluorophenyl;

$R^{103}$ and $R^{114}$ are independently of each other $C_1$-$C_{25}$alkyl, which may optionally be interrupted by one, or more oxygen, or sulphur atoms, $R^{202}$ and $R^{203}$ may be the same or different and are selected from H, F, —CN, $C_1$-$C_{100}$alkyl, which may optionally be interrupted by one or more oxygen, or sulphur atoms; and $C_1$-$C_{100}$alkoxy.

The above-mentioned repeating units COM$^1$ are known and can be prepared according to known procedures. With respect to DPP repeating units and their synthesis reference is, for example, made to U.S. Pat. No. 6,451,459B1, WO05/049695, WO2008/000664, EP2034537A2, EP2075274A1, WO2010/049321, WO2010/049323, WO2010/108873, WO2010/115767, WO2010/136353, WO2010/136352 and PCT/EP2011/057878.

$R^3$, $R^{3'}$, $R^4$ and $R^{4'}$ are preferably hydrogen, or $C_1$-$C_{25}$alkyl.

$R^{201}$ is preferably a linear, or branched $C_1$-$C_{36}$alkyl group, such as, for example, methyl, ethyl, n-propyl, isopropyl, n-butyl, sec.-butyl, isobutyl, tert.-butyl, n-pentyl, 2-pentyl, 3-pentyl, 2,2-dimethylpropyl, 1,1,3,3-tetramethylpentyl, n-hexyl, 1-methylhexyl, 1,1,3,3,5,5-hexamethylhexyl, n-heptyl, isoheptyl, 1,1,3,3-tetramethylbutyl, 1-methylheptyl, 3-methylheptyl, n-octyl, 1,1,3,3-tetramethylbutyl and 2-ethylhexyl, n-nonyl, decyl, undecyl, especially n-dodecyl, tridecyl, tetradecyl, pentadecyl, hexadecyl, 2-ethyl-hexyl, 2-butyl-hexyl, 2-butyl-octyl, 2-hexyldecyl, 2-decyl-tetradecyl, heptadecyl, octadecyl, eicosyl, heneicosyl, docosyl, or tetracosyl.

Advantageously, the groups $R^{201}$ can be represented by formula

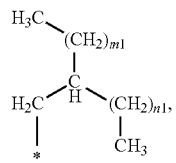

wherein m1=n1+2 and m1+n1≤24. Chiral side chains can either be homochiral, or racemic, which can influence the morphology of the compounds.

—COM$^1$- preferably a repeating unit of formula

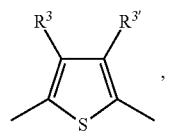

(XIa)

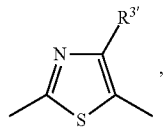

(XId)

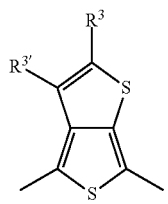

(XIh)

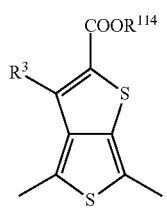

(XIi)

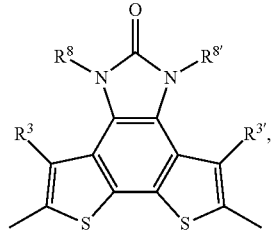

(XIIIh)

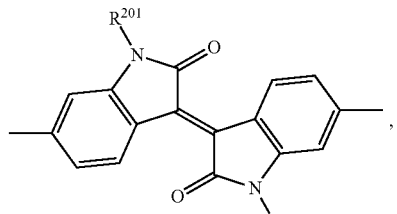

(XVb)

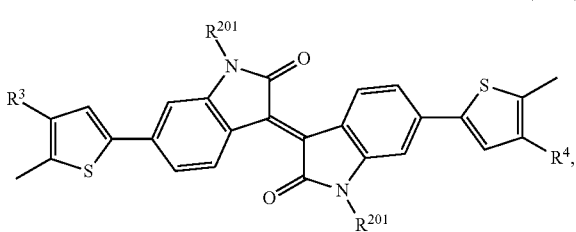

(XVb')

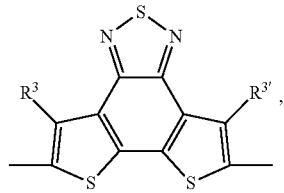

(XVe)

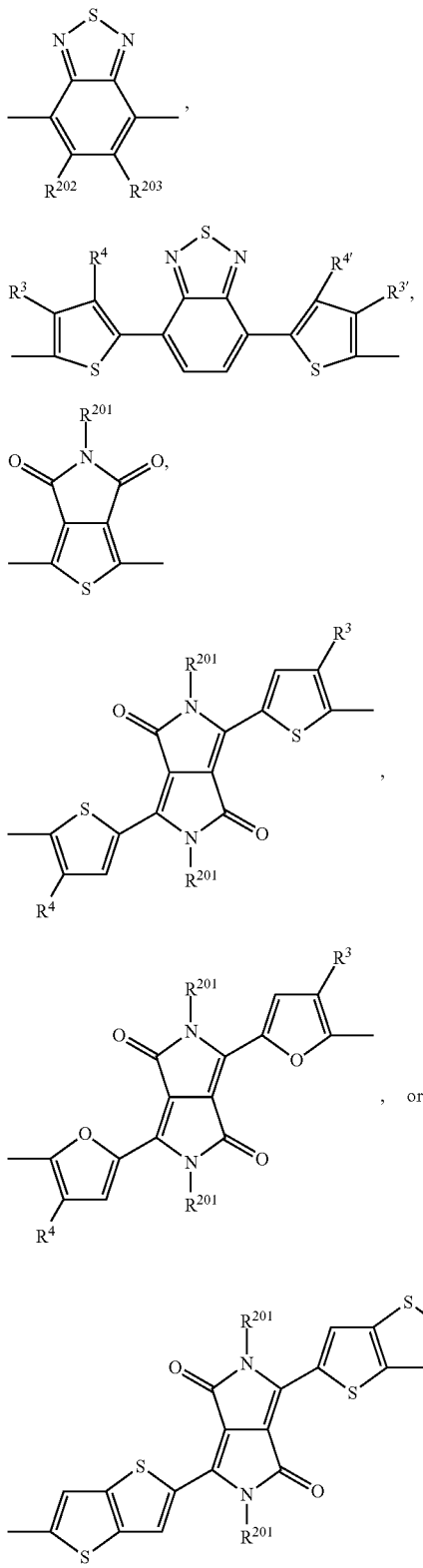

$R^{201}$ is a $C_1$-$C_{38}$alkyl group; and
$R^{202}$ and $R^{203'}$ are independently of each other hydrogen or $C_1$-$C_{25}$alkyl.

In a particularly preferred embodiment $COM^1$ is selected from repeating units of formula (XVb), (XVb'), (XVe), (XVh), (XVh'), (XVu'), (XVu''), and (XVu'''), especially (XVb), (XVb'), (XVu'), (XVu''), and (XVu''').

In a preferred embodiment of the present invention the polymer is a copolymer, comprising repeating units of formula

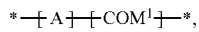

especially a copolymer of formula

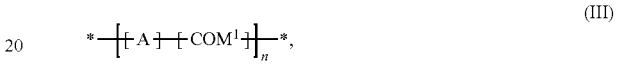

wherein A and $COM^1$ are as defined above; n is a number which results in a molecular weight of 4,000 to 2,000,000 Daltons, more preferably 10,000 to 1,000,000 and most preferably 10,000 to 100,000 Daltons. n is usually in the range of 4 to 1000, especially 4 to 200, very especially 5 to 150. The polymer structure represented by formula III is an idealized representation of the polymer products obtained, for example, via the Suzuki polymerization procedure. The repeating unit of formula

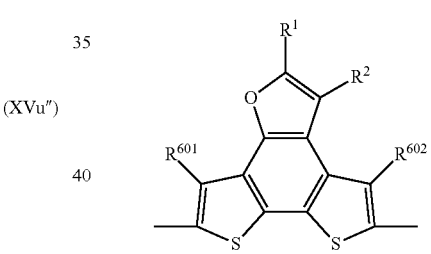

can be incorporated into the polymer chain in two ways:

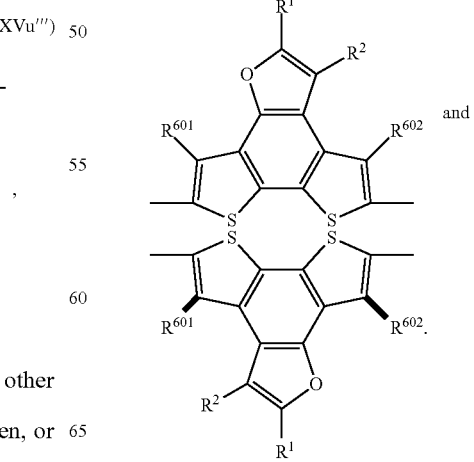

Both possibilities shall be covered by formula (III).

wherein $R^3$, $R^{3'}$, $R^4$ and $R^{4'}$ are independently of each other hydrogen, or $C_1$-$C_{25}$alkyl;
$R^8$ and $R^{8'}$ are independently of each other hydrogen, or $C_1$-$C_{25}$alkyl;
$R^{114}$ is a $C_1$-$C_{38}$alkyl group;

The polymers of the present invention can comprise more than 2 different repeating units, such as, for example, repeating units A, COM¹ and B, which are different from each other. In said embodiment the polymer is a copolymer, comprising repeating units of formula

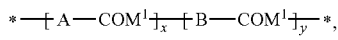

wherein x=0.995 to 0.005, y=0.005 to 0.995, especially x=0.2 to 0.8, y=0.8 to 0.2, and x+y=1. B has the meaning of COM¹, with the proviso that B is different from COM¹. A and COM¹ are as defined above.

In another preferred embodiment of the present invention A is a repeating unit of formula (I), especially (Ia), as defined above, and

is a group of formula

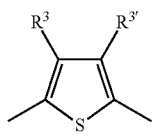
(XIa)

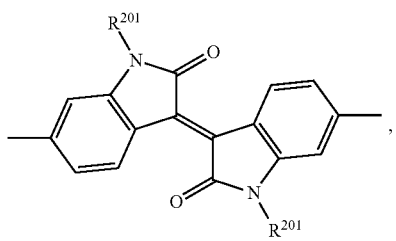
(XVb)

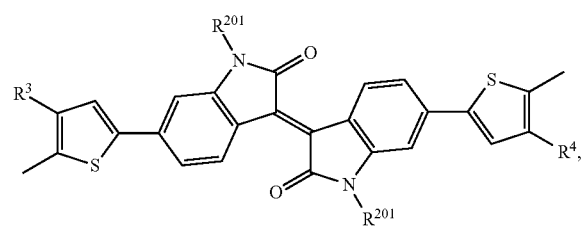
(XVb')

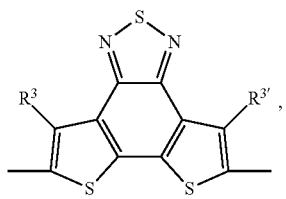
(XVe)

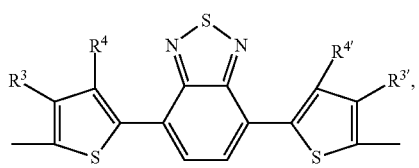
(XVh')

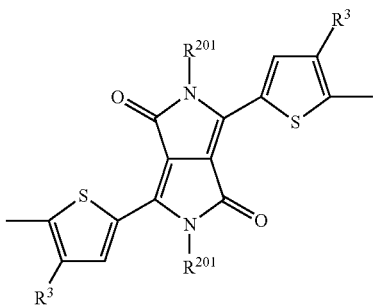
(XVu'),

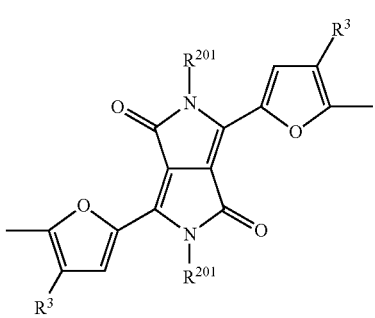
(XVu''), or

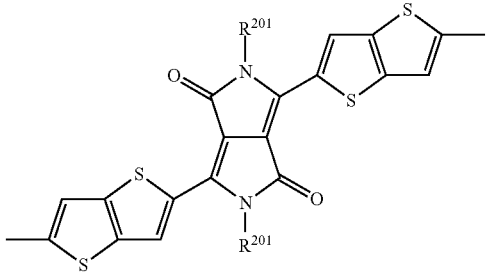
(XVu''');

wherein $R^3$, $R^{3'}$, $R^4$ and $R^{4'}$ are independently of each other hydrogen or $C_1$-$C_{25}$alkyl;

$R^8$ and $R^{8'}$ are independently of each other hydrogen or $C_1$-$C_{25}$alkyl; and $R^{201}$ is a $C_1$-$C_{38}$alkyl group.

COM¹ is preferably a repeating unit of formula (XVb'), (XVb'), (XVu') and (XVu'').

Among the repeating units of formula (I) repeating units of formula (I) are preferred, wherein $R^1$ and $R^2$ are independently of each other a group of formula

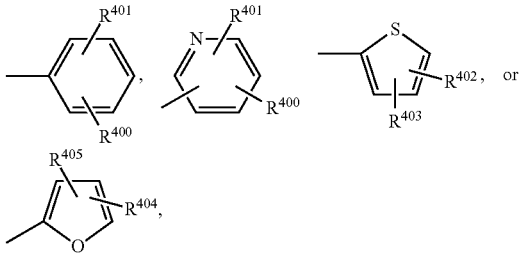

wherein $R^{400}$, $R^{401}$, $R^{402}$, $R^{403}$, $R^{404}$ and $R^{405}$ are independently of each other H, CN, F, $CF_3$, $C_1$-$C_{18}$alkoxy; $C_1$-$C_{18}$alkyl; or $C_1$-$C_{18}$alkyl which is interrupted by —O—, or $R^1$ and $R^2$ form together a group

$R^1$ and $R^2$ are especially a group of formula

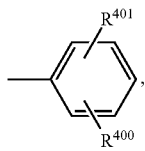

very especially a group of formula

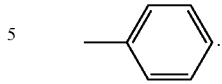

$R^1$ and $R^2$ may be the different, but are preferably the same. $R^{601}$ and $R^{602}$ may be the different, but are preferably the same and are selected from hydrogen, or $C_1$-$C_{25}$alkyl, especially hydrogen. Most preferred are repeating units of formula (Ia).

Among the copolymers of formula III the following copolymers are preferred:

(Ia1)
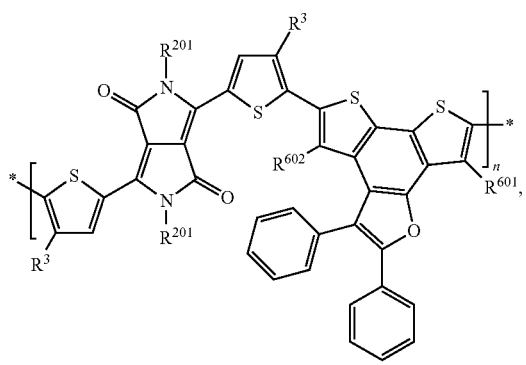

(Ia2)
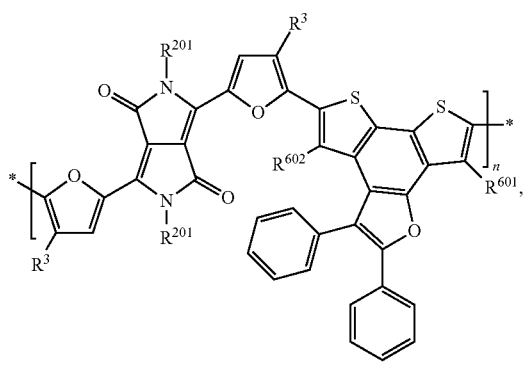

(Ia3)
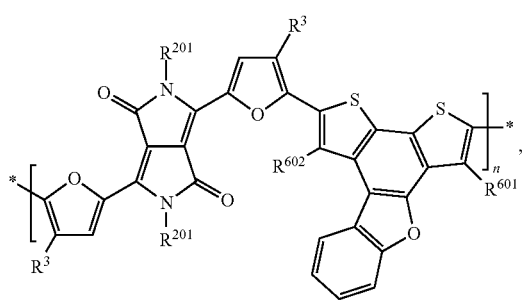

(Ia4)
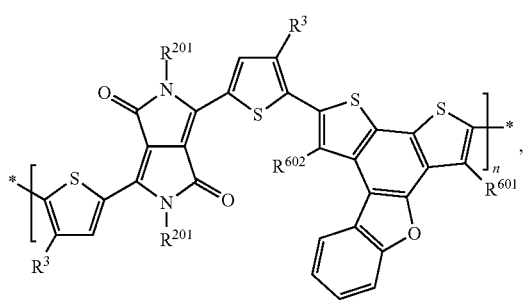

(Ia5)
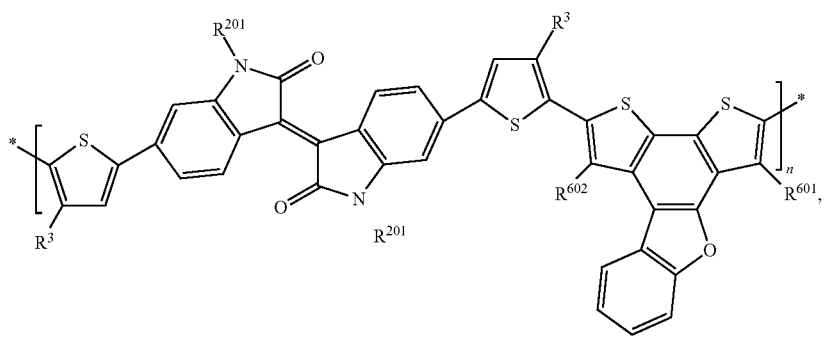

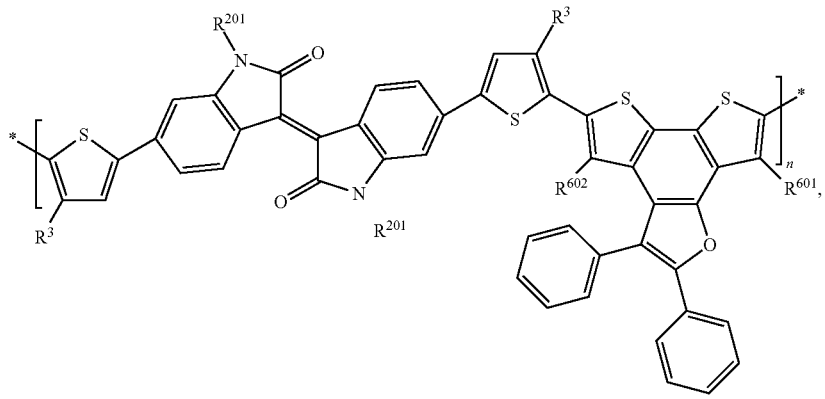
(Ia6)
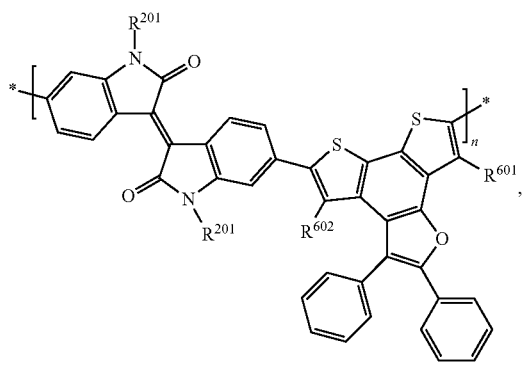
(Ia7)
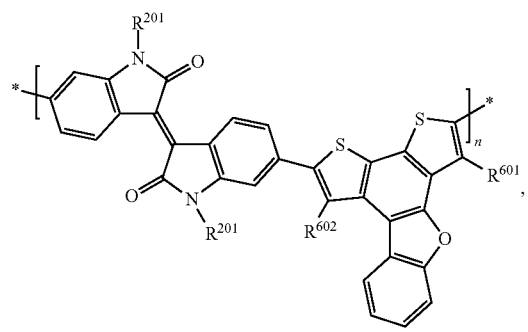
(Ia8)
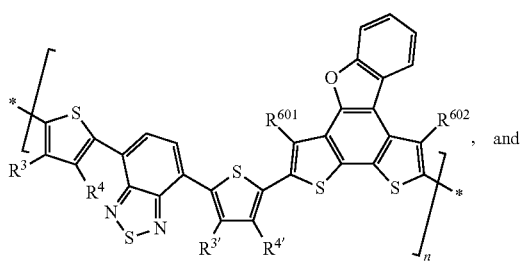
(Ia9), and
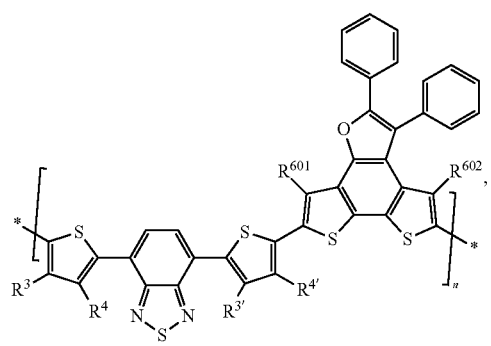
(Ia10)
wherein
n is 4 to 1000, especially 4 to 200, very especially 5 to 150;
$R^3$, $R^{3'}$, $R^4$ and $R^{4'}$ are independently of each other hydrogen or $C_1$-$C_{25}$alkyl;
$R^{201}$ is a $C_1$-$C_{38}$alkyl group, and
$R^{601}$ and $R^{602}$ are independently of each other hydrogen, or $C_1$-$C_{25}$alkyl; especially hydrogen. Polymers of formula (Ia1), (Ia2), (Ia6) and (Ia7) are more preferred.

Examples of particularly preferred polymers are shown below:
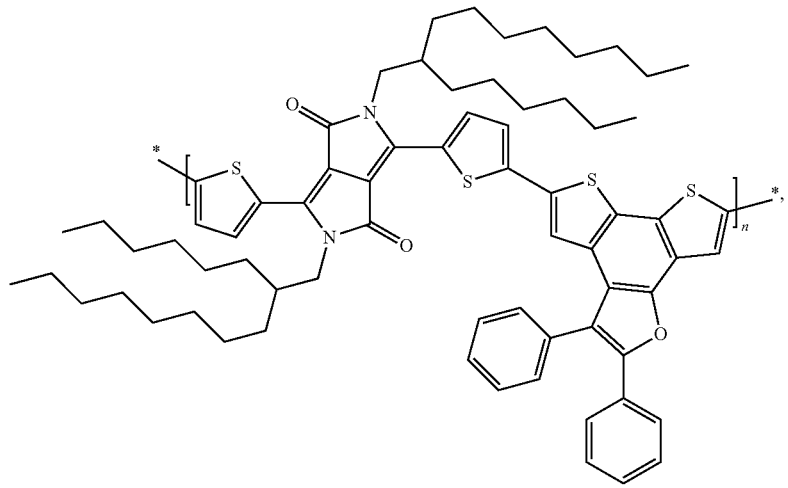
(P-1)
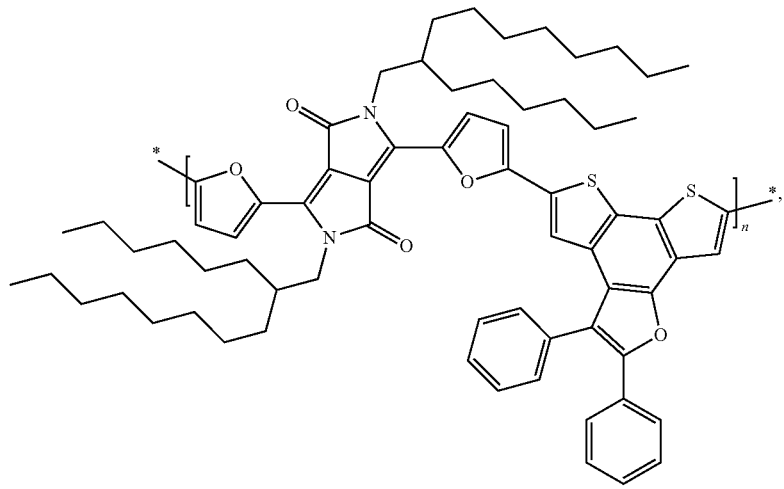
(P-2)
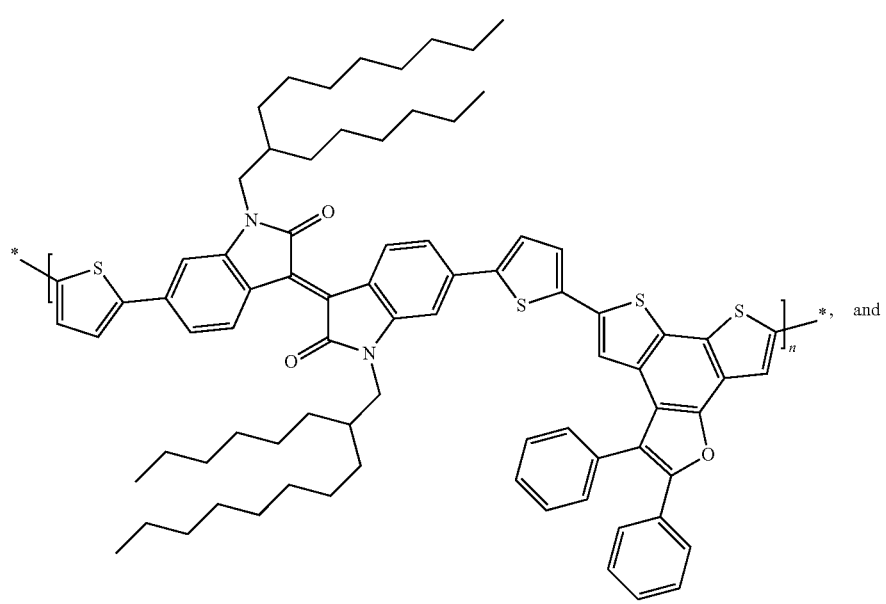
(P-3)
, and

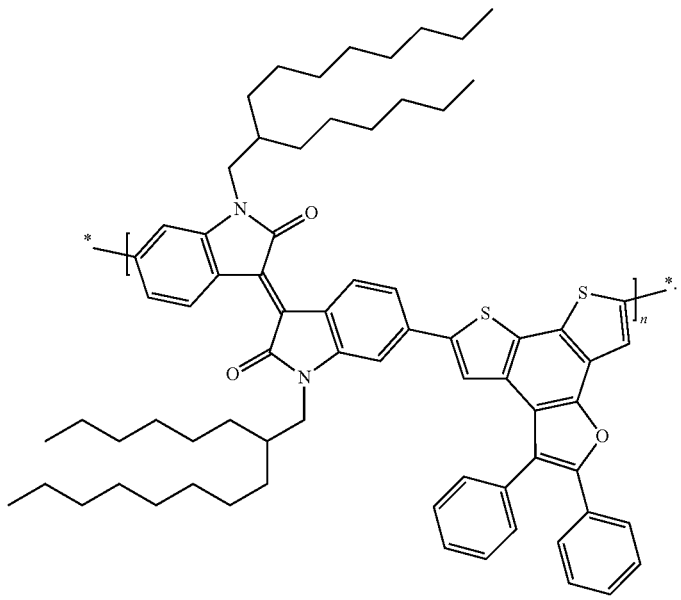

(P-4)

Copolymers of formula III can be obtained, for example, by the Suzuki reaction. The condensation reaction of an aromatic boronate and a halogenide, especially a bromide, commonly referred to as the "Suzuki reaction", is tolerant of the presence of a variety of organic functional groups as reported by N. Miyaura and A. Suzuki in Chemical Reviews, Vol. 95, pp. 457-2483 (1995). Preferred catalysts are 2-dicyclohexylphosphino-2',6'-di-alkoxybiphenyl/palladium(II)acetates, tri-alykl-phosphonium salts/palladium (0) derivatives and tri-alkylphosphine/palladium (0) derivatives. Especially preferred catalysts are 2-dicyclohexylphosphino-2',6'-di-methoxybiphenyl (sPhos)/palladium(II)acetate and, tri-tert-butylphosphonium tetrafluoroborate ((t-Bu)$_3$P*HBF$_4$)/tris (dibenzylideneacetone)dipalladium (0) (Pd$_2$(dba)$_3$) and tri-tert-butylphosphine (t-Bu)$_3$P/tris(dibenzylideneacetone) dipalladium (0) (Pd$_2$(dba)$_3$). This reaction can be applied to preparing high molecular weight polymers and copolymers.

To prepare polymers corresponding to formula III a dihalogenide of formula $X^{10}$-A-$X^{10}$ is reacted with an (equimolar) amount of a diboronic acid or diboronate corresponding to formula

or a dihalogenide of formula

is reacted with an (equimolar) amount of a diboronic acid or diboronate corresponding to formula $X^{11}$-A-$X^{11}$, wherein $X^{10}$ is halogen, especially Br, and $X^{11}$ is independently in each occurrence —B(OH)$_2$, —B(OY$^1$)$_2$,

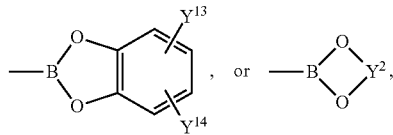

wherein $Y^1$ is independently in each occurrence a $C_1$-$C_{10}$alkyl group and $Y^2$ is independently in each occurrence a $C_2$-$C_{10}$alkylene group, such as —CY$^3$Y$^4$—CY$^5$Y$^6$—, or —CY$^7$Y$^8$—CY$^9$Y$^{10}$—CY$^{11}$C$^{12}$—, wherein $Y^3$, $Y^4$, $Y^5$, $Y^6$, $Y^7$, $Y^8$, $Y^9$, $Y^{10}$, $Y^{11}$ and $Y^{12}$ are independently of each other hydrogen, or a $C_1$-$C_{10}$alkyl group, especially —C(CH$_3$)$_2$C (CH$_3$)$_2$—, —CH$_2$C(CH$_3$)$_2$CH$_2$—, or —C(CH$_3$)$_2$CH$_2$C (CH$_3$)$_2$—, and $Y^{13}$ and $Y^{14}$ are independently of each other hydrogen, or a $C_1$-$C_{10}$alkyl group, under the catalytic action of Pd and triphenylphosphine. The reaction is typically conducted at about 0° C. to 180° C. in an aromatic hydrocarbon solvent such as toluene, xylene. Other solvents such as dimethylformamide, dioxane, dimethoxyethan and tetrahydrofuran can also be used alone, or in mixtures with an aromatic hydrocarbon. An aqueous base, preferably sodium carbonate or bicarbonate, potassium phosphate, potassium carbonate or bicarbonate is used as activation agent for the boronic acid, boronate and as the HBr scavenger. A polymerization reaction may take 0.2 to 100 hours. Organic bases, such as, for example, tetraalkylammonium hydroxide, and phase transfer catalysts, such as, for example TBAB, can promote the activity of the boron (see, for example, Leadbeater & Marco; Angew. Chem. Int. Ed. Eng. 42 (2003) 1407 and references cited therein). Other variations of reaction conditions are given by T. I. Wallow and B. M. Novak in J. Org. Chem. 59 (1994) 5034-5037; and M. Remmers, M. Schulze, and G. Wegner in Macromol. Rapid Commun. 17 (1996) 239-252. Control of molecular weight is possible by using either an excess of dibromide, diboronic acid, or diboronate, or a chain terminator.

According to the process described in WO2010/136352 the polymerisation is carried out in presence of
 a) a catalyst/ligand system comprising a palladium catalyst and an organic phosphine or phosphonium compound,
 b) a base,
 c) a solvent or a mixture of solvents, characterized in that the organic phosphine is a trisubstituted phosphine of formula

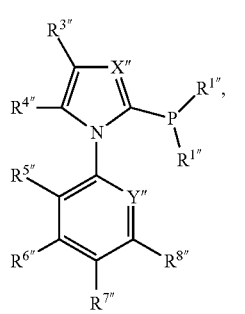

(VI)

or phosphonium salt thereof, wherein X″ independently of Y″ represents a nitrogen atom or a C—R2″ group and Y″ independently of X″ represents a nitrogen atom or a C—R9″ group, R1″ for each of the two R1″ groups independently of the other represents a radical selected from the group $C_1$-$C_{24}$-alkyl, $C_3$-$C_{20}$-cycloalkyl, which includes especially both monocyclic and also bi- and tri-cyclic cycloalkyl radicals, $C_5$-$C_{14}$-aryl, which includes especially the phenyl, naphthyl, fluorenyl radical, $C_2$-$C_{13}$-heteroaryl, wherein the number of hetero atoms, selected from the group N, O, S, may be from 1 to 2, wherein the two radicals R1″ may also be linked to one another, and wherein the above-mentioned radicals R1″ may themselves each be mono- or poly-substituted independently of one another by substituents selected from the group hydrogen, $C_1$-$C_{20}$-alkyl, $C_2$-$C_{20}$-alkenyl, $C_3$-$C_8$-cycloalkyl, $C_2$-$C_9$-hetero-alkyl, $C_5$-$C_{10}$-aryl, $C_2$-$C_9$-heteroaryl, wherein the number of hetero atoms from the group N, O, S may be from 1 to 4, $C_1$-$C_{20}$-alkoxy, $C_1$-$C_{10}$-haloalkyl, hydroxy, amino of the forms NH—($C_1$-$C_{20}$-alkyl), NH—($C_5$-$C_{10}$-aryl), N($C_1$-$C_{20}$-alkyl)$_2$, N($C_1$-$C_{20}$-alkyl)($C_5$-$C_{10}$-aryl), N($C_5$-$C_{10}$-aryl)$_2$, N($C_1$-$C_{20}$-alkyl/$C_5$-$C_{10}$-aryl)$_3$', NH—CO—$C_1$-$C_{20}$-alkyl, NH—CO—$C_5$-$C_{10}$-aryl, carboxylato of the forms COOH and COOQ (wherein Q represents either a monovalent cation or $C_1$-$C_8$-alkyl), $C_1$-$C_6$-acyloxy, sulfinato, sulfonato of the forms SO$_3$H and SO$_3$Q' (wherein Q' represents either a monovalent cation, $C_1$-$C_{20}$-alkyl, or $C_5$-$C_{10}$-aryl), tri-$C_1$-$C_6$-alkylsilyl, wherein two of the mentioned substituents may also be bridged with one another, R2″-R9″ represent a hydrogen, alkyl, alkenyl, cycloalkyl, aromatic or heteroaromatic aryl, O-alkyl, NH-alkyl, N-(alkyl)$_2$, O-(aryl), NH-(aryl), N-(alkyl)(aryl), O—CO-alkyl, O—CO-aryl, F, Si(alkyl)$_3$, CF$_3$, CN, CO$_2$H, COH, SO$_3$H, CONH$_2$, CONH(alkyl), CON(alkyl)$_2$, SO$_2$(alkyl), SO(alkyl), SO(aryl), SO$_2$(aryl), SO$_3$(alkyl), SO$_3$(aryl), S-alkyl, S-aryl, NH—CO(alkyl), CO$_2$(alkyl), CONH$_2$, CO(alkyl), NHCOH, NHCO$_2$(alkyl), CO(aryl), CO$_2$(aryl) radical, wherein two or more adjacent radicals, each independently of the other (s), may also be linked to one another so that a condensed ring system is present and wherein in R2″ to R9″ alkyl represents a hydrocarbon radical having from 1 to 20 carbon atoms which may in each case be linear or branched, alkenyl represents a mono- or poly-unsaturated hydrocarbon radical having from 2 to 20 carbon atoms which may in each case be linear or branched, cycloalkyl represents a hydrocarbon having from 3 to 20 carbon atoms, aryl represents a 5- to 14-membered aromatic radical, wherein from one to four carbon atoms in the aryl radical may also be replaced by hetero atoms from the group nitrogen, oxygen and sulfur so that a 5- to 14-membered heteroaromatic radical is present, wherein the radicals R2″ to R9″ may also carry further substituents as defined for R1″.

The organic phosphines and their synthesis are described in WO2004101581.

Preferred organic phosphines are selected from trisubstituted phosphines of formula

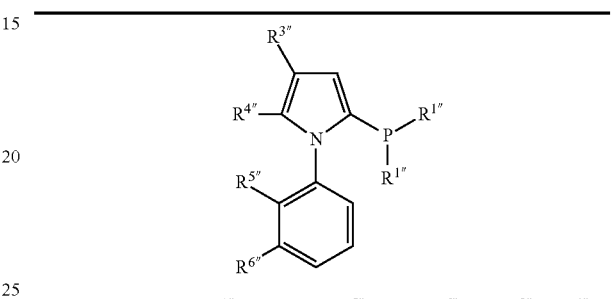

| Cpd. | R1″ | R5″ | R6″ | R3″ | R4″ |
|---|---|---|---|---|---|
| A-1 | H$_3$C—C(CH$_3$)$_2$—CH$_3$ | H | H | H | H |
| A-2 | cyclohexyl | H | H | H | H |
| A-3 | phenyl | H | H | H | H |
| A-4 | adamantyl | H | H | H | H |
| A-5 | cyclohexyl | —OCH$_3$ | H | H | H |
| A-6 | cyclohexyl | 1) | 1) | H | H |
| A-7 | H$_3$C—C(CH$_3$)$_2$—CH$_3$ | 1) | 1) | H | H |
| A-8 | phenyl | 1) | 1) | H | H |
| A-9 | adamantyl | 1) | 1) | H | H |
| A-10 | cyclohexyl | H | H | 2) | 2) |
| A-11 | H$_3$C—C(CH$_3$)$_2$—CH$_3$ | H | H | 2) | 2) |
| A-12 | phenyl | H | H | 2) | 2) |
| A-13 | adamantyl | H | H | 2) | 2) |

1) R5″ and R6″ together form a ring

2) R3″ and R4″ together form a ring

Examples of preferred catalysts include the following compounds:
palladium(II) acetylacetonate, palladium(0) dibenzylidene-acetone complexes, palladium(II) propionate,
 Pd$_2$(dba)$_3$: [tris(dibenzylideneacetone)dipalladium(0)],
 Pd(dba)$_2$: [bis(dibenzylideneacetone) palladium(0)],
 Pd(PR$_3$)$_2$, wherein PR$_3$ is a trisubstituted phosphine of formula VI,
 Pd(OAc)$_2$: [palladium(II) acetate], palladium(II) chloride, palladium(II) bromide, lithium tetrachloropalladate(II), PdCl$_2$(PR$_3$)$_2$; wherein PR$_3$ is a trisubstituted phosphine of formula VI; palladium(0) diallyl ether complexes, palladium (II) nitrate, PdCl$_2$(PhCN)$_2$: [dichlorobis(benzonitrile) palladium(II)], PdCl$_2$(CH$_3$CN): [dichlorobis(acetonitrile) palladium(II)], and PdCl$_2$(COD): [dichloro(1,5-cyclooctadiene) palladium (II)].

Especially preferred are PdCl$_2$, Pd$_2$(dba)$_3$, Pd(dba)$_2$, Pd(OAc)$_2$, or Pd(PR$_3$)$_2$. Most preferred are Pd$_2$(dba)$_3$ and Pd(OAc)$_2$.

The palladium catalyst is present in the reaction mixture in catalytic amounts. The term "catalytic amount" refers to an amount that is clearly below one equivalent of the (hetero) aromatic compound(s), preferably 0.001 to 5 mol-%, most preferably 0.001 to 1 mol-%, based on the equivalents of the (hetero)aromatic compound(s) used.

The amount of phosphines or phosphonium salts in the reaction mixture is preferably from 0.001 to 10 mol-%, most preferably 0.01 to 5 mol-%, based on the equivalents of the (hetero)aromatic compound(s) used. The preferred ratio of Pd:phosphine is 1:4.

The base can be selected from all aqueous and nonaqueous bases and can be inorganic, or organic. It is preferable that at least 1.5 equivalents of said base per functional boron group is present in the reaction mixture. Suitable bases are, for example, alkali and alkaline earth metal hydroxides, carboxylates, carbonates, fluorides and phosphates such as sodium and potassium hydroxide, acetate, carbonate, fluoride and phosphate or also metal alcoholates. It is also possible to use a mixture of bases. The base is preferably a lithium salt, such as, for example, lithium alkoxides (such as, for example, lithium methoxide and lithium ethoxide), lithium hydroxide, carboxylate, carbonate, fluoride and/or phosphate.

The at present most preferred base is aqueous LiOHxH$_2$O (monohydrate of LiOH) and (waterfree) LiOH.

The reaction is typically conducted at about 0° C. to 180° C., preferably from 20 to 160° C., more preferably from 40 to 140° C. and most preferably from 40 to 120° C. A polymerization reaction may take 0.1, especially 0.2 to 100 hours.

In a preferred embodiment of the present invention the solvent is tetrahydrofuran (THF), the base is LiOH*H2O and the reaction is conducted at reflux temperature of THF (about 65° C.).

The solvent is for example selected from toluene, xylenes, anisole, THF, 2-methyltetrahydrofuran, dioxane, chlorobenzene, fluorobenzene or solvent mixtures comprising one or more solvents like e.g. THF/toluene and optionally water. Most preferred is THF, or THF/water.

Advantageously, the polymerisation is carried out in presence of
a) palladium(II) acetate, or Pd$_2$(dba)$_3$, (tris(dibenzylideneacetone)dipalladium(0)) and an organic phosphine A-1 to A-13,
b) LiOH, or LiOHxH$_2$O; and
c) THF, and optionally water. If the monohydrate of LiOH is used, no water needs to be added. The palladium catalyst is present in an amount of preferably about 0.5 mol-%, based on the equivalents of the (hetero)aromatic compound(s) used. The amount of phosphines or phosphonium salts in the reaction mixture is preferably about 2 mol-%, based on the equivalents of the (hetero)aromatic compound(s) used. The preferred ratio of Pd:phosphine is about 1:4.

Preferably the polymerization reaction is conducted under inert conditions in the absence of oxygen. Nitrogen and more preferably argon are used as inert gases.

The process described in WO2010/136352 is suitable for large-scale applications, is readily accessible and convert starting materials to the respective polymers in high yield, with high purity and high selectivity. The process can provide polymers having weight average molecular weights of at least 10,000, more preferably at least 20,000, most preferably at least 30,000. The at present most preferred polymers have a weight average molecular weight of 30,000 to 80,000 Daltons. Molecular weights are determined according to high-temperature gel permeation chromatography (HT-GPC) using polystyrene standards. The polymers preferably have a polydispersibility of 1.01 to 10, more preferably 1.1 to 3.0, most preferred 1.5 to 2.5.

If desired, a monofunctional aryl halide or aryl boronate, such as, for example,

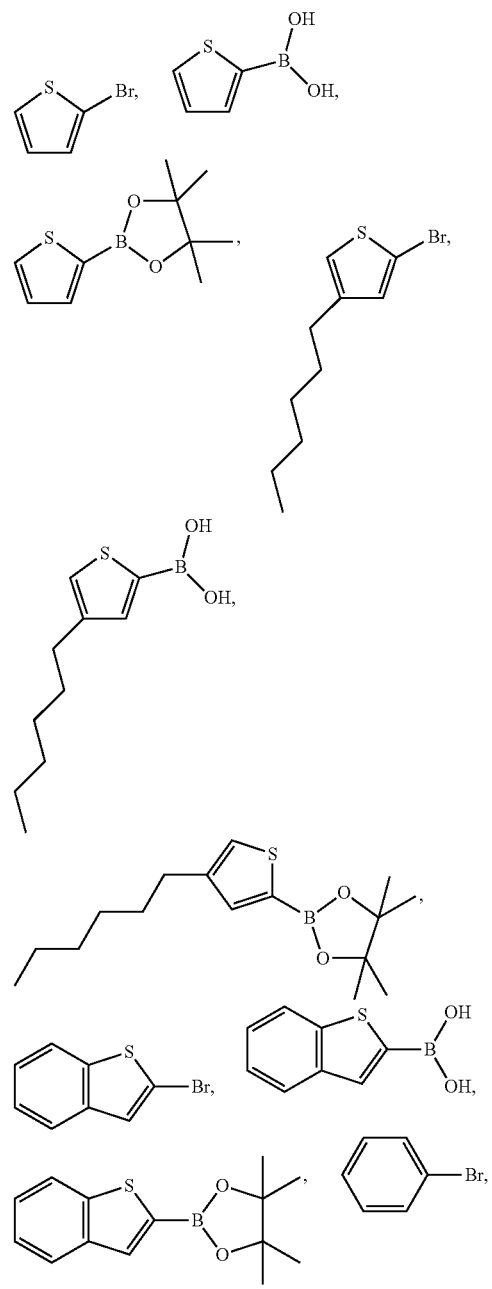

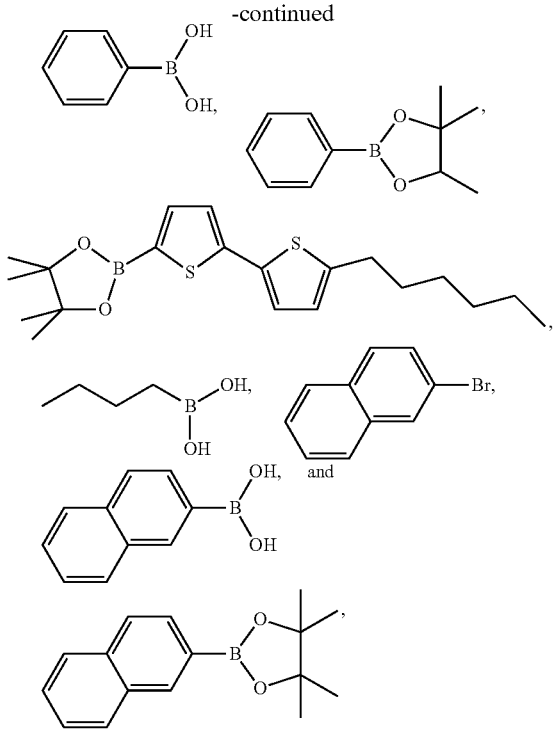

may be used as a chain-terminator in such reactions, which will result in the formation of a terminal aryl group.

It is possible to control the sequencing of the monomeric units in the resulting copolymer by controlling the order and composition of monomer feeds in the Suzuki reaction.

The polymers of the present invention can also be synthesized by the Stille coupling (see, for example, Babudri et al, J. Mater. Chem., 2004, 14, 11-34; J. K. Stille, Angew. Chemie Int. Ed. Engl. 1986, 25, 508). To prepare polymers corresponding to formula III a dihalogenide of formula $X^{10}$-A-$X^{10}$ is reacted with a compound of formula $X^{11'}$—$COM^1$-$X^{11'}$, or a dihalogenide of formula $X^{10}$—$COM^1$-$X^{10}$ is reacted with a compound of formula $X^{11'}$-A-$X^{11'}$, wherein $X^{11'}$ is a group —$SnR^{207}R^{208}R^{209}$ and $X^{10}$ is as defined above, in an inert solvent at a temperature in range from 0° C. to 200° C. in the presence of a palladium-containing catalyst, wherein $R^{207}$, $R^{208}$ and $R^{209}$ are identical or different and are H or $C_1$-$C_6$alkyl, wherein two radicals optionally form a common ring and these radicals are optionally branched or unbranched. It must be ensured here that the totality of all monomers used has a highly balanced ratio of organotin functions to halogen functions. In addition, it may prove advantageous to remove any excess reactive groups at the end of the reaction by end-capping with monofunctional reagents. In order to carry out the process, the tin compounds and the halogen compounds are preferably introduced into one or more inert organic solvents and stirred at a temperature of from 0 to 200° C., preferably from 30 to 170° C. for a period of from 1 hour to 200 hours, preferably from 5 hours to 150 hours. The crude product can be purified by methods known to the person skilled in the art and appropriate for the respective polymer, for example repeated re-precipitation or even by dialysis.

Suitable organic solvents for the process described are, for example, ethers, for example diethyl ether, dimethoxyethane, diethylene glycol dimethyl ether, tetrahydrofuran, dioxane, dioxolane, diisopropyl ether and tert-butyl methyl ether, hydrocarbons, for example hexane, isohexane, heptane, cyclohexane, benzene, toluene and xylene, alcohols, for example methanol, ethanol, 1-propanol, 2-propanol, ethylene glycol, 1-butanol, 2-butanol and tert-butanol, ketones, for example acetone, ethyl methyl ketone and isobutyl methyl ketone, amides, for example dimethylformamide (DMF), dimethylacetamide and N-methylpyrrolidone, nitriles, for example acetonitrile, propionitrile and butyronitrile, and mixtures thereof.

The palladium and phosphine components should be selected analogously to the description for the Suzuki variant.

Alternatively, the polymers of the present invention can also be synthesized by the Negishi reaction using a zinc reagent A-$(ZnX^{12})_2$, wherein $X^{12}$ is halogen and halides, and $COM^1$-$(X^{23})_2$, wherein $X^{23}$ is halogen or triflate, or using A-$(X^{23})_2$ and $COM^1$-$(ZnX^{23})_2$. Reference is, for example, made to E. Negishi et al., Heterocycles 18 (1982) 117-22.

Alternatively, the polymers of the present invention can also be synthesized by the Hiyama reaction using a organo-silicon reagent A-$(SiR^{210}R^{211}R^{212})_2$, wherein $R^{210}$, $R^{211}$ and $R^{212}$ are identical or different and are halogen, or $C_1$-$C_6$alkyl, and $COM^1$-$(X^{23})_2$, wherein $X^{23}$ is halogen or triflate, or using A-$(X^{23})_2$ and $COM^1$-$(SiR^{210}R^{211}R^{212})_2$. Reference is, for example, made to T. Hiyama et al., Pure Appl. Chem. 66 (1994) 1471-1478 and T. Hiyama et al., Synlett (1991) 845-853.

Homopolymers of the type $(A)_n$ can be obtained via Yamamoto coupling of dihalides $X^{10}$-A-$X^{10}$, where $X^{10}$ is halogen, preferably Br. Alternatively homopolymers of the type $(A)_n$ can be obtained via oxidative polymerization of units $X^{10}$-A-$X^{10}$, where $X^{10}$ is hydrogen, e.g. with $FeCl_3$ as oxidizing agent.

A possible synthesis route for monomers useful in the preparation of polymers, comprising repeating units of formula (I), wherein $R^1$ and $R^2$ are the same and are an optionally substituted $C_6$-$C_{24}$aryl, or $C_2$-$C_{20}$heteroaryl group; is shown below:

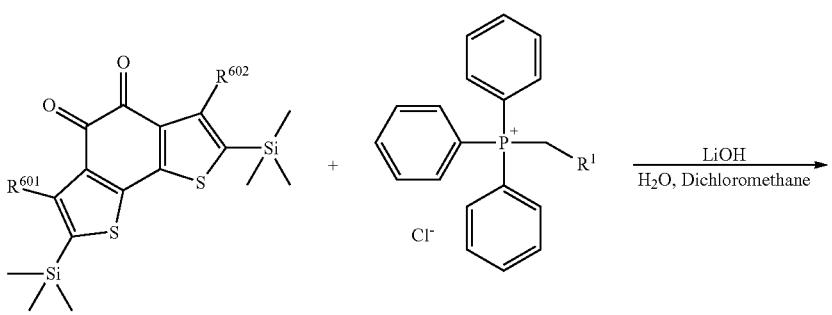

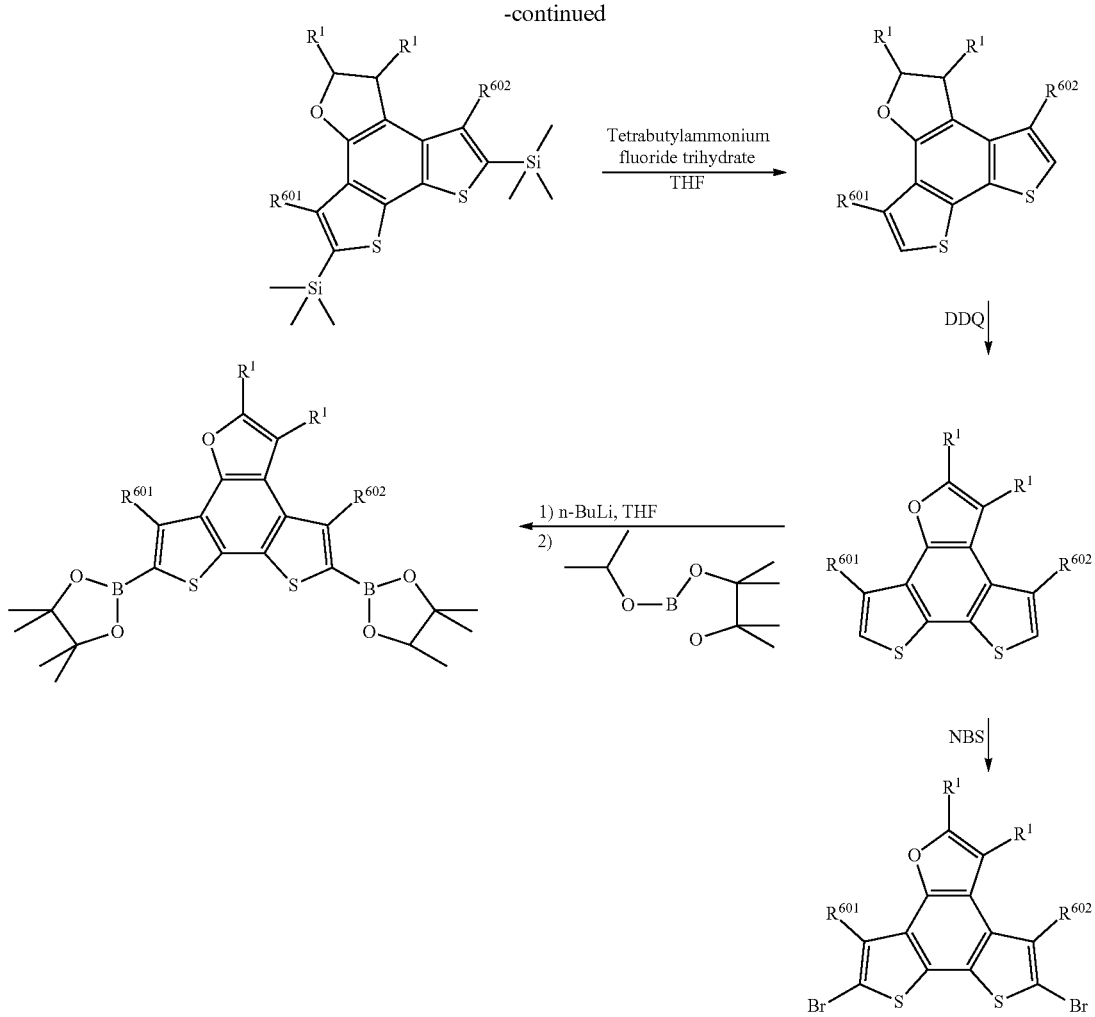
Compounds of formula (XVII) can be obtained by reacting compounds of formula (XX) with 1,4-dimethyl-piperazine-2,3-dione in the presence of butyl lithium in an appropriate solvent:
Compounds of formula (XVIII) can be obtained by reacting compounds of formula (XVII) with N-bromosuccinimide (NBS) in an appropriate solvent:
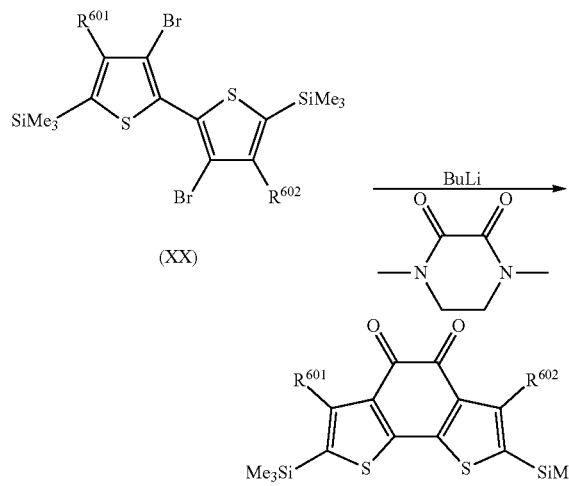
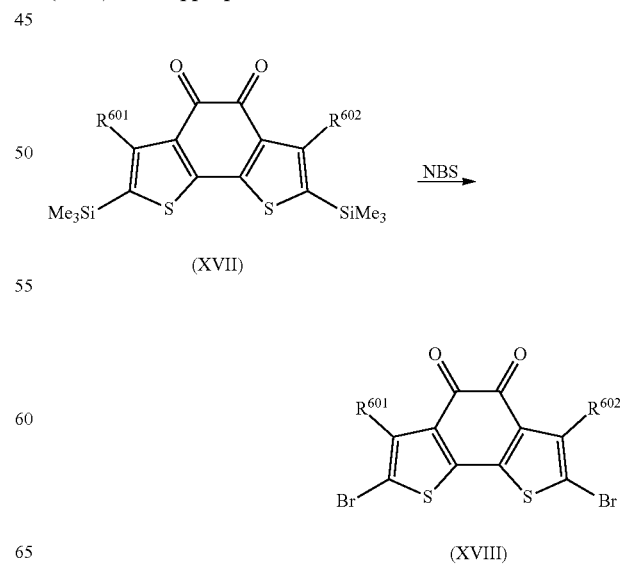

Intermediates for repeating units of formula (I), wherein $R^1$ and $R^2$ form together a group can be obtained by reacting compounds of formula (XVIII) with cyclohex-2-en-1-one in the presence of $TiCl_4$ in dichloromethane at elevated temperatures.

Reference is, for example, made to WO2009115413.

The compounds of formula (VIII) and (IX) can be prepared by using the above described intermediates and the synthesis methods described, for example, in WO2012175530 and WO2010/115767.

The compounds of the formula $$X^2-A^{1'}-A^3-Y-A^4-[Y^{15}-A^5]_p-[Y^{17}-A^{5'}]_q-A^{2'}-X^{2'}, \quad \text{or} \quad (IV)$$

$$X^2-A^{1'}-Y-A^3-Y^{15}-[A^4-Y^{16}]_p-[A^5-Y^{17}]_q-A^{2'}-X^{2'}, \quad (V)$$

are intermediates in the production of polymers, are new and form a further subject of the present invention. $A^{1'}$ and $A^{2'}$ are independently of each other a group of formula $$-[Ar^1]_a-[Ar^2]_b-[Ar^3]_c-,$$

wherein $X^2$ and $X^{2'}$ are independently of each other halogen, $ZnX^{12}$, $-SnR^{207}R^{208}R^{209}$, wherein $R^{207}$, $R^{208}$ and $R^{209}$ are identical or different and are H or $C_1$-$C_6$alkyl, wherein two radicals optionally form a common ring and these radicals are optionally branched or unbranched and $X^{12}$ is a halogen atom; or $-OS(O)_2CF_3$, $-OS(O)_2$-aryl, $-OS(O)_2CH_3$, $-B(OH)_2$, $-B(OY^1)_2$, $-BF_4Na$, or $-BF_4K$, wherein $Y^1$ is independently in each occurrence a $C_1$-$C_{10}$alkyl group and $Y^2$ is independently in each occurrence a $C_2$-$C_{10}$alkylene group, such as $-CY^3Y^4-CY^5Y^6-$, or $-CY^7Y^8-CY^9Y^{10}-CY^{11}Y^{12}-$, wherein $Y^3$, $Y^4$, $Y^5$, $Y^6$, $Y^7$, $Y^8$, $Y^9$, $Y^{10}$, $Y^{11}$ and $Y^{12}$ are independently of each other hydrogen, or a $C_1$-$C_{10}$alkyl group, especially $-C(CH_3)_2C(CH_3)_2-$, $-C(CH_3)_2CH_2C(CH_3)_2-$, or $-CH_2C(CH_3)_2CH_2-$; and $Y^{13}$ and $Y^{14}$ are independently of each other hydrogen, or a $C_1$-$C_{10}$alkyl group. a, b, c, p, q, $Ar^1$, $Ar^2$, $Ar^3$, Y, $Y^{15}$, $Y^{16}$, $Y^{17}$, $A^3$, $A^4$, $A^5$ and $A^{5'}$ are as defined above.

The compounds of the formula (IV), or (V) can be used in the production of polymers, comprising repeating unit(s) of formula $$-A^{1'}-Y-A^3-Y^{15}-[A^4-Y^{16}]_p-[A^5-Y^{17}]_q-A^{2'}-, \quad \text{or} \quad (Xa)$$

$$-A^{1'}-A^3-Y-A^4-[Y^{15}-A^5]_p-[Y^{17}-A^{5'}]_q-A^{2'}- \quad (Xb)$$

wherein
$A^{1'}$ and $A^{2'}$ are independently of each other a group of formula $$-[Ar^1]_a-[Ar^2]_b-[Ar^3]_c-,$$

wherein a, b, c, p, q, $Ar^1$, $Ar^2$, $Ar^3$, Y, $Y^{15}$, $Y^{16}$, $Y^{17}$, $A^3$, $A^4$, $A^5$ and $A^{5'}$ are as defined above.

Halogen is fluorine, chlorine, bromine and iodine.

The $C_1$-$C_{100}$alkyl group is preferably a $C_1$-$C_{38}$alkyl group, especially a $C_1$-$C_{25}$alkyl group. Reference is made to the definition of $R^{201}$.

$C_1$-$C_{25}$alkyl ($C_1$-$C_{18}$alkyl) is typically linear or branched, where possible. Examples are methyl, ethyl, n-propyl, isopropyl, n-butyl, sec.-butyl, isobutyl, tert.-butyl, n-pentyl, 2-pentyl, 3-pentyl, 2,2-dimethylpropyl, 1,1,3,3-tetramethylpentyl, n-hexyl, 1-methylhexyl, 1,1,3,3,5,5-hexamethylhexyl, n-heptyl, isoheptyl, 1,1,3,3-tetramethylbutyl, 1-methylheptyl, 3-methylheptyl, n-octyl, 1,1,3,3-tetramethylbutyl and 2-ethylhexyl, n-nonyl, decyl, undecyl, dodecyl, tridecyl, tetradecyl, pentadecyl, hexadecyl, heptadecyl, octadecyl, eicosyl, heneicosyl, docosyl, tetracosyl or pentacosyl. $C_1$-$C_8$alkyl is typically methyl, ethyl, n-propyl, isopropyl, n-butyl, sec.-butyl, isobutyl, tert.-butyl, n-pentyl, 2-pentyl, 3-pentyl, 2,2-dimethyl-propyl, n-hexyl, n-heptyl, n-octyl, 1,1,3,3-tetramethylbutyl and 2-ethylhexyl. $C_1$-$C_4$alkyl is typically methyl, ethyl, n-propyl, isopropyl, n-butyl, sec.-butyl, isobutyl, tert.-butyl.

$C_2$-$C_{25}$alkenyl ($C_2$-$C_{18}$alkenyl) groups are straight-chain or branched alkenyl groups, such as e.g. vinyl, allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, isododecenyl, n-dodec-2-enyl or n-octadec-4-enyl.

$C_2$-$C_{25}$alkynyl ($C_2$-$C_{18}$alkynyl) is straight-chain or branched and preferably $C_2$-$C_8$alkynyl, which may be unsubstituted or substituted, such as, for example, ethynyl, 1-propyn-3-yl, 1-butyn-4-yl, 1-pentyn-5-yl, 2-methyl-3-butyn-2-yl, 1,4-pentadiyn-3-yl, 1,3-pentadiyn-5-yl, 1-hexyn-6-yl, cis-3-methyl-2-penten-4-yn-1-yl, trans-3-methyl-2-penten-4-yn-1-yl, 1,3-hexadiyn-5-yl, 1-octyn-8-yl, 1-nonyn-9-yl, 1-decyn-10-yl, or 1-tetracosyn-24-yl.

A halogenated $C_1$-$C_{25}$alkyl group is a branched or unbranched radical, wherein all, or part of the hydrogen atoms of the corresponding alkyl group have been replaced by halogen atoms.

Aliphatic groups can, in contrast to aliphatic hydrocarbon groups, be substituted by any acyclic substituents, but are preferably unsubstituted. Preferred substituents are $C_1$-$C_8$alkoxy or $C_1$-$C_8$alkylthio groups as exemplified further below. The term "aliphatic group" comprises also alkyl groups wherein certain non-adjacent carbon atoms are replaced by oxygen, like $-CH_2-O-CH_2-CH_2-O-CH_3$. The latter group can be regarded as methyl substituted by $-O-CH_2-CH_2-O-CH_3$.

An aliphatic hydrocarbon group having up to 25 carbon atoms is a linear or branched alkyl, alkenyl or alkynyl (also spelled alkinyl) group having up to 25 carbon atoms as exemplified above.

Alkylene is bivalent alkyl, i.e. alkyl having two (instead of one) free valencies, e.g. trimethylene or tetramethylene.

Alkenylene is bivalent alkenyl, i.e. alkenyl having two (instead of one) free valencies, e.g. —CH$_2$—CH=CH—CH$_2$—.

Aliphatic groups can, in contrast to aliphatic hydrocarbon groups, be substituted by any acyclic substituents, but are preferably unsubstituted. Preferred substituents are C$_1$-C$_8$alkoxy or C$_1$-C$_8$alkylthio groups as exemplified further below. The term "aliphatic group" comprises also alkyl groups wherein certain non-adjacent carbon atoms are replaced by oxygen, like —CH$_2$—O—CH$_2$—CH$_2$—O—CH$_3$. The latter group can be regarded as methyl substituted by —O—CH$_2$—CH$_2$—O—CH$_3$.

A cycloaliphatic hydrocarbon group is a cycloalkyl or cycloalkenyl group which may be substituted by one or more aliphatic and/or cycloaliphatic hydrocarbon groups.

A cycloaliphatic-aliphatic group is an aliphatic group substituted by a cycloaliphatic group, wherein the terms "cycloaliphatic" and "aliphatic" have the meanings given herein and wherein the free valency extends from the aliphatic moiety. Hence, a cycloaliphatic-aliphatic group is for example a cycloalkyl-alkyl group.

A cycloalkyl-alkyl group is an alkyl group substituted by a cycloalkyl group, e.g. cyclohexyl-methyl.

A "cycloalkenyl group" means an unsaturated alicyclic hydrocarbon group containing one or more double bonds, such as cyclopentenyl, cyclopentadienyl, cyclohexenyl and the like, which may be unsubstituted or substituted by one or more aliphatic and/or cycloaliphatic hydrocarbon groups and/or condensed with phenyl groups.

A bivalent group of the formula IVb wherein R$^{28}$ and R$^{27}$ together represent alkylene or alkenylene which may be both bonded via oxygen and/or sulfur to the thienyl residue and which may both have up to 25 carbon atoms, is e.g. a group of the formula

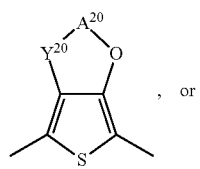, or (XXIX)

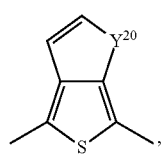, (XXX)

wherein A$^{20}$ represents linear or branched alkylene having up to 25 carbon atoms, preferably ethylene or propylene which may be substituted by one or more alkyl groups, and Y$^{20}$ represents oxygen or sulphur. For example, the bivalent group of the formula —Y$^{20}$-A$^{20}$-O— represents —O—CH$_2$—CH$_2$—O— or —O—CH$_2$—CH$_2$—CH$_2$—O—.

A group of the formula IVa wherein two groups R$^{22}$ to R$^{26}$ which are in the neighborhood of each other, together represent alkylene or alkenylene having up to 8 carbon atoms, thereby forming a ring, is e.g. a group of the formula

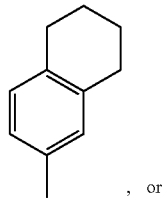, or (XXXII)

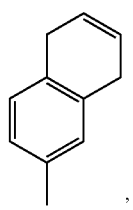, (XXXIII)

wherein in the group of the formula XXXII R$^{23}$ and R$^{24}$ together represent 1,4-butylene and in the group of the formula XXXIII R$^{23}$ and R$^{24}$ together represent 1,4-but-2-enylene.

The C$_1$-C$_{100}$alkoxy group is preferably a C$_1$-C$_{38}$alkoxy group, especially a C$_1$-C$_{25}$alkoxy group. C$_1$-C$_{25}$alkoxy groups (C$_1$-C$_{18}$alkoxy groups) are straight-chain or branched alkoxy groups, e.g. methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy. Examples of C$_1$-C$_8$alkoxy are methoxy, ethoxy, n-propoxy, isopropoxy, n-butoxy, sec.-butoxy, isobutoxy, tert.-butoxy, n-pentoxy, 2-pentoxy, 3-pentoxy, 2,2-dimethylpropoxy, n-hexoxy, n-heptoxy, n-octoxy, 1,1,3,3-tetramethylbutoxy and 2-ethylhexoxy, preferably C$_1$-C$_4$alkoxy such as typically methoxy, ethoxy, n-propoxy, isopropoxy, n-butoxy, sec.-butoxy, isobutoxy, tert.-butoxy. The term "alkylthio group" means the same groups as the alkoxy groups, except that the oxygen atom of the ether linkage is replaced by a sulfur atom.

C$_1$-C$_{18}$fluoroalkyl, especially C$_1$-C$_4$fluoroalkyl, is a branched or unbranched radical, wherein all, or part of the hydrogen atoms of the corresponding alkyl group have been replaced by fluorine atoms, such as for example —CF$_3$, —CF$_2$CF$_3$, —CF$_2$CF$_2$CF$_3$, —CF(CF$_3$)$_2$, —(CF$_2$)$_3$CF$_3$, and —C(CF$_3$)$_3$.

The term "carbamoyl group" is typically a C$_{1-18}$carbamoyl radical, preferably C$_{1-8}$carbamoyl radical, which may be unsubstituted or substituted, such as, for example, carbamoyl, methylcarbamoyl, ethylcarbamoyl, n-butylcarbamoyl, tert-butylcarbamoyl, dimethylcarbamoyloxy, morpholinocarbamoyl or pyrrolidinocarbamoyl.

A cycloalkyl group is typically C$_4$-C$_{18}$cycloalkyl, such as, for example, cyclopentyl, cyclohexyl, cycloheptyl, cyclooctyl, cyclononyl, cyclodecyl, cycloundecyl, cyclododecyl, preferably cyclopentyl, cyclohexyl, cycloheptyl, or cyclooctyl, which may be unsubstituted or substituted. The cycloalkyl group, in particular a cyclohexyl group, can be condensed one or two times by phenyl which can be substituted one to three times with $C_1$-$C_4$-alkyl, halogen and cyano. Examples of such condensed cyclohexyl groups are:

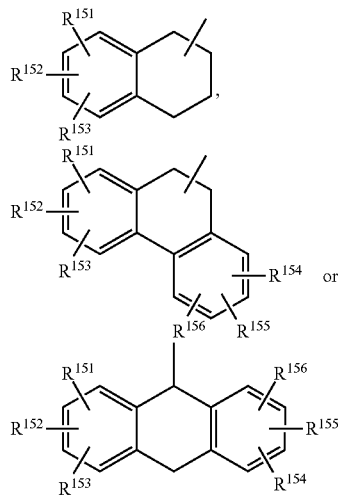

in particular

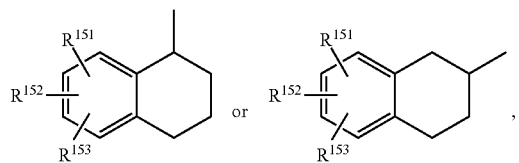

wherein $R^{151}$, $R^{152}$, $R^{153}$, $R^{154}$, $R^{155}$ and $R^{156}$ are independently of each other $C_1$-$C_8$-alkyl, $C_1$-$C_8$-alkoxy, halogen and cyano, in particular hydrogen.

$C_6$-$C_{24}$aryl ($C_6$-$C_{18}$aryl) is typically phenyl, indenyl, azulenyl, naphthyl, biphenyl, as-indacenyl, s-indacenyl, acenaphthylenyl, fluorenyl, phenanthryl, fluoranthenyl, triphenlenyl, chrysenyl, naphthacen, picenyl, perylenyl, pentaphenyl, hexacenyl, pyrenyl, or anthracenyl, preferably phenyl, 1-naphthyl, 2-naphthyl, 4-biphenyl, 9-phenanthryl, 2- or 9-fluorenyl, 3- or 4-biphenyl, which may be unsubstituted or substituted. Examples of $C_6$-$C_{12}$aryl are phenyl, 1-naphthyl, 2-naphthyl, 3- or 4-biphenyl, 2- or 9-fluorenyl or 9-phenanthryl, which may be unsubstituted or substituted.

$C_7$-$C_{25}$aralkyl is typically benzyl, 2-benzyl-2-propyl, β-phenyl-ethyl, α,α-dimethylbenzyl, ω-phenyl-butyl, ω,ω-dimethyl-ω-phenyl-butyl, ω-phenyl-dodecyl, ω-phenyl-octadecyl, ω-phenyl-eicosyl or ω-phenyl-docosyl, preferably $C_7$-$C_{18}$aralkyl such as benzyl, 2-benzyl-2-propyl, β-phenyl-ethyl, α,α-dimethylbenzyl, ω-phenyl-butyl, ω,ω-dimethyl-ω-phenyl-butyl, ω-phenyl-dodecyl or ω-phenyl-octadecyl, and particularly preferred $C_7$-$C_{12}$aralkyl such as benzyl, 2-benzyl-2-propyl, β-phenyl-ethyl, α,α-dimethylbenzyl, ω-phenyl-butyl, or ω,ω-dimethyl-ω-phenyl-butyl, in which both the aliphatic hydrocarbon group and aromatic hydrocarbon group may be unsubstituted or substituted. Preferred examples are benzyl, 2-phenylethyl, 3-phenylpropyl, naphthylethyl, naphthylmethyl, and cumyl.

Heteroaryl is typically $C_2$-$C_{20}$heteroaryl, i.e. a ring with five to seven ring atoms or a condensed ring system, wherein nitrogen, oxygen or sulfur are the possible hetero atoms, and is typically an unsaturated heterocyclic group with five to 30 atoms having at least six conjugated m-electrons such as thienyl, benzo[b]thienyl, dibenzo[b,d]thienyl, thianthrenyl, furyl, furfuryl, 2H-pyranyl, benzofuranyl, isobenzofuranyl, dibenzofuranyl, phenoxythienyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, chinolyl, isochinolyl, phthalazinyl, naphthyridinyl, chinoxalinyl, chinazolinyl, cinnolinyl, pteridinyl, carbazolyl, carbolinyl, benzotriazolyl, benzoxazolyl, phenanthridinyl, acridinyl, pyrimidinyl, phenanthrolinyl, phenazinyl, isothiazolyl, phenothiazinyl, isoxazolyl, furazanyl or phenoxazinyl, which can be unsubstituted or substituted.

Possible substituents of the above-mentioned groups are $C_1$-$C_8$alkyl, a hydroxyl group, a mercapto group, $C_1$-$C_8$alkoxy, $C_1$-$C_8$alkylthio, halogen, halo-$C_1$-$C_8$alkyl, a cyano group, a carbamoyl group, a nitro group or a silyl group, especially $C_1$-$C_8$alkyl, $C_1$-$C_8$alkoxy, $C_1$-$C_8$alkylthio, halogen, halo-$C_1$-$C_8$alkyl, or a cyano group.

$C_1$-$C_{25}$alkyl ($C_1$-$C_{18}$alkyl) interrupted by one or more O is, for example, $(CH_2CH_2O)_{1-9}$—$R^x$, where $R^x$ is H or $C_1$-$C_{10}$alkyl, $CH_2$—$CH(OR^{y'})$—$CH_2$—O—$R^y$, where $R^y$ is $C_1$-$C_{18}$alkyl, and $R^{y'}$ embraces the same definitions as $R^y$ or is H.

If a substituent, such as, for example $R^3$, occurs more than one time in a group, it can be different in each occurrence.

The present invention also relates to the use of the polymers, or compounds in an organic, electronic device.

The organic, electronic device is, for example, an organic electroluminescent device (OLED), a polymeric electroluminescent device (PLED), an organic integrated circuit (O-IC), an organic field-effect transistor (O-FET), an organic thin-film transistor (O-TFT), an organic light-emitting transistor (O-LET), an organic solar cell (O-SC), an organic optical detector, an organic photoreceptor, an organic field-quench device (O-FQD), a light-emitting electrochemical cell (LEC), or an organic laser diode (O-laser).

For the purposes of the present invention, it is preferred for the polymer, or compound according to the invention to be in the form of a layer (or to be present in a layer) in the electronic device. The polymer, or compound according to the invention can be present in the form of a hole-transport, hole-injection, emitter, electron-transport, electron-injection, charge-blocking and/or charge-generation layer. The polymers, or compounds according to the invention may be, for example, employed as emitting compounds in an emitting layer.

It may additionally be preferred to use the polymer not as the pure substance, but instead as a mixture (blend) together with further polymeric, oligomeric, dendritic or low-molecular-weight substances of any desired type. These may, for example, improve the electronic properties.

A mixture containing a polymer of the present invention results in a semi-conducting layer comprising a polymer of the present invention (typically 5% to 99.9999% by weight, especially 20 to 85% by weight) and at least another material. The other material can be, but is not restricted to a fraction of the same polymer of the present invention with different molecular weight, another polymer of the present invention, a semi-conducting polymer, organic small molecules, carbon nanotubes, a fullerene derivative, inorganic particles (quantum dots, quantum rods, quantum tripods, $TiO_2$, ZnO etc.), conductive particles (Au, Ag etc.), insulator materials like the ones described for the gate dielectric (PET, PS etc.). The polymers of the present invention can be blended with compounds of formula VIII, or IX according to the present invention, or small molecules described, for example, in WO2009/

047104, WO2010108873, WO09/047104, U.S. Pat. No. 6,690,029, WO2007082584, and WO2008107089:
WO2007082584:
(I1)
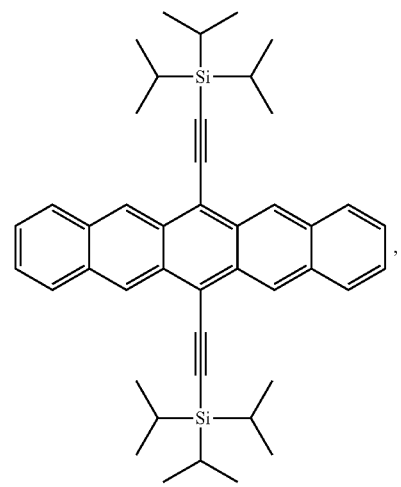
(I2)
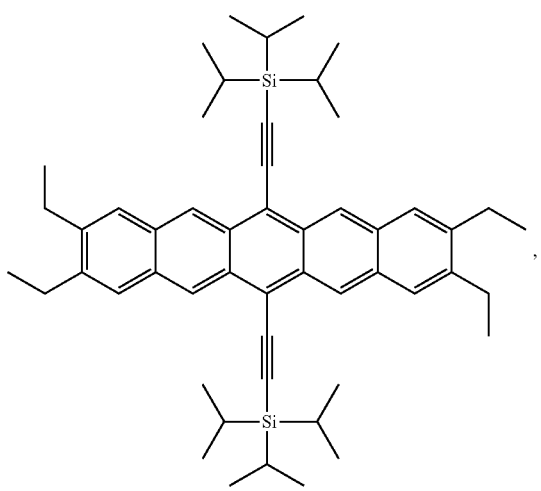
(I3)
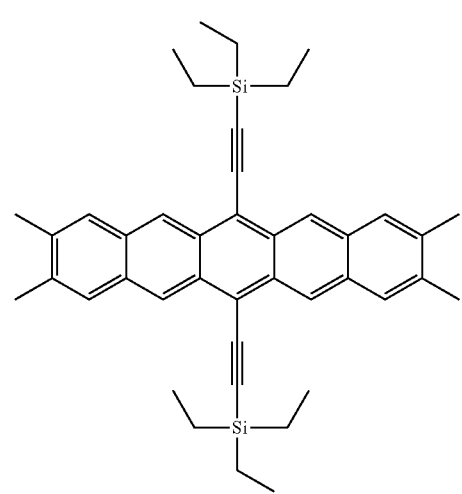
(I4)
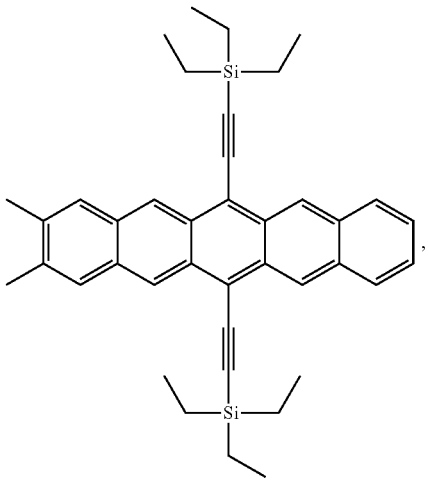
(I5)
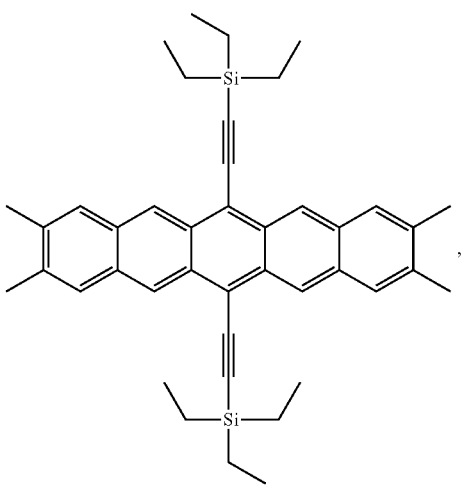
(I6)
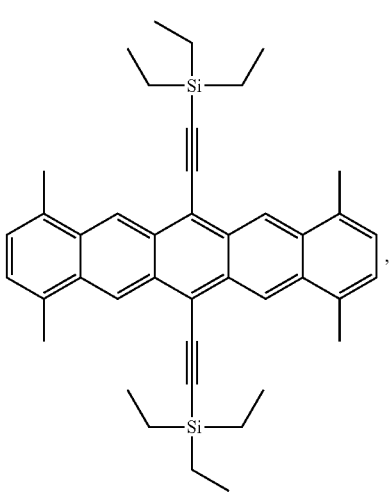

(I7)

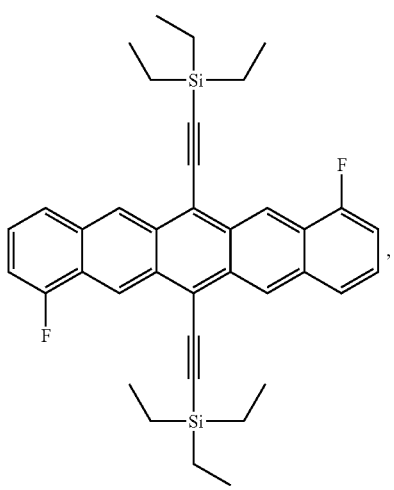

(I8)

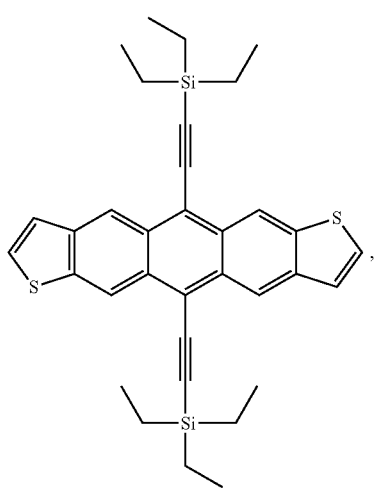

(I9)

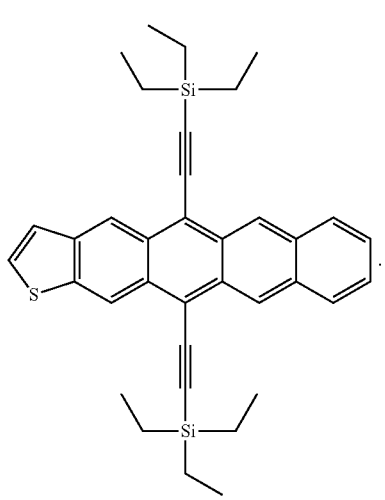

WO2008107089:

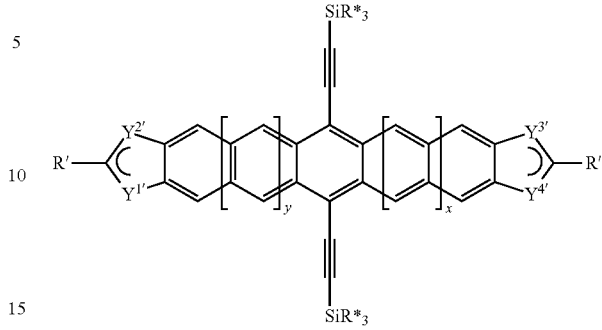

wherein one of $Y^{1'}$ and $Y^{2'}$ denotes —CH= or =CH— and the other denotes —X*—, one of $Y^{3'}$ and $Y^{4'}$ denotes —CH= or =CH— and the other denotes —X*—, X* is —O—, —S—, —Se— or —NR'''—, R* is cyclic, straight-chain or branched alkyl or alkoxy having 1 to 20 C-atoms, or aryl having 2-30 C-atoms, all of which are optionally fluorinated or perfluorinated, R' is H, F, Cl, Br, I, CN, straight-chain or branched alkyl or alkoxy having 1 to 20 C-atoms and optionally being fluorinated or perfluorinated, optionally fluorinated or perfluorinated aryl having 6 to 30 C-atoms, or $CO_2R''$, with R" being H, optionally fluorinated alkyl having 1 to 20 C-atoms, or optionally fluorinated aryl having 2 to 30 C-atoms, R''' is H or cyclic, straight-chain or branched alkyl with 1 to 10 C-atoms, y is 0, or 1, x is 0, or 1.

A1

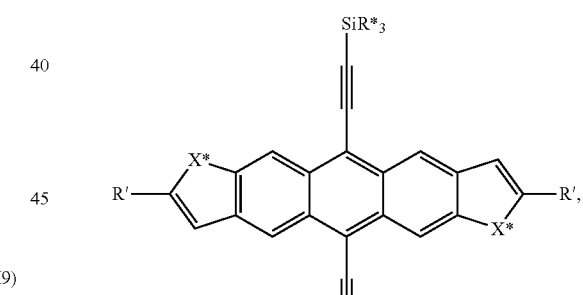

A2

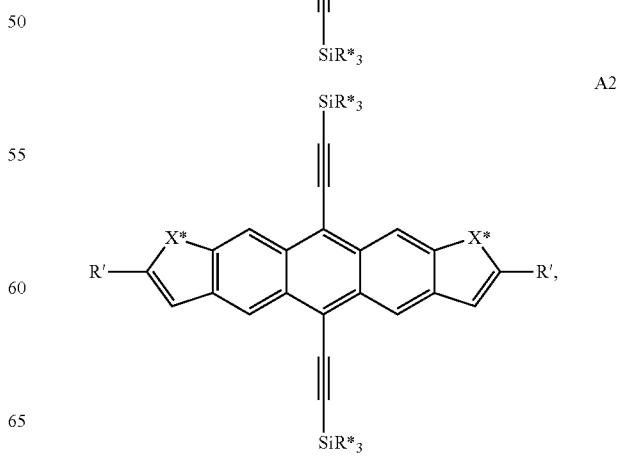

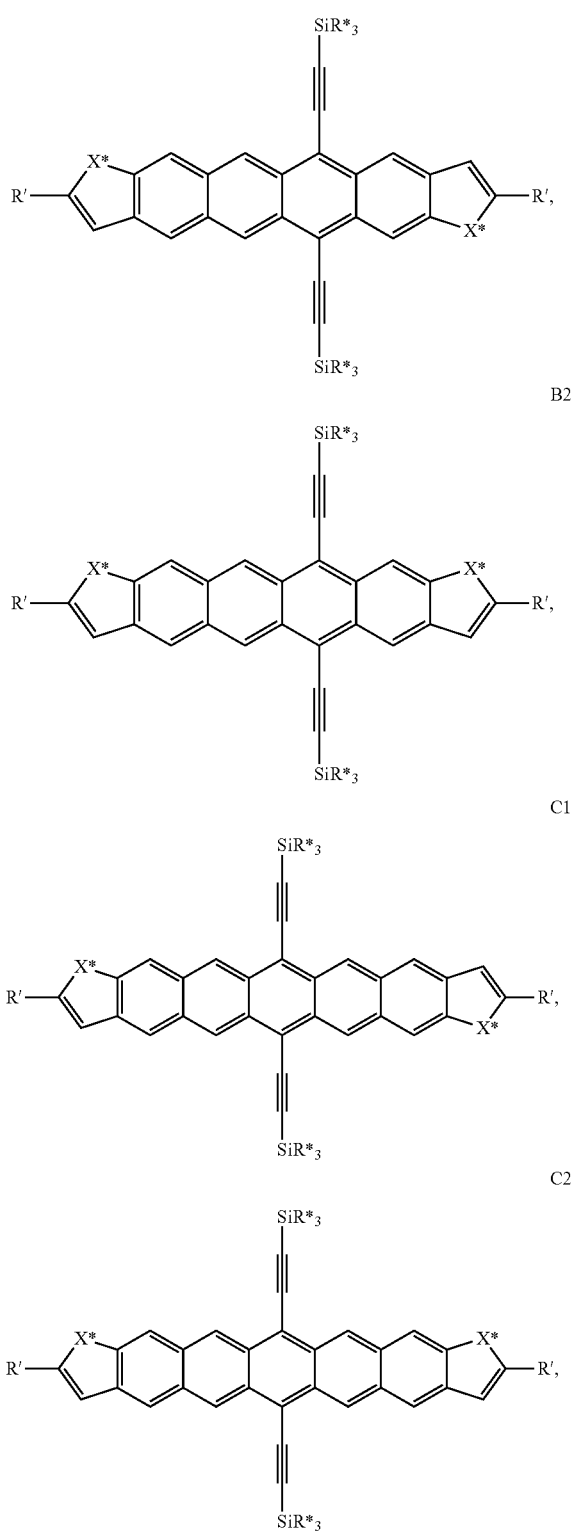

The polymer can contain a small molecule, or a mixture of two, or more small molecule compounds.

Accordingly, the present invention also relates to an organic semiconductor material, layer or component, comprising a polymer according to the present invention.

The polymers of the invention can be used as the semiconductor layer in semiconductor devices. Accordingly, the present invention also relates to semiconductor devices, comprising a polymer of the present invention, or an organic semiconductor material, layer or component. The semiconductor device is especially an organic photovoltaic (PV) device (solar cell), a photodiode, or an organic field effect transistor.

The polymers of the invention can be used alone or in combination as the organic semiconductor layer of the semiconductor device. The layer can be provided by any useful means, such as, for example, vapor deposition (for materials with relatively low molecular weight) and printing techniques. The compounds of the invention may be sufficiently soluble in organic solvents and can be solution deposited and patterned (for example, by spin coating, dip coating, ink jet printing, gravure printing, flexo printing, offset printing, screen printing, microcontact (wave)-printing, drop or zone casting, or other known techniques).

The polymers of the invention can be used in integrated circuits comprising a plurality of OTFTs, as well as in various electronic articles. Such articles include, for example, radio-frequency identification (RFID) tags, backplanes for flexible displays (for use in, for example, personal computers, cell phones, or handheld devices), smart cards, memory devices, sensors (e.g. light-, image-, bio-, chemo-, mechanical- or temperature sensors), especially photodiodes, or security devices and the like.

A further aspect of the present invention is an organic semiconductor material, layer or component comprising one or more polymers of the present invention. A further aspect is the use of the polymers or materials of the present invention in an organic photovoltaic (PV) device (solar cell), a photodiode, or an organic field effect transistor (OFET). A further aspect is an organic photovoltaic (PV) device (solar cell), a photodiode, or an organic field effect transistor (OFET) comprising a polymer or material of the present invention.

The polymers of the present invention are typically used as organic semiconductors in form of thin organic layers or films, preferably less than 30 microns thick. Typically the semiconducting layer of the present invention is at most 1 micron (=1 μm) thick, although it may be thicker if required. For various electronic device applications, the thickness may also be less than about 1 micron thick. For example, for use in an OFET the layer thickness may typically be 100 nm or less. The exact thickness of the layer will depend, for example, upon the requirements of the electronic device in which the layer is used.

For example, the active semiconductor channel between the drain and source in an OFET may comprise a layer of the present invention.

An OFET device according to the present invention preferably comprises:
a source electrode,
a drain electrode,
a gate electrode,
a semiconducting layer,
one or more gate insulator layers, and
optionally a substrate, wherein the semiconductor layer comprises one or more polymers of the present invention.

The gate, source and drain electrodes and the insulating and semiconducting layer in the OFET device may be arranged in any sequence, provided that the source and drain electrode are separated from the gate electrode by the insulating layer, the gate electrode and the semiconductor layer both contact the insulating layer, and the source electrode and the drain electrode both contact the semiconducting layer.

Preferably the OFET comprises an insulator having a first side and a second side, a gate electrode located on the first side of the insulator, a layer comprising a polymer of the present invention located on the second side of the insulator, and a drain electrode and a source electrode located on the polymer layer.

The OFET device can be a top gate device or a bottom gate device.

Suitable structures and manufacturing methods of an OFET device are known to the person skilled in the art and are described in the literature, for example in WO03/052841.

The gate insulator layer may comprise for example a fluoropolymer, like e.g. the commercially available Cytop 809M®, or Cytop 107M® (from Asahi Glass). Preferably the gate insulator layer is deposited, e.g. by spin-coating, doctor blading, wire bar coating, spray or dip coating or other known methods, from a formulation comprising an insulator material and one or more solvents with one or more fluoro atoms (fluorosolvents), preferably a perfluorosolvent. A suitable perfluorosolvent is e.g. FC75® (available from Acros, catalogue number 12380). Other suitable fluoropolymers and fluorosolvents are known in prior art, like for example the perfluoropolymers Teflon AF® 1600 or 2400 (from DuPont), or Fluoropel® (from Cytonix) or the perfluorosolvent FC 43® (Acros, No. 12377).

The semiconducting layer comprising a polymer of the present invention may additionally comprise at least another material. The other material can be, but is not restricted to another polymer of the present invention, a semi-conducting polymer, a polymeric binder, organic small molecules different from a polymer of the present invention, carbon nanotubes, a fullerene derivative, inorganic particles (quantum dots, quantum rods, quantum tripods, $TiO_2$, ZnO etc.), conductive particles (Au, Ag etc.), and insulator materials like the ones described for the gate dielectric (PET, PS etc.). As stated above, the semiconductive layer can also be composed of a mixture of one or more polymers of the present invention and a polymeric binder. The ratio of the polymers of the present invention to the polymeric binder can vary from 5 to 95 percent. Preferably, the polymeric binder is a semicrystalline polymer such as polystyrene (PS), high-density polyethylene (HDPE), polypropylene (PP) and polymethylmethacrylate (PMMA). With this technique, a degradation of the electrical performance can be avoided (cf. WO2008/001123A1).

The polymers of the present invention are advantageously used in organic photovoltaic (PV) devices (solar cells). Accordingly, the invention provides PV devices comprising a polymer according to the present invention. A device of this construction will also have rectifying properties so may also be termed a photodiode. Photoresponsive devices have application as solar cells which generate electricity from light and as photodetectors which measure or detect light.

The PV device comprise in this order:
 (a) a cathode (electrode),
 (b) optionally a transition layer, such as an alkali halogenide, especially lithium fluoride,
 (c) a photoactive layer,
 (d) optionally a smoothing layer,
 (e) an anode (electrode),
 (f) a substrate.

The photoactive layer comprises the polymers of the present invention. Preferably, the photoactive layer is made of a conjugated polymer of the present invention, as an electron donor and an acceptor material, like a fullerene, particularly a functionalized fullerene PCBM, as an electron acceptor. As stated above, the photoactive layer may also contain a polymeric binder. The ratio of the polymers of formula I to the polymeric binder can vary from 5 to 95 percent. Preferably, the polymeric binder is a semicristalline polymer such as polystyrene (PS), high-density polyethylene (HDPE), polypropylene (PP) and polymethylmethacrylate (PMMA).

For heterojunction solar cells the active layer comprises preferably a mixture of a polymer of the present invention and a fullerene, such as, for example, [60]PCBM (=6,6-phenyl-$C_{61}$-butyric acid methyl ester), or [70]PCBM, in a weight ratio of 1:1 to 1:3. The fullerenes useful in this invention may have a broad range of sizes (number of carbon atoms per molecule). The term fullerene as used herein includes various cage-like molecules of pure carbon, including Buckminsterfullerene ($C_{60}$) and the related "spherical" fullerenes as well as carbon nanotubes. Fullerenes may be selected from those known in the art ranging from, for example, $C_{20}$-$C_{1000}$. Preferably, the fullerene is selected from the range of $C_{69}$ to $C_{96}$. Most preferably the fullerene is $C_{69}$ or CM, such as [60]PCBM, or [70]PCBM. It is also permissible to utilize chemically modified fullerenes, provided that the modified fullerene retains acceptor-type and electron mobility characteristics. The acceptor material can also be a material selected from the group consisting of any semi-conducting polymer, such as, for example, a polymer of the present invention, provided that the polymers retain acceptor-type and electron mobility characteristics, organic small molecules, carbon nanotubes, inorganic particles (quantum dots, quantum rods, quantum tripods, $TiO_2$, ZnO etc.).

The photoactive layer is made of a polymer of the present invention as an electron donor and a fullerene, particularly functionalized fullerene PCBM, as an electron acceptor. These two components are mixed with a solvent and applied as a solution onto the smoothing layer by, for example, the spin-coating method, the drop casting method, the Langmuir-Blodgett ("LB") method, the ink jet printing method and the dripping method. A squeegee or printing method could also be used to coat larger surfaces with such a photoactive layer. Instead of toluene, which is typical, a dispersion agent such as chlorobenzene is preferably used as a solvent. Among these methods, the vacuum deposition method, the spin-coating method, the ink jet printing method and the casting method are particularly preferred in view of ease of operation and cost.

In the case of forming the layer by using the spin-coating method, the casting method and ink jet printing method, the coating can be carried out using a solution and/or dispersion prepared by dissolving, or dispersing the composition in a concentration of from 0.01 to 90% by weight in an appropriate organic solvent such as benzene, toluene, xylene, tetrahydrofurane, methyltetrahydrofurane, N,N-dimethylformamide, acetone, acetonitrile, anisole, dichloromethane, dimethylsulfoxide, chlorobenzene, 1,2-dichlorobenzene and mixtures thereof.

The photovoltaic (PV) device can also consist of multiple junction solar cells that are processed on top of each other in order to absorb more of the solar spectrum. Such structures are, for example, described in App. Phys. Let. 90, 143512 (2007), Adv. Funct. Mater. 16, 1897-1903 (2006) and WO2004/112161.

A so called 'tandem solar cell' comprise in this order:
 (a) a cathode (electrode),
 (b) optionally a transition layer, such as an alkali halogenide, especially lithium fluoride,
 (c) a photoactive layer,
 (d) optionally a smoothing layer,
 (e) a middle electrode (such as Au, Al, ZnO, $TiO_2$ etc.)

(f) optionally an extra electrode to match the energy level,
(g) optionally a transition layer, such as an alkali halogenide, especially lithium fluoride,
(h) a photoactive layer,
(i) optionally a smoothing layer,
(j) an anode (electrode),
(k) a substrate.

The PV device can also be processed on a fiber as described, for example, in US20070079867 and US 20060013549.

Due to their excellent self-organising properties the materials or films comprising the polymers of the present invention can also be used alone or together with other materials in or as alignment layers in LCD or OLED devices, as described for example in US2003/0021913.

It is another object of the present invention to provide compounds, which show high efficiency of energy conversion, excellent field-effect mobility, good on/off current ratios and/or excellent stability, when used in organic field effect transistors, organic photovoltaics (solar cells) and photodiodes.

In a further embodiment the present invention relates to compounds of the formula

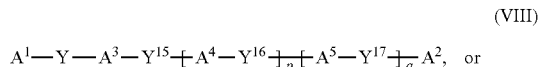
(VIII)

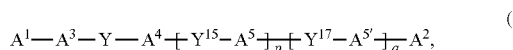
(IX)

wherein Y, $Y^{15}$, $Y^{16}$ and $Y^{17}$ are independently of each other a group of formula

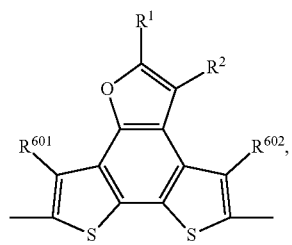
(I)

wherein $R^1$, $R^2$, $R^{601}$ and $R^{602}$ are as defined above,
p is 0, or 1, q is 0, or 1;
$A^1$ and $A^2$ are independently of each other a group of formula

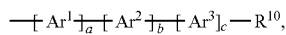

a is 0, 1, 2, or 3; b is 0, 1, 2, or 3; c is 0, 1, 2, or 3;
$A^3$, $A^4$, $A^5$ and $A^{5'}$ are independently of each other a group of formula

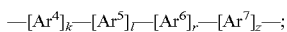

k' is 0, 1, 2, or 3; l is 0, 1, 2, or 3; r is 0, 1, 2, or 3; z is 0, 1, 2, or 3;
$R^{10}$ is hydrogen, halogen, cyano, $C_1$-$C_{25}$alkyl, $C_1$-$C_{25}$alkyl which is substituted one or more times by E" and/or interrupted one or more times by D",

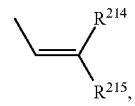

COO—$C_1$-$C_{18}$alkyl, $C_4$-$C_{18}$cycloalkyl group, $C_4$-$C_{18}$cycloalkyl group, which is substituted by G", $C_2$-$C_{18}$alkenyl, $C_2$-$C_{18}$alkynyl, $C_1$-$C_{18}$thioalkoxy, $C_1$-$C_{18}$alkoxy, $C_1$-$C_{18}$alkoxy which is substituted by E" and/or interrupted by D", $C_7$-$C_{25}$aralkyl, $C_7$-$C_{25}$aralkyl, which is substituted by G", or a group of formulae IVa to IVm,

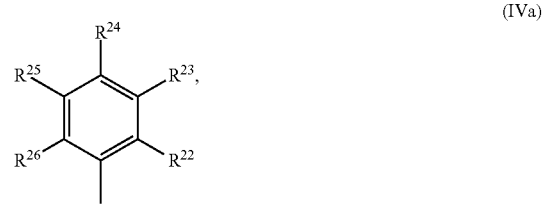
(IVa)

(IVb)

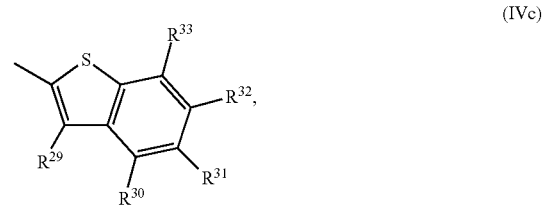
(IVc)

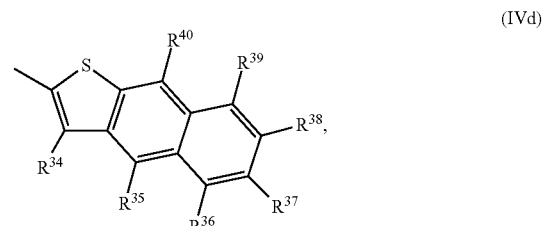
(IVd)

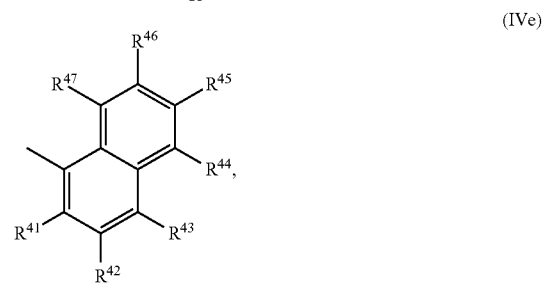
(IVe)

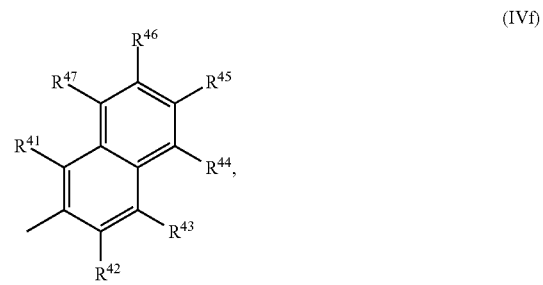
(IVf)

-continued (IVg) 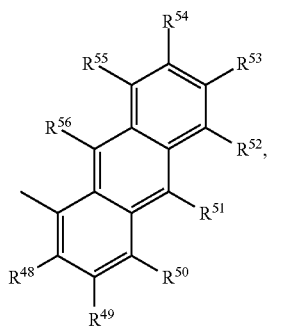

(IVh) 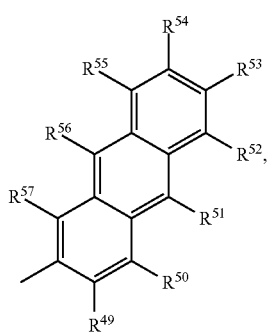

(IVi) 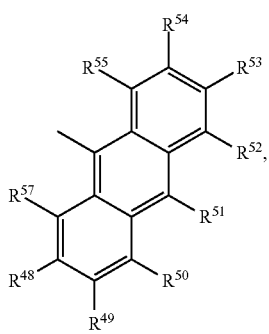

(IVj) 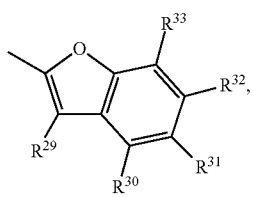

(IVk) 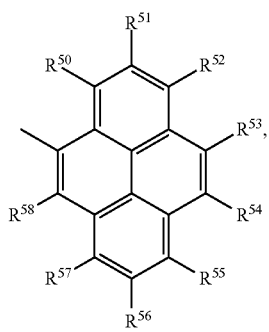

(IVl) 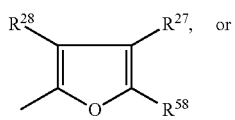, or (IVm) 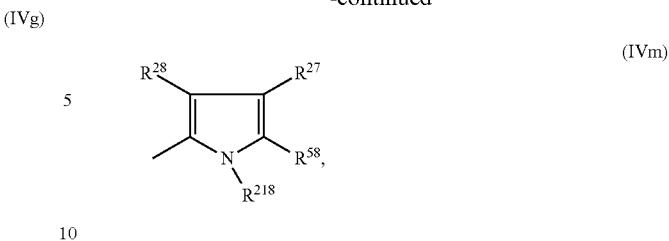

wherein $R^{22}$ to $R^{26}$ and $R^{29}$ to $R^{58}$ represent independently of each other H, halogen, cyano, $C_1$-$C_{25}$alkyl, $C_1$-$C_{25}$alkyl which is substituted by E″ and/or interrupted by D″, $C_6$-$C_{24}$aryl, $C_6$-$C_{24}$aryl which is substituted by G″, $C_2$-$C_{20}$heteroaryl, $C_2$-$C_{20}$heteroaryl which is substituted by G″, a $C_4$-$C_{18}$cycloalkyl group, a $C_4$-$C_{18}$cycloalkyl group, which is substituted by G″, $C_2$-$C_{18}$alkenyl, $C_2$-$C_{18}$alkynyl, $C_1$-$C_{18}$alkoxy, $C_1$-$C_{18}$alkoxy which is substituted by E″ and/or interrupted by D″, $C_7$-$C_{25}$aralkyl, or $C_7$-$C_{25}$aralkyl, which is substituted by G″, $R^{27}$ and $R^{28}$ are independently of each other hydrogen, $C_1$-$C_{25}$alkyl, halogen, cyano or $C_7$-$C_{25}$aralkyl, or $R^{27}$ and $R^{28}$ together represent alkylene or alkenylene which may be both bonded via oxygen and/or sulfur to the thienyl residue and which may both have up to 25 carbon atoms, $R^{59}$ is hydrogen, $C_6$-$C_{18}$aryl; $C_6$-$C_{18}$aryl which is substituted by $C_1$-$C_{18}$alkyl, or $C_1$-$C_{18}$alkoxy; or $C_1$-$C_{25}$alkyl, which may optionally be interrupted by one or more oxygen or sulphur atoms; or $C_7$-$C_{25}$arylalkyl, D″ is —CO—, —COO—, —S—, —O—, or $NR^{112″}$—, E″ is $C_1$-$C_8$thioalkoxy, $C_1$-$C_8$alkoxy, CN, —$NR^{112″}R^{113″}$, —$CONR^{112″}R^{113″}$, or halogen, G″ is E″, or $C_1$-$C_{18}$alkyl, and $R^{112″}$ and $R^{113″}$ are independently of each other H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—;

$R^{214}$ and $R^{215}$ are independently of each other hydrogen, $C_1$-$C_{18}$alkyl, $C_6$-$C_{24}$aryl, $C_2$-$C_{20}$heteroaryl, —CN or $COOR^{216}$;

$R^{216}$ is $C_1$-$C_{25}$alkyl, $C_1$-$C_{25}$haloalkyl, $C_7$-$C_{25}$arylalkyl, $C_6$-$C_{24}$aryl or $C_2$-$C_{20}$heteroaryl;

$R^{218}$ is hydrogen, $C_6$-$C_{18}$aryl; $C_6$-$C_{18}$aryl which is substituted by $C_1$-$C_{18}$alkyl, or $C_1$-$C_{18}$alkoxy; or $C_1$-$C_{25}$alkyl, which may optionally be interrupted by one or more oxygen or sulphur atoms; or $C_7$-$C_{25}$arylalkyl, $Ar^1$, $Ar^2$, $Ar^3$ $Ar^4$, $Ar^5$, $Ar^6$ and $Ar^7$ are independently of each other a group of formula (XIa), (XIb), (XIc), (XId), (XIe), (XIf), (XIg), (XIh), (XIi), (XIj), (XIk), (XIl), (XIm), (XIn), (XIo), (XIpa), (XIpb), (XIq), (XIr), (XIs), (XIt), (XIu), (XIv), (XIw), (XIx), (XIy), (XIz), (XIIa), (XIIb), (XIIc), (XIId), (XIIe), (XIIf), (XIIg), (XIIh), (XIIi), (XIIj), (XIIk), (XIII), such as, for example, (XIIIa), (XIIIb), (XIIIc), (XIIId), (XIIIe), (XIIIf), (XIIIg), (XIIIh), (XIIIi), (XIIIj), (XIIIk), and (XIIIl); or (XIV), such as, for example, (XIVa); (XVa), (XVb), (XVc), (XVd), (XVe), (XVf), (XVg), (XVh), (XVi), (XVj), (XVk), (XVl), (XVm), (XVn), (XVo), (XVp), (XVq), (XVr), (XVs), such as, for example, (XVsa), (XVsb), and (XVsc); (XVt), such as, for example, (XVta), (XVtb), and (XVuc), and (XVu).

The structure represented by formula

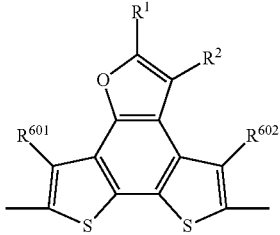
(I)

can be bonded in two ways to the groups of formula A³, A⁴, A⁵ and A⁵':

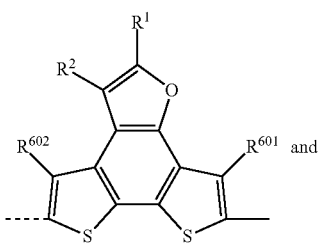
and
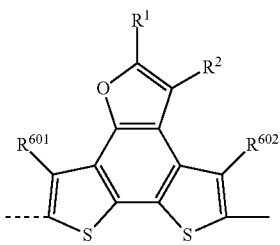

(the dotted line represents the bonding to the groups of formula A³, A⁴, A⁵ and A⁵'). Both possibilities shall be covered by formula (I).

Preferably, the compound is a compound of the formula A¹-Y-A³-Y¹⁵-A² (VIIIa), A¹-Y-A³-Y¹⁵-A⁴-Y¹⁶-A² (VIIIb), or A¹-Y-A³-Y¹⁵-A⁴-Y¹⁶-A⁵-Y¹⁷-A² (VIIIc), A¹-A³-Y-A⁴-A² (IXa), A¹-A³-Y-A⁴-Y¹⁵-A⁵-A² (IXb), or A¹-A³-Y-A⁴-Y₁₅-A⁵-Y¹⁷-A⁵'-A² (IXc), wherein Y, Y¹⁵, Y¹⁶ and Y¹⁷ are independently of each other a group of formula

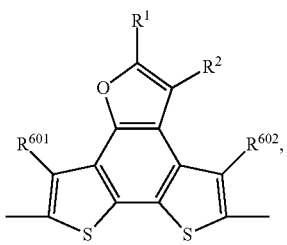
(I)

wherein R¹ and R² are independently of each other a group of formula

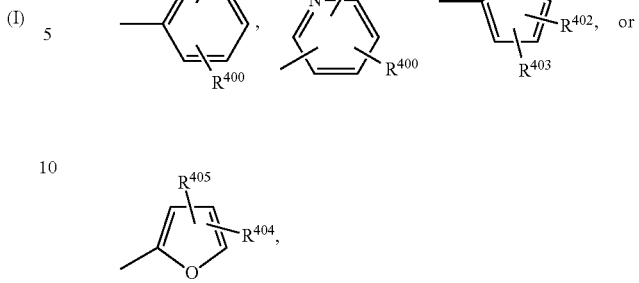

wherein $R^{400}$, $R^{401}$, $R^{402}$, $R^{403}$, $R^{404}$ and $R^{405}$ are independently of each other H, CN, F, CF₃, C₁-C₁₈alkoxy; C₁-C₁₈alkyl; or C₁-C₁₈alkyl which is interrupted by —O—, or R¹ and R² form together a group

and $R^{601}$ and $R^{602}$ are independently of each other hydrogen, or C₁-C₂₅ alkyl, especially hydrogen.

A¹ and A² are as defined above,

A³, A⁴, A⁵ and A⁵' are independently of each other a group of formula

(XIa)

(XId)

(XIh)

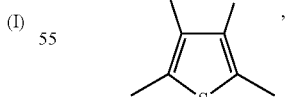

(XIi)

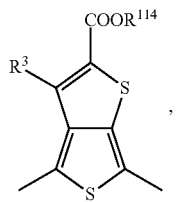

-continued (XIIIh)
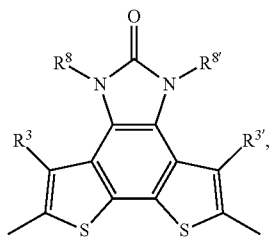

(XVb)
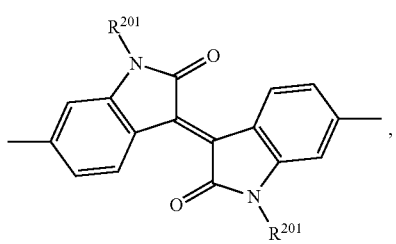

(XVb')
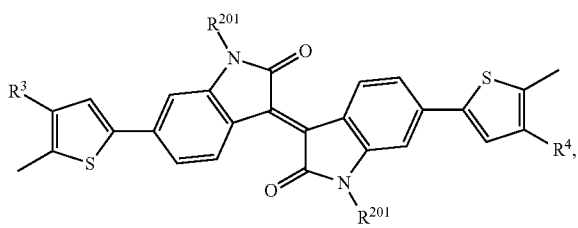

(XVe)
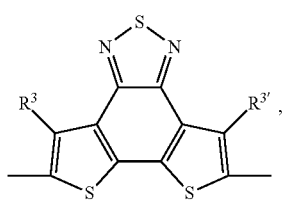

(XVh')
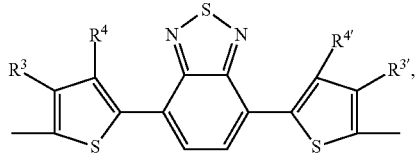

(XVh)
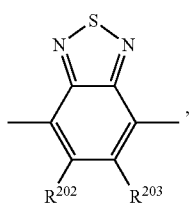

-continued (XVu')
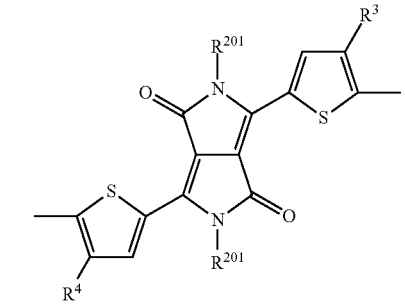

, (XVu'')
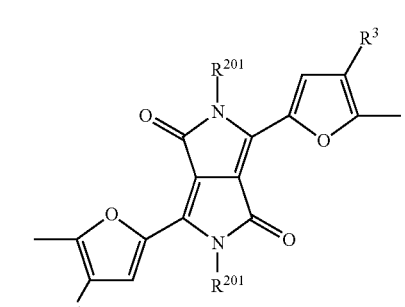

, or (XVu''')
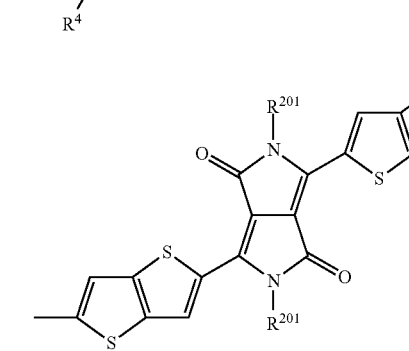

;

wherein
$R^3$, $R^{3'}$, $R^4$ and $R^{4'}$ are independently of each other hydrogen, or $C_1$-$C_{25}$alkyl;
$R^8$ and $R^{8'}$ are independently of each other hydrogen, or $C_1$-$C_{25}$alkyl;
$R^{114}$ is a $C_1$-$C_{38}$alkyl group;
$R^{201}$ is a $C_1$-$C_{38}$alkyl group; and
$R^{202}$ and $R^{203'}$ are independently of each other hydrogen or $C_1$-$C_{25}$alkyl.
$R^1$ and $R^2$ are especially a group of formula

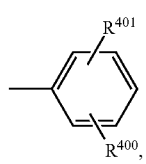

very especially a group of formula

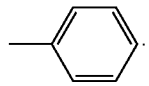

$R^1$ and $R^2$ may be the same, but are preferably the same.

The group of formula (I) is preferably a group of formula

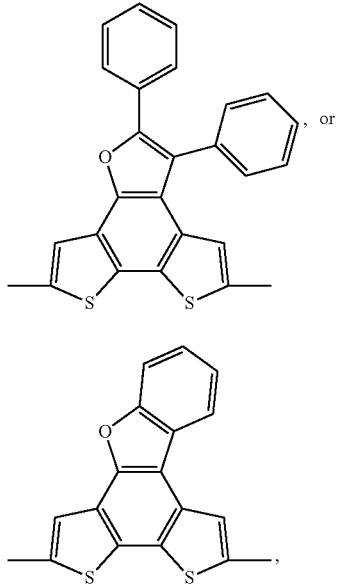

especially (Ia).

In a preferred embodiment $A^3$, $A^4$, $A^5$ and $A^{5'}$ are independently of each other a group of formula (XVb), (XVb'), (XVh), (XVh'), (XVi), (XVi'), (XVu'), (XVu''), and (XVu'''). In a particularly preferred embodiment $A^3$, $A^4$, $A^5$ and $A^{5'}$ are selected from groups of formula (XVb), (XVc), (XVu'), (XVu''), and (XVu''').

In a preferred embodiment of the present invention $A^1$ and $A^2$ are independently of each other a group of formula H,

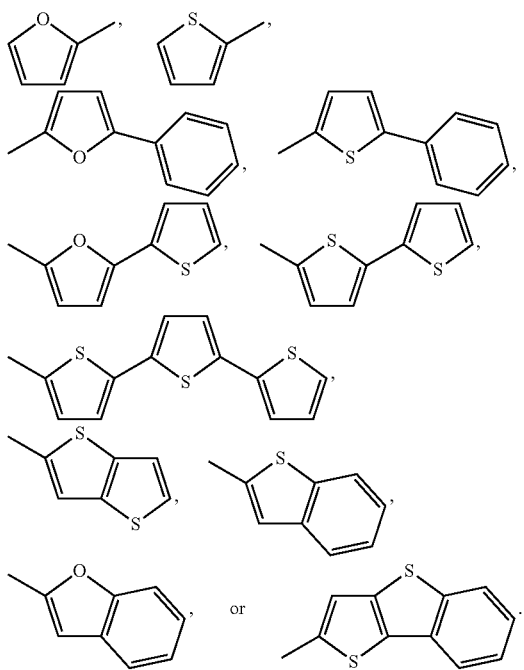

In a preferred embodiment the present invention is directed to compounds of formula $A^1$-$A^3$-Y-$A^4$-$A^2$ (IXa), wherein Y is a group of formula

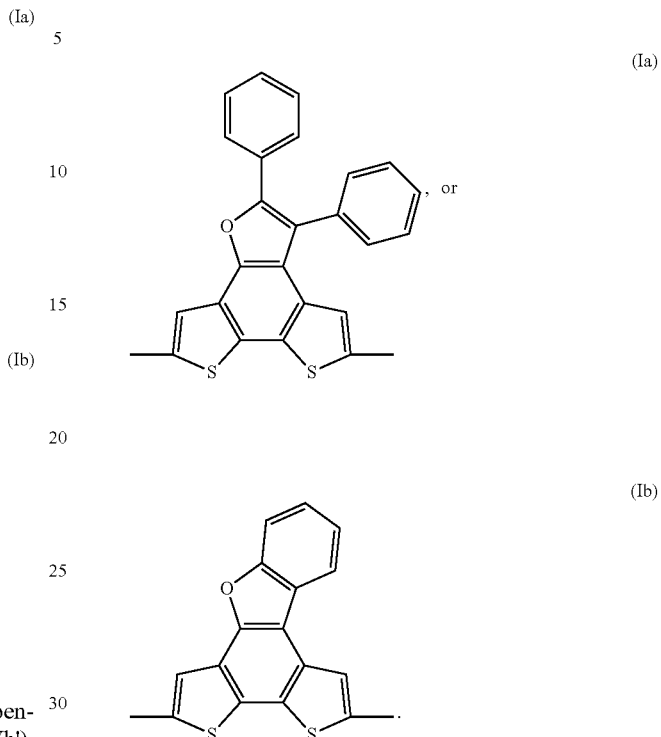

In said embodiment $A^1$-$A^3$- and $A^4$-$A^2$- are a group of formula:
i)

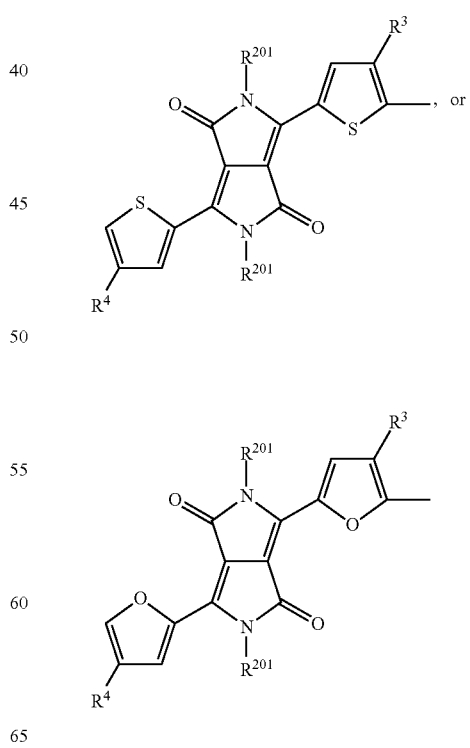

($R^3$ and $R^4$ may be different, but are preferably the same and are H, or $C_1$-$C_{25}$alkyl; $R^{201}$ is a $C_1$-$C_{38}$alkyl group);

ii)
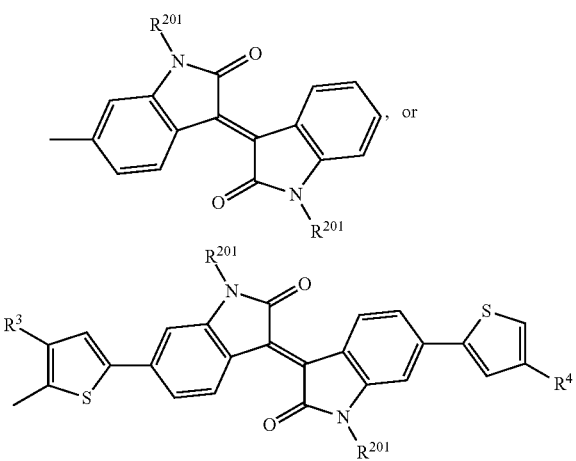
(R³ and R⁴ may be different, but are preferably the same and are H, or $C_1$-$C_{25}$alkyl; $R^{201}$ is a $C_1$-$C_{38}$alkyl group);
iii)
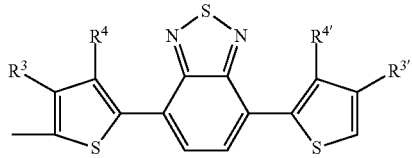
(R³ and R³' may be different, but are preferably the same and are H, or $C_1$-$C_{25}$alkyl; R⁴ and R⁴' may be different, but are preferably the same and are H, or $C_1$-$C_{25}$alkyl).
Examples of particular preferred compounds of formula IX are shown below:
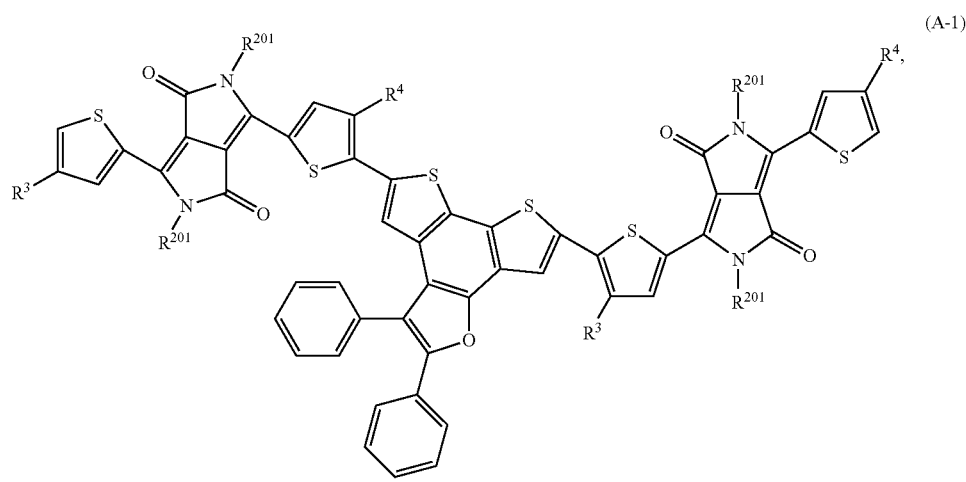
(A-1)
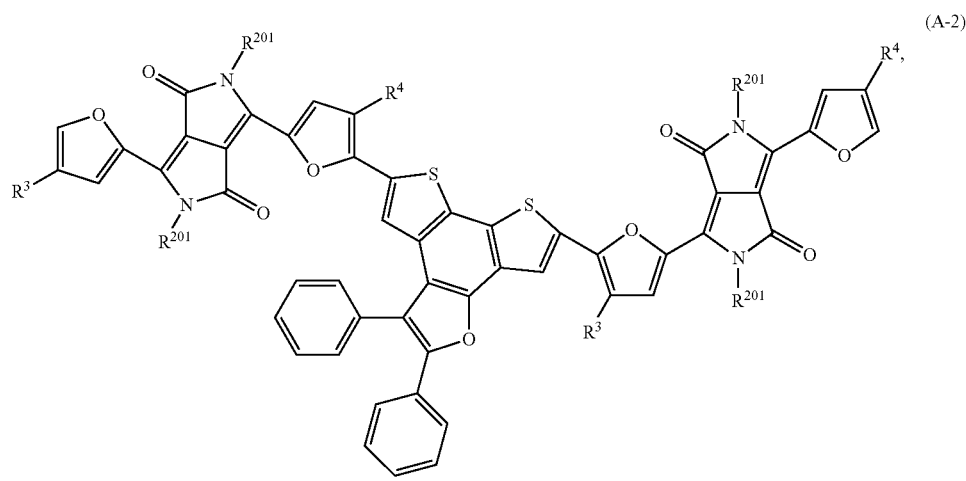
(A-2)

-continued
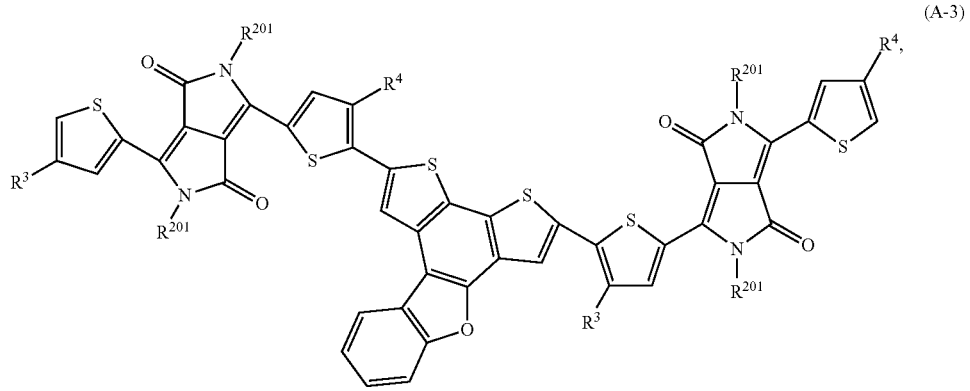
(A-3)
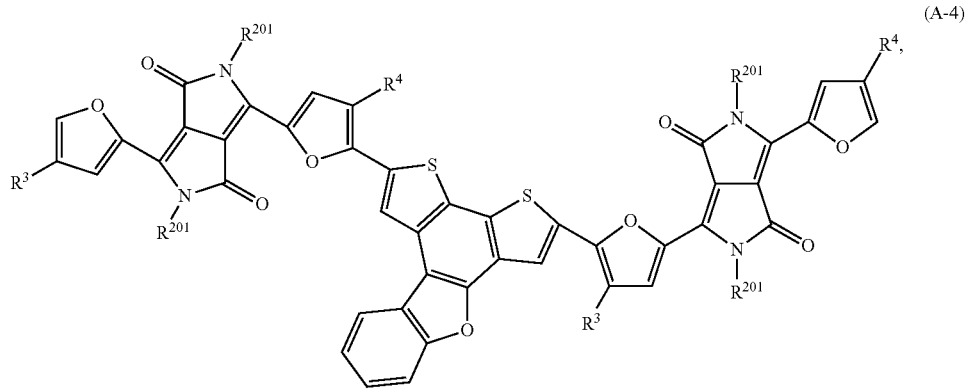
(A-4)
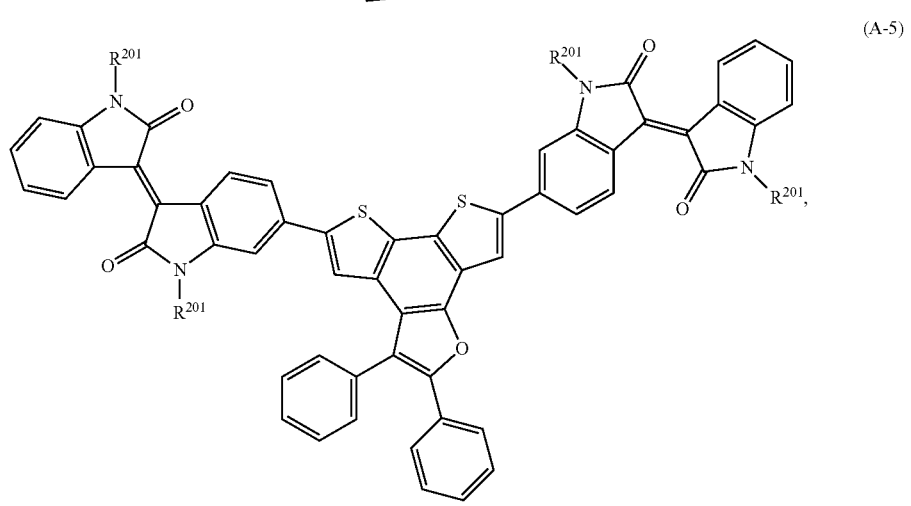
(A-5)
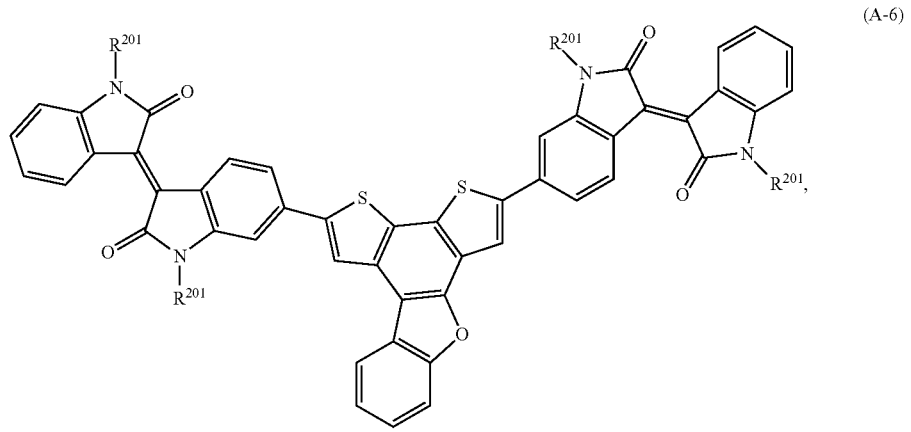
(A-6)

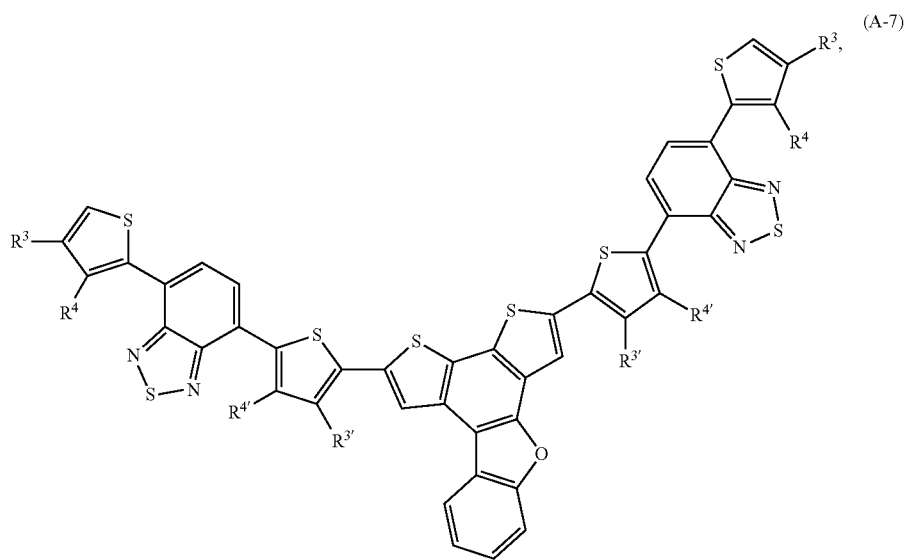
(A-7)
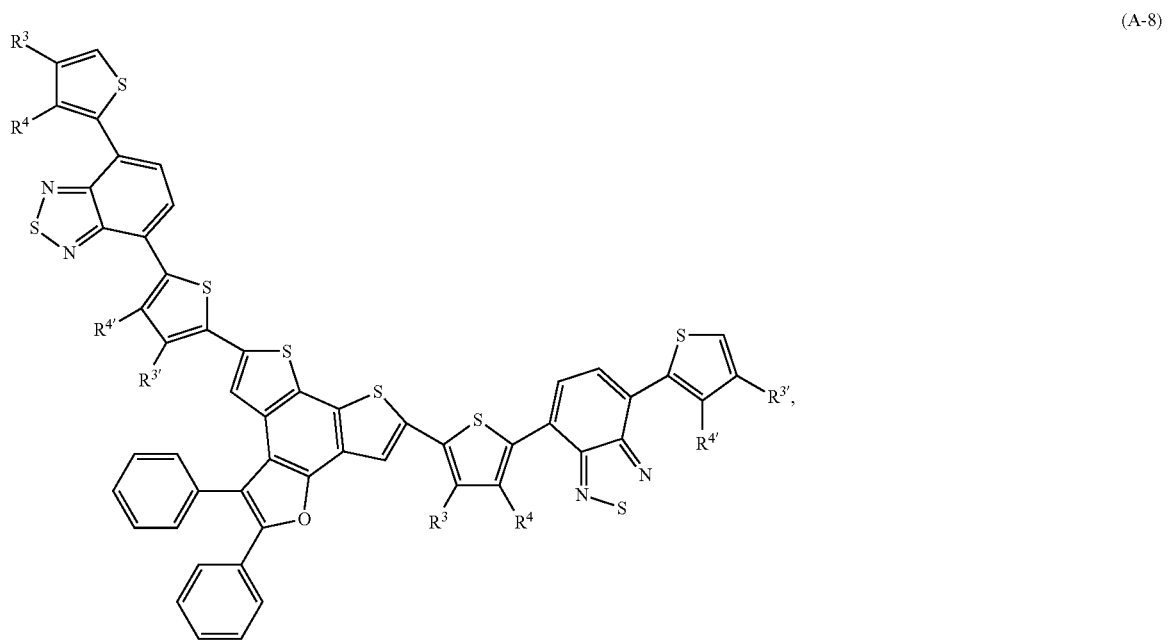
(A-8)

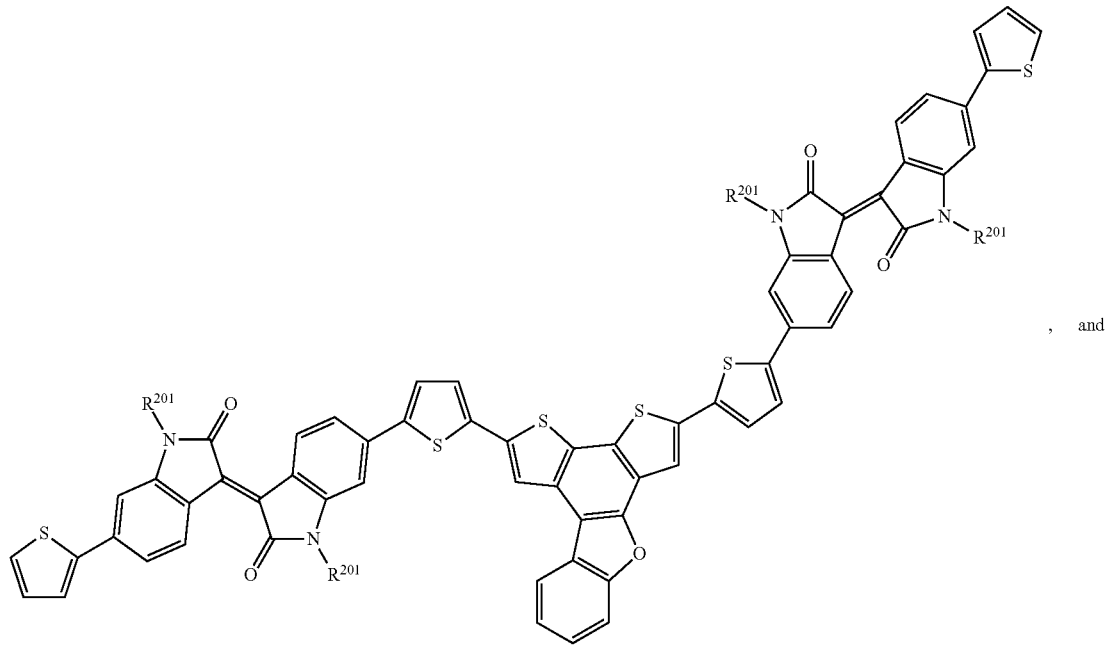

(A-10)

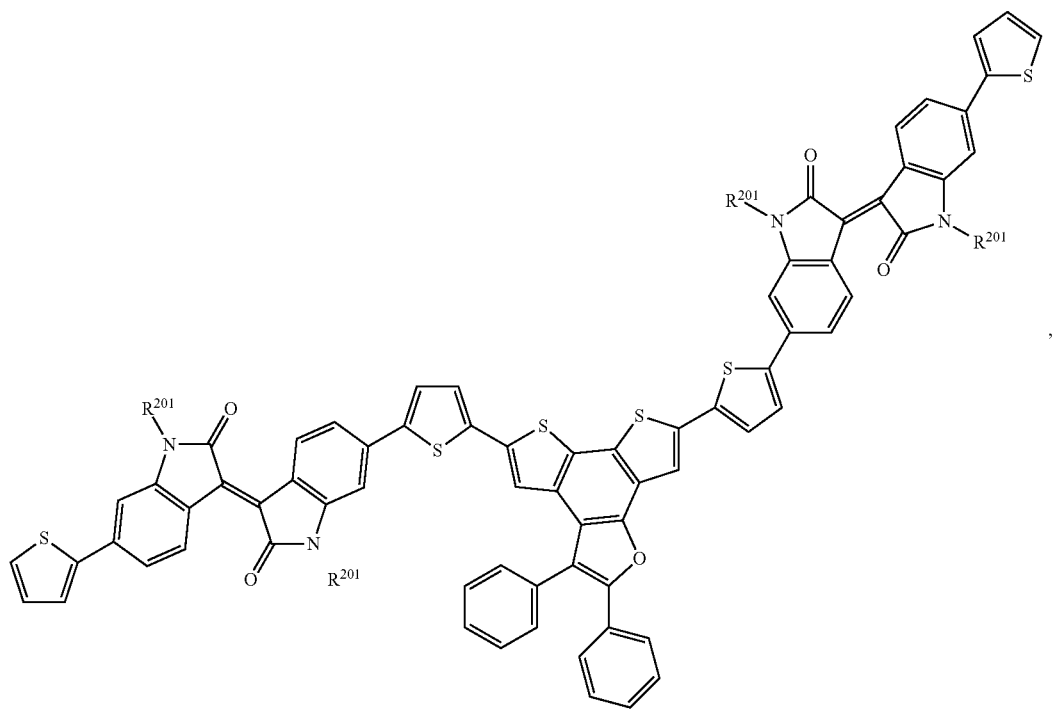

(A-11)

wherein $R^3$, $R^{3'}$, $R^4$ and $R^{4'}$ are independently of each other hydrogen or $C_1$-$C_{25}$alkyl; and $R^{201}$ is a $C_1$-$C_{38}$alkyl group. $R^3$, $R^{3'}$, $R^4$ and $R^{4'}$ are preferably hydrogen.

Compounds A-1, A-2, A-5 and A-11 are most preferred.

$A^1$-$A^3$-Y-$A^3$-$A^1$ (IXa) may be prepared by reacting a compound of formula $A^1$-$A^3$-$X^{16}$ with a compound of formula $X^{16'}$—Y—$X^{16'}$, $X^{16'}$ is —B(OH)$_2$, —B(OH)$_3^-$, —BF$_3$, —B(OY$^1$)$_2$,

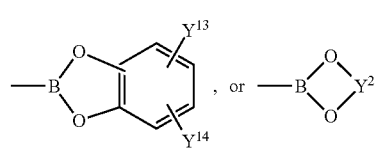

and $X^{16}$ is halogen, such as, for example, Br, or I.

The Suzuki reaction is typically conducted at about 0° C. to 180° C. in an aromatic hydrocarbon solvent such as toluene, xylene. Other solvents such as dimethylformamide, dioxane, dimethoxyethan and tetrahydrofuran can also be used alone, or in mixtures with an aromatic hydrocarbon. An aqueous base, preferably sodium carbonate or bicarbonate, potassium phosphate, potassium carbonate or bicarbonate is used as activation agent for the boronic acid, boronate and as the HBr scavenger. A condensation reaction may take 0.2 to 100 hours. Organic bases, such as, for example, tetraalkylammonium hydroxide, and phase transfer catalysts, such as, for example TBAB, can promote the activity of the boron (see, for example, Leadbeater & Marco; Angew. Chem. Int. Ed. Eng. 42 (2003) 1407 and references cited therein). Other variations of reaction conditions are given by T. I. Wallow and B. M. Novak in J. Org. Chem. 59 (1994) 5034-5037; and M. Remmers, M. Schulze, and G. Wegner in Macromol. Rapid Commun. 17 (1996) 239-252.

In the above Suzuki coupling reactions the halogen $X^{16}$ on the halogenated reaction partner can be replaced with the $X^{16'}$ moiety and at the same time the $X^{16'}$ moiety of the other reaction partner is replaced by $X^{16}$.

The synthesis of the corresponding diketopyrrolopyrrole intermediates is, for example, described in R. A. J. Janssen et al., Macromol. Chem. Phys. 2011, 212, 515-520, US2010/0326225 and EP11179840.1.

Accordingly, the present invention also relates to an organic semiconductor material, layer or component, comprising a compound of formula VIII, or IX and to a semiconductor device, comprising a compound of formula VIII, or IX and/or an organic semiconductor material, layer or component.

The semiconductor is preferably an organic photovoltaic (PV) device (solar cell), a photodiode, or an organic field effect transistor. The structure and the components of the OFET device has been described in more detail above.

Accordingly, the invention provides organic photovoltaic (PV) devices (solar cells) comprising a compound of the formula VIII, or IX.

The structure of organic photovoltaic devices (solar cells) is, for example, described in C. Deibel et al. Rep. Prog. Phys. 73 (2010) 096401 and Christoph Brabec, Energy Environ. Sci 2. (2009) 347-303.

The PV device comprise in this order:
(a) a cathode (electrode),
(b) optionally a transition layer, such as an alkali halogenide, especially lithium fluoride,
(c) a photoactive layer,
(d) optionally a smoothing layer,
(e) an anode (electrode),
(f) a substrate.

The photoactive layer comprises the compounds of the formula VIII, or IX. Preferably, the photoactive layer is made of a compound of the formula VIII, or IX, as an electron donor and an acceptor material, like a fullerene, particularly a functionalized fullerene PCBM, as an electron acceptor. As stated above, the photoactive layer may also contain a polymeric binder. The ratio of the small molecules of formula VIII, or IX to the polymeric binder can vary from 5 to 95 percent. Preferably, the polymeric binder is a semicristalline polymer such as polystyrene (PS), high-density polyethylene (HDPE), polypropylene (PP) and polymethylmethacrylate (PMMA).

The fullerenes useful in this invention may have a broad range of sizes (number of carbon atoms per molecule). The term fullerene as used herein includes various cage-like molecules of pure carbon, including Buckminsterfullerene ($C_{60}$) and the related "spherical" fullerenes as well as carbon nanotubes. Fullerenes may be selected from those known in the art ranging from, for example, $C_{20}$-$C_{1000}$. Preferably, the fullerene is selected from the range of $C_{69}$ to $C_{96}$. Most preferably the fullerene is $C_{69}$ or $C_{70}$, such as [60]PCBM, or [70]PCBM. It is also permissible to utilize chemically modified fullerenes, provided that the modified fullerene retains acceptor-type and electron mobility characteristics. The acceptor material can also be a material selected from the group consisting of another compounds of formula VIII, or IX, or any semi-conducting polymer, such as, for example, a polymer of formula I, provided that the polymers retain acceptor-type and electron mobility characteristics, organic small molecules, carbon nanotubes, inorganic particles (quantum dots, quantum rods, quantum tripods, $TiO_2$, ZnO etc.).

The photoactive layer is made of a compound of the formula VIII, or IX, as an electron donor and a fullerene, particularly functionalized fullerene PCBM, as an electron acceptor. These two components are mixed with a solvent and applied as a solution onto the smoothing layer by, for example, the spin-coating method, the drop casting method, the Langmuir-Blodgett ("LB") method, the ink jet printing method and the dripping method. A squeegee or printing method could also be used to coat larger surfaces with such a photoactive layer. Instead of toluene, which is typical, a dispersion agent such as chlorobenzene is preferably used as a solvent. Among these methods, the vacuum deposition method, the spin-coating method, the ink jet printing method and the casting method are particularly preferred in view of ease of operation and cost.

In the case of forming the layer by using the spin-coating method, the casting method and ink jet printing method, the coating can be carried out using a solution and/or dispersion prepared by dissolving, or dispersing the composition in a concentration of from 0.01 to 90% by weight in an appropriate organic solvent such as benzene, toluene, xylene, tetrahydrofurane, methyltetrahydrofurane, N,N-dimethylformamide, acetone, acetonitrile, anisole, dichloromethane, dimethylsulfoxide, chlorobenzene, 1,2-dichlorobenzene and mixtures thereof.

The photovoltaic (PV) device can also consist of multiple junction solar cells that are processed on top of each other in order to absorb more of the solar spectrum. Such structures are, for example, described in App. Phys. Let. 90, 143512 (2007), Adv. Funct. Mater. 16, 1897-1903 (2006) and WO2004/112161.

A so called 'tandem solar cell' comprise in this order:
(a) a cathode (electrode),
(b) optionally a transition layer, such as an alkali halogenide, especially lithium fluoride,
(c) a photoactive layer,
(d) optionally a smoothing layer,
(e) a middle electrode (such as Au, Al, ZnO, $TiO_2$ etc.)
(f) optionally an extra electrode to match the energy level,
(g) optionally a transition layer, such as an alkali halogenide, especially lithium fluoride,
(h) a photoactive layer,
(i) optionally a smoothing layer,
(j) an anode (electrode),
(k) a substrate.

The PV device can also be processed on a fiber as described, for example, in US20070079867 and US 20060013549.

Due to their excellent self-organising properties the materials or films comprising the compounds of the formula VIII, or IX can also be used alone or together with other materials in or as alignment layers in LCD or OLED devices, as described for example in US2003/0021913.

An OFET device according to the present invention preferably comprises:

a source electrode, a drain electrode, a gate electrode, a semiconducting layer, one or more gate insulator layers, and optionally a substrate, wherein the semiconductor layer comprises a compound of formula VIII, or IX.

The gate, source and drain electrodes and the insulating and semiconducting layer in the OFET device may be arranged in any sequence, provided that the source and drain electrode are separated from the gate electrode by the insulating layer, the gate electrode and the semiconductor layer both contact the insulating layer, and the source electrode and the drain electrode both contact the semiconducting layer.

Preferably the OFET comprises an insulator having a first side and a second side, a gate electrode located on the first side of the insulator, a layer comprising a compound of formula VIII, or IX located on the second side of the insulator, and a drain electrode and a source electrode located on the polymer layer.

The following examples are included for illustrative purposes only and do not limit the scope of the claims. Unless otherwise stated, all parts and percentages are by weight. Weight-average molecular weight (Mw) and polydispersity (Mw/Mn=PD) are determined by High Temperature Gel Permeation Chromatography (HT-GPC) [*Apparatus*: GPC PL 220 from Agilent Technologies (Santa Clara, Calif., USA) yielding the responses from refractive index (RI), *Chromatographic conditions*: Column: 3 "PLgel Mixed B" columns from Agilent Technologies (Santa Clara, Calif., USA); with an average particle size of 10 □μm (dimensions 300×7.5 mm I.D.) Mobile phase: 1,2,4-trichlorobenzene (for GPC, Appli-Chem, Darmstadt, Germany) stabilised by butylhydroxytoluene (BHT, 1 g/l), Chromatographic temperature: 150° C.; Mobile phase flow: 1 ml/min; Solute concentration: about 1 mg/ml; Injection volume: 200 μl; Detection: RI, *Procedure of molecular weight calibration*: Relative calibration is done by use of a EasiVial calibration kit from Agilent Technologies (Santa Clara, Calif., USA) containing 12 narrow polystyrene calibration standards spanning the molecular weight range from 6,035,000 Da-162 Da, i. e., PS 6,035,000, PS 3,053,000, PS 915,000, PS 483,000, PS 184,900, PS 60,450, PS 19,720, PS 8,450, PS 3,370, PS 1,260, PS 580, PS 162 Da. A polynomic calibration is used to calculate the molecular weight.

All polymer structures given in the examples below are idealized representations of the polymer products obtained via the polymerization procedures described. If more than two components are copolymerized with each other sequences in the polymers can be either alternating or random depending on the polymerisation conditions.

EXAMPLES

Example 1

Synthesis of Polymer P-1

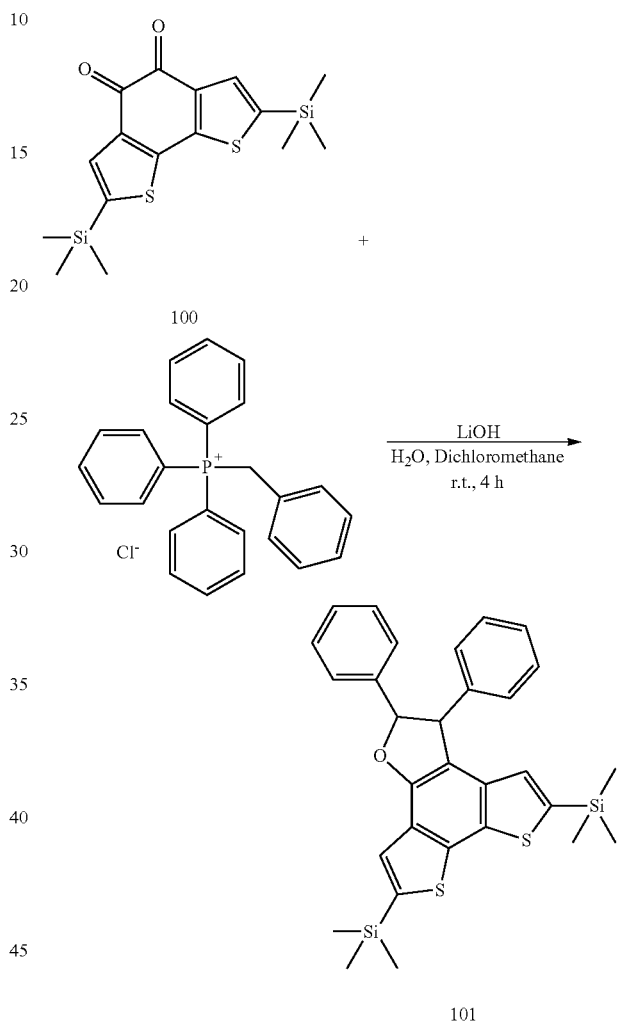

a) The synthesis of compound 100 is described, for example, in WO2009115413.

862 mg (20.55 mmol) lithium hydroxide monohydrate in 10 ml water are added to 2.5 g 6.85 mmol) of compound 100 and 5.46 g (14.04 mmol) benzyl(triphenyl)phosphonium chloride in 40 ml dichloromethane. The reaction mixture is stirred at 25° C. for 4 h. The organic phase is separated, the aqueous phase is extracted with dichloromethane. The combined organic phases are dried over magnesium sulphate and filtered. The solvent is distilled off and the product 101 is then purified by two successive column chromatographies (eluent: toluene/cyclohexane 1:10 and then toluene/cyclohexane 1:1).

Yield: 52% (1.89 g, white powder).

$^1$H NMR (400 MHz, CDCl$_3$): δ=7.75 (s, 1H), 7.47-7.22 (m, 10H), 6.86 (s, 1H), 5.81 (d, J=7.0 Hz, 1H), 4.96 (d, J=7.2 Hz, 1H), 0.46 (s, 9H), 0.30 (s, 9H).

$^{13}$C NMR (100 MHz, CDCl$_3$): δ=152.3, 142.4, 141.9, 141.3, 140.5, 138.7, 135.6, 131.1, 128.9 (2C), 128.7 (2C), 128.2 (2C), 128.1 (2C), 127.5, 127.2, 125.8 (2C), 125.2, 116.2, 94.1, 58.4, −0.2 (3C), −0.4 (3C). GC/MS: (CI pos.): 529.28 (MH$^+$).

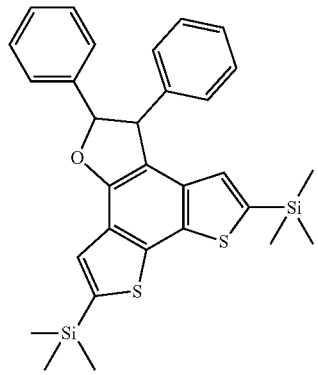

101 b) In a 100 mL flask previously flushed with nitrogen and equipped with a condenser and a nitrogen bubbler is introduced compound 101 (1.3 g, 2.46 mmol) and tetrahydrofurane (THF, 30 mL). A solution of tetrabutylammonium fluoride trihydrate (1.71 g, 5.41 mmol) in tetrahydrofurane (10 mL) is then added and the mixture is stirred for 2 h at room temperature. After that time water (100 mL) is added, and the product is extracted with dichloromethane. The combined organic phases are then dried over magnesium sulphate and filtered. The solvent is distilled off and the product 102 is then purified by column chromatography (eluent: cyclohexane/toluene 4:1). Yield: 96% (910 mg, white powder).

$^1$H NMR (400 MHz, CDCl$_3$): δ=7.60 (1H, d, J=5.5 Hz), 7.44-7.24 (12H, m), 6.74 (1H, d, J=5.5 Hz), 5.79 (1H, d, J=7.5 Hz), 4.93 (1H, d, J=7.5 Hz); GC/MS: (CI pos.): 385.16 (MH$^+$).

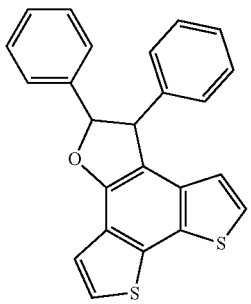

102

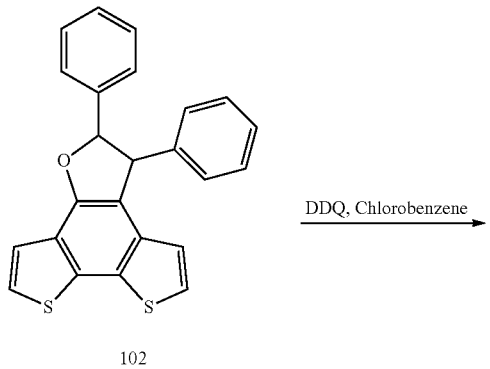

102

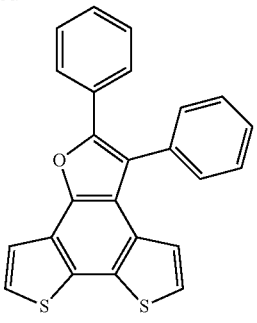

103 c) 0.52 g (2.29 mmol) 2,3-dichloro-5,6-dicyanobenzoquinone (DDQ) are added to 0.8 g (2.08 mmol) of compound 102 in 20 ml chlorobenzene. The reaction mixture is refluxed for 2 h under nitrogen, and then cooled to room temperature. Dichloromethane is added and the reaction mixture is washed with a sodium hydrogen carbonate solution. The organic phase is dried with magnesium sulphate and filtered. The solvent is evaporated on a rotary evaporator. The crude product is then purified by column chromatography (cyclohexane/toluene 4:1) to get product 103 as a white powder. Yield: 88% (702 mg, white powder).

$^1$H NMR (400 MHz, CDCl$_3$): δ=7.88 (1H, d, J=5.3 Hz), 7.70 (2H, m), 7.61-7.56 (5H, m), 7.53 (1H, d, J=5.5 Hz, 1H), 7.37-7.28 (4H, m), 6.97 (1H, d, J=5.3 Hz). GC/MS: (CI pos.): 383.21 (MH$^+$).

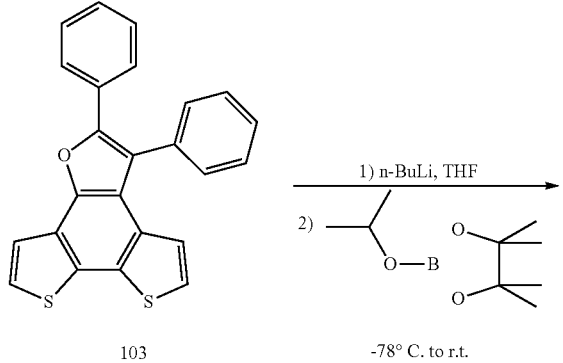

103

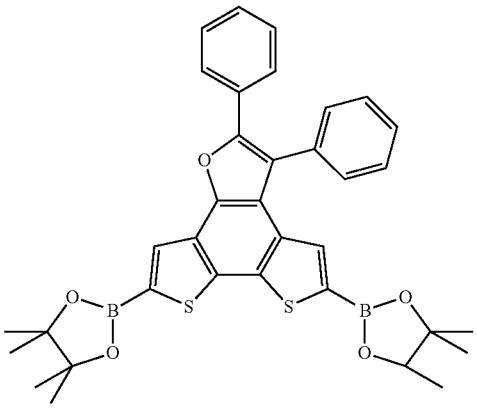

104 d) In a 3-neck flask equipped with a condenser and a nitrogen bubbler is introduced compound 103 (1.02 g, 2.67 mmol). The flask is flushed with nitrogen and tetrahydrofuran (THF) is added (80 mL). The solution is then cooled to −78° C. and a n-butyllithium solution (2.67 mL, 6.67 mmol, 2.5 M solution) is added dropwise. The resulting mixture is stirred for 1 h 20 at −78° C. After that time 2-isopropoxy-4,4,5,5-tetramethyl-1,3,2-dioxaborolane (1.49 g, 8.00 mmol) is added at −78° C. After 20 minutes at −78° C., the mixture is allowed to warm to room temperature and stirred 2 hours at room temperature. Then, water is added at 0° C. and the product is extracted with tert-butyl-methyl-ether (100 mL) and dichloromethane (two times 100 mL). The combined organic fractions are dried over anhydrous sodium sulphate, filtered and concentrated on rotary evaporator. The crude solid is triturated in hot acetonitrile and left to cool to 0° C. The white solid (product 104) is filtered and dried under vacuum. Yield: 72% (1.21 g, white powder).

$^1$H-NMR (400.1 MHz, CDCl$_3$): δ=8.40 (1H, s), 7.62-7.54 (7H, m), 7.52 (1H, s), 7.32-7.26 (3H, m), 1.43 (12H, s), 1.33 (12H, s). $^{13}$C NMR (100 MHz, CDCl$_3$): δ=149.1, 147.2, 135.9, 134.4, 133.6, 132.4, 131.8, 130.8, 130.4 (2C), 130.3, 129.2 (2C), 128.4 (2C), 128.2, 127.7, 126.2 (2C), 125.7, 121.4, 119.1, 84.6 (2C), 84.3 (2C), 24.9 (4C), 24.7 (4C).

e) The synthesis of 3,6-bis(5-bromothiophen-2-yl)-2,5-bis (2-hexyldecyl)pyrrolo[3,4-c]pyrrole-1,4(2H,5H)-dione 107 is, for example, described in WO2008/000664 and Y. Geerts; Tetrahedron 66 (2010) 1837-1845. In a flask equipped with a condenser, a mechanical stirrer, a nitrogen bubbler and a thermometer is introduced the bis-boronic ester 104 from step d) (400 mg, 0.63 mmol) and 3,6-bis(5-bromothiophen-2-yl)-2,5-bis(2-hexyldecyl)pyrrolo[3,4-c]pyrrole-1,4(2H,5H)-dione 107 (545 mg, 0.60 mmol). The flask is flushed with nitrogen and dry THF (30 mL) is added by syringe. The resulting red solution is heated to 60° C. and a solution of palladium(II) acetate (4.0 mg, 0.018 mmol) and 2-(di-tert-butylphosphino)-1-phenylpyrrole (20.7 mg, 0.072 mmol) in 10 mL THF is added. The resulting mixture is stirred for 5 minutes at reflux temperature. After that time finely crushed lithium hydroxide monohydrate (159 mg, 3.78 mmol) is added in a single portion at 60° C. and is stirred at reflux temperature for 4 hours. The reaction mixture is poured into ethanol (300 mL) and the precipitate is filtered on a Büchner funnel. The solid is then washed with 200 mL ethanol and 200 mL deionised water. The filtered solid is then put in a flask containing 150 mL chloroform and 150 mL of a 3% sodium cyanide aqueous solution and is heated under vigorous stirring at 60° C. overnight. The organic phase is washed with 100 mL water, and two thirds of the chloroform is then evaporated. Ethanol is added to precipitate the product, which is filtered on a Büchner funnel, washed with 300 mL ethanol and dried in the oven. The treatment with sodium cyanide is then repeated a second time. The dried solid is then purified by soxhlet extraction, first with tetrahydrofuran (200 mL, 6 h). The fraction soluble in tetrahydrofuran is discarded and the remaining solid is then subjected to soxhlet extraction with chloroform (200 mL, 7 h). The green solution is concentrated, the product is precipitated in ethanol, filtered and dried under reduced pressure to afford the polymer P-1 (598 mg, yield 88%). High temperature GPC: $M_w$=97700, $M_n$=46200, PD=2.11.

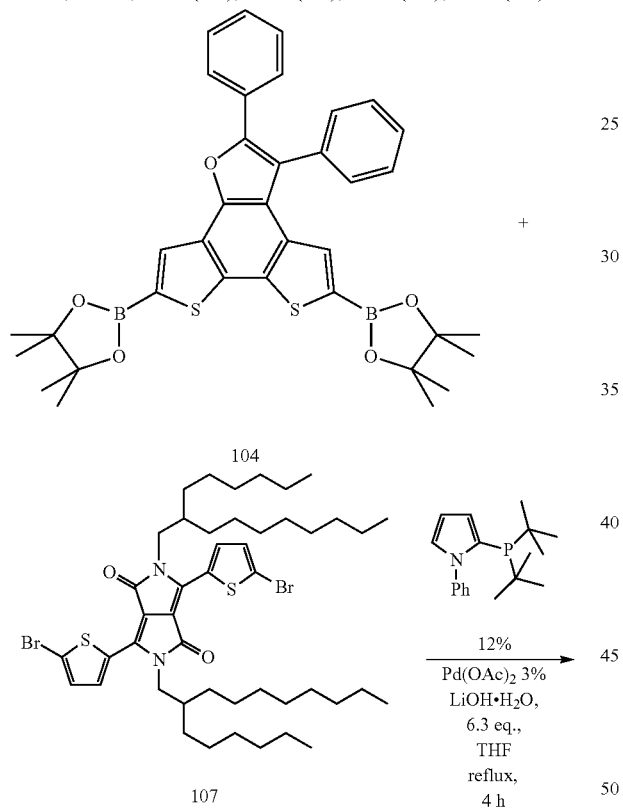

Example 2

Synthesis of Polymer P-2

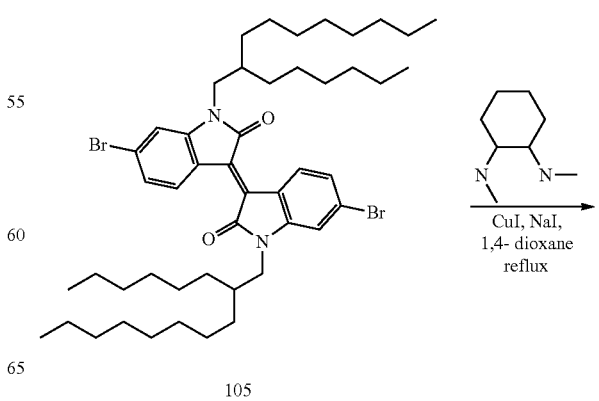

-continued

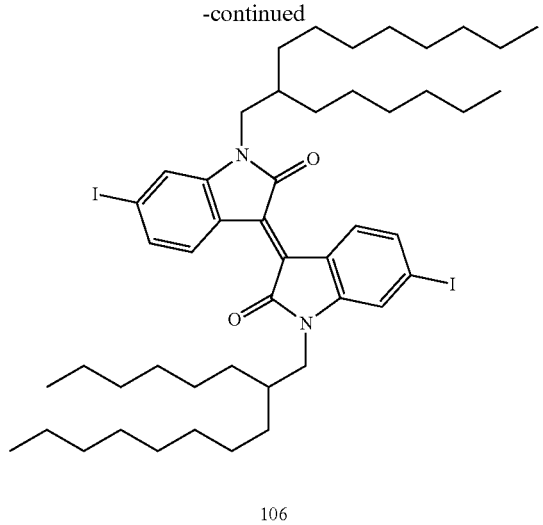

106

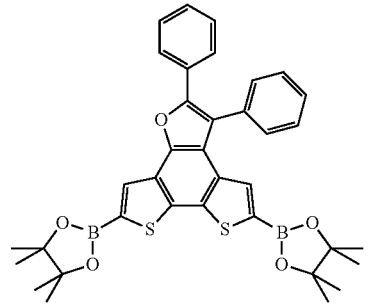

104

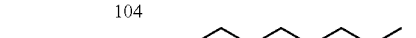

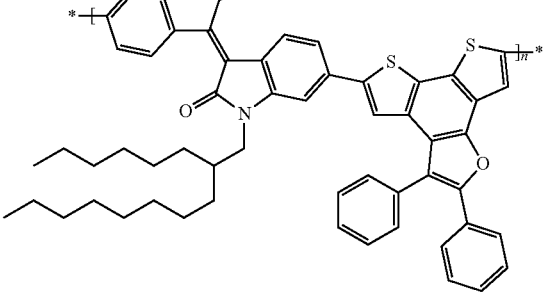

P-2 a) In a flask equipped with a condenser, is introduced compound 105 (7.00 g, 8.05 mmol), sodium iodide (4.83 g, 32.2 mmol) and copper iodide (153 mg, 0.81 mmol). The flask is flushed with nitrogen (3× vacuum/nitrogen) and 1,4-dioxane (175 mL) is added, followed by the trans-N,N-dimethylcyclohexane-1,2-diamine (229 mg, 1.61 mmol). The mixture is then stirred at reflux overnight. After that time the mixture is poured into 350 mL water. 350 mL of a 1 M NaOH aqueous solution is added, and the product is extracted with dichloromethane. The combined organic phases are dried over sodium sulphate and filtered. Solvents are removed on rotary evaporator. Analysis shows an unseparable mixture of product and starting material. The crude product is then subjected several times to similar reaction conditions until conversion is >97%. The crude product is then purified by column chromatography and recrystallization in isopropanol to afford the compound 106 as a red solid.

$^1$H-NMR (400.1 MHz, CDCl$_3$): δ=8.89 (2H, d, J=8.5 Hz), 7.38 (2H, dd, J=8.5, 1.8 Hz), 7.09 (2H, d, J=1.8 Hz), 3.60 (4H, d, J=7.2 Hz), 1.87 (2H, m), 1.38-1.20 (48H, m), 0.90-0.83 (12H, m); $^{13}$C NMR (100 MHz, CDCl$_3$): δ=167.9 (2C), 145.8 (2C), 132.9 (2C), 131.3 (2C), 130.9 (2C), 121.0 (2C), 117.2 (2C), 99.0 (2C), 44.6 (2C), 36.1 (2C), 31.9 (2C), 31.8 (2C), 31.5 (4C), 30.0 (2C), 29.7 (2C), 29.6 (2C), 29.3 (2C), 26.4 (2C), 26.3 (2C), 22.7 (2C), 22.6 (2C), 14.1 (4C)

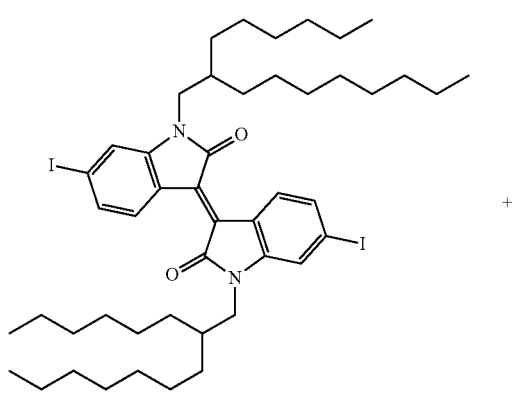

106 b) In a flask equipped with a condenser, a mechanical stirrer, a nitrogen bubbler and a thermometer is introduced the bis-boronic ester 104 (466 mg, 0.73 mmol) and (3E)-1-(2-hexyldecyl)-3-[1-(2-hexyldecyl)-6-iodo-2-oxo-indolin-3-ylidene]-6-iodo-indolin-2-one 106 (674 mg, 0.70 mmol). The flask is flushed with nitrogen and dry THF (40 mL) is added by syringe. The resulting red solution is heated to 60° C. and a solution of palladium(II) acetate (4.7 mg, 0.021 mmol) and 2-(di-tert-butylphosphino)-1-phenylpyrrole (24.1 mg, 0.084 mmol) in 10 mL THF is added. The resulting mixture is stirred for 5 minutes at reflux temperature. After that time finely crushed lithium hydroxide monohydrate (185 mg, 4.41 mmol) is added in a single portion at 60° C. and is stirred at reflux temperature for 5 hours. The reaction mixture is poured into ethanol (400 mL) and the precipitate is filtered on a Büchner funnel. The solid is then washed with 200 mL ethanol and 200 mL deionised water. The filtered solid is then put in a flask containing 150 mL chloroform and 150 mL of a 3% sodium cyanide aqueous solution and is heated under vigorous stirring at 55° C. overnight. The organic phase is washed three times with 100 mL water, and the chloroform is then evaporated. Ethanol is added to precipitate the product, which is filtered on a Büchner funnel, washed with 200 mL water and 50 mL ethanol and dried in the oven. The treatment with sodium cyanide is then repeated a second time. The dried solid is then purified by soxhlet extraction, first with acetone (200 mL, 2 h) and then with tert-butyl-methyl-ether (200 mL, 5 h). The fractions soluble in acetone and tert-butyl-methyl-ether are discarded and the remaining solid is then subjected to soxhlet extraction with THF (200 mL, 5 h). The solution is concentrated, the product is precipitated in ethanol, filtered and dried under reduced pressure to afford the polymer P-2 (659 mg, yield 86%). High temperature GPC: $M_w$=24600, Mn=15500, PD=1.58.

Example 3

Synthesis of Polymer P-3

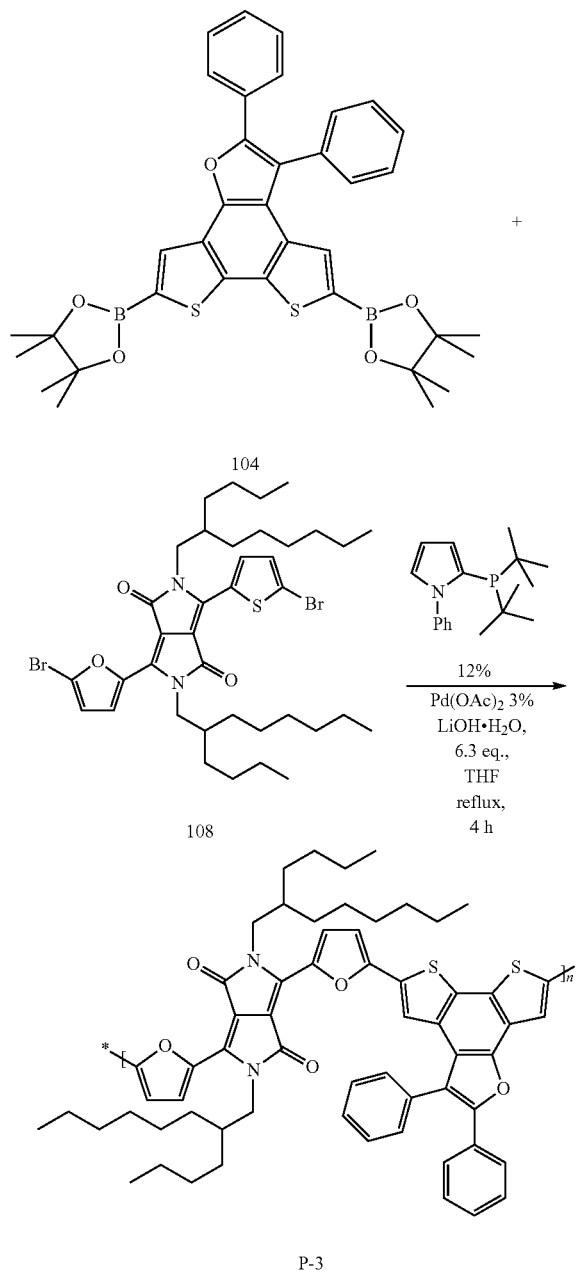

The synthesis of 3,6-bis(5-bromothiophen-2-yl)-2,5-bis(2-butyloctyl)pyrrolo[3,4-c]pyrrole-1,4(2H,5H)-dione 108 is, for example, described in WO2011/144566.

In a flask equipped with a condenser, a mechanical stirrer, a nitrogen bubbler and a thermometer is introduced compound 104 (400 mg, 0.63 mmol) and 3,6-bis(5-bromothiophen-2-yl)-2,5-bis(2-butyloctyppyrrolo[3,4-c]pyrrole-1,4(2H,5H)-dione 108 (458 mg, 0.60 mmol). The flask is flushed with nitrogen and dry THF (30 mL) is added by syringe. The resulting red solution is heated to 60° C. and a solution of palladium(II) acetate (4.0 mg, 0.018 mmol) and 2-(di-tert-butylphosphino)-1-phenylpyrrole (20.7 mg, 0.072 mmol) in 10 mL THF is added. The resulting mixture is stirred for 5 minutes at reflux temperature. After that time finely crushed lithium hydroxide monohydrate (159 mg, 3.78 mmol) is added in a single portion at 60° C. and the mixture is stirred at reflux temperature for 4 hours. The reaction mixture is poured into ethanol (300 mL) and the precipitate is filtered on a Büchner funnel. The solid is then washed with 200 mL ethanol and 200 mL deionised water. The filtered solid is then put in a flask containing 150 mL chloroform and 150 mL of a 3% sodium cyanide aqueous solution and is heated under vigorous stirring at 60° C. overnight. The organic phase is washed with water, and two thirds of the chloroform is then evaporated. Ethanol is added to precipitate the product, which is filtered on a Büchner funnel, washed with 300 mL ethanol and dried in the oven. The treatment with sodium cyanide is then repeated a second time. The dried solid is then purified by soxhlet extraction. Fractions soluble in acetone, tert-butyl-methyl-ether and cyclohexane are discarded. Soxhlet extraction is then performed with tetrahydrofuran, and the green solution is concentrated, the product is precipitated in ethanol, filtered and dried under reduced pressure to afford the polymer P-3 (510 mg, yield 86%). High temperature GPC: $M_w$=91400, $M_n$=33100, PD=2.76.

Application Examples 1, 2 and 3

Photovoltaic Application of the Semiconducting Polymers:

The solar cell has the following structure: Al electrode/LiF layer/organic layer, including compound of the invention/[poly(3,4-ethylenedioxy-thiophene) (PEDOT)/poly(styrenesulfonic acid) (PSS)]/ITO electrode/glass substrate. The solar cells are made by spin coating a layer of the PEDOT-PSS on a pre-patterned ITO on glass substrate. Then a 1:2 mixture of the semiconducting polymer (1% by weight): [70]PCBM (a substituted $C_{70}$ fullerene) is spin coated (organic layer). LiF and Al are sublimed under high vacuum through a shadow-mask.

Solar Cell Performance

The solar cell is measured in homemade solar light simulator with Osram Xenon Short Arc XBO 450 W lamp. Then with the External Quantum Efficiency (EQE) graph the current is estimated under AM1.5 conditions.

The OPV performances of Semiconducting polymers are shown in the table below:

| Appl. Example | Semiconductor | Solvent | Jsc, mA/cm² | Voc, V | FF, % | η, % |
|---|---|---|---|---|---|---|
| 1 | Polymer P-1 | CHCl₃/oDCB (9:1) | −9.61 | 0.76 | 50.1 | 3.62 |
| 2 | Polymer P-2 | Xylene/Tetraline (8:2) | −3.01 | 0.94 | 56.0 | 1.55 |
| 3 | Polymer P-3 | CHCl₃/oDCB (8:2) | −12.00 | 0.81 | 49.0 | 4.73 |

Application Examples 4, 5 and 6

OFET Application of the Semiconducting Polymers:
Semiconductor Film Deposition:

Siliconwafers (Si n- -(425±40 μm)) with a 230 nm thick $SiO_2$ dielectric and patterned indium tin oxide (15 nm)/gold (30 nm) contacts (L=20, 10, 5, 2.5 μm, W=0.01 m; Fraunhofer IPMS (Dresden)) are prepared by standard cleaning by washing with acetone and i-propanol followed by oxygen plasma treatment for 30 minutes. The substrates are transferred in a glove box. An octyltrichlorsilane (OTS) monolayer is grown on the dielectric surface by putting the substrates in a 50 mM solution of octyltrichlorosilane (OTS) in trichloroethylene for 1 h. After monolayer growth, the substrates are washed with toluene to remove physisorbed silane. The semiconductor is dissolved in a proper solvent in a concentration 0.75% by weight at 80° C. and spin-coated at 1500 rpms for 60 s onto the substrates.

OFET Measurement:

OFET transfer and output characteristics are measured on an Agilent 4155C semiconductor parameter analyzer. The devices are annealed in a glovebox at 150° C. for 15 minutes before the measurements are done in a glove box under a nitrogen atmosphere at room temperature. For p-type transistors the gate voltage ($V_g$) varies from 10 to −30 V and at drain voltage ($V_d$) equal to −3 and −30V for the transfer characterisation. For the output characterization $V_d$ is varied from 0 to −30V at $V_g$=0, −10, −20, −30 V.

| Appl. Example | Semiconductor | Solvent | Mobility, $cm^2/Vs$ | On/off |
|---|---|---|---|---|
| 4 | Polymer P-1 | oDCB | $1.80 \cdot 10^{-2}$ | $1.10 \cdot 10^5$ |
| 5 | Polymer P-2 | oDCB | $2.00 \cdot 10^{-3}$ | $4.30 \cdot 10^5$ |
| 6 | Polymer P-3 | oDCB | $6.80 \cdot 10^{-3}$ | $1.80 \cdot 10^6$ |

The invention claimed is:

1. A polymer, comprising;
a repeating unit of formula (I):

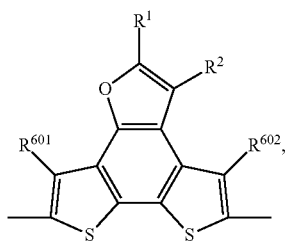

where $R^1$ and $R^2$ are each independently H, F, $C_1$-$C_{18}$ alkyl, $C_1$-$C_{18}$ alkyl which is substituted by E' and/or interrupted by D', $C_6$-$C_{24}$ aryl, $C_6$-$C_{24}$ aryl which is substituted by G', $C_2$-$C_{20}$ heteroaryl, $C_2$-$C_{20}$ heteroaryl which is substituted by G', or $R^1$ and $R^2$ together form a group

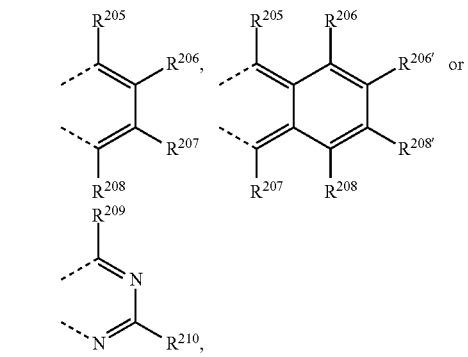

wherein $R^{205}$, $R^{206}$, $R^{206'}$, $R^{207}$, $R^{208}$, $R^{208'}$, $R^{209}$ and $R^{210}$ are each independently H, $C_1$-$C_{18}$ alkyl, $C_1$-$C_{18}$ alkyl which is substituted by E' and/or interrupted by D', $C_1$-$C_{18}$ alkoxy, or $C_1$-$C_{18}$ alkoxy which is substituted by E' and/or interrupted by D', $C_1$-$C_{18}$ fluoroalkyl, $C_6$-$C_{24}$ aryl, $C_6$-$C_{24}$ aryl which is substituted by G', $C_2$-$C_{20}$ heteroaryl, $C_2$-$C_{20}$ heteroaryl which is substituted by G', $C_2$-$C_{18}$ alkenyl, $C_2$-$C_{18}$ alkynyl, $C_7$-$C_{25}$ aralkyl, $C_7$-$C_{25}$ aralkyl which is substituted by G'; CN, or —CO—$R^{28}$, $R^{601}$ and $R^{602}$ are each independently H, halogen, $C_1$-$C_{25}$ alkyl, $C_3$-$C_{12}$ cycloalkyl, $C_2$-$C_{25}$ alkenyl, $C_2$-$C_{25}$ alkynyl, $C_6$-$C_{24}$ aryl, $C_6$-$C_{24}$ aryl which is substituted by G', $C_7$-$C_{25}$ aralkyl, or $C_7$-$C_{25}$ aralkyl which is substituted by G';

D' is —CO—, —COO—, —S—, —SO—, —$SO_2$—, —O—, —$NR^{65}$—, —$SiR^{70}R^{71}$—, —$POR^{72}$—, —$CR^{63}$=$CR^{64}$—, or —C≡C—, and E' is —$OR^{69}$, —$SR^{69}$, —$NR^{65}R^{66}$, —$COR^{68}$, —$COOR^{67}$, —$CONR^{65}R^{66}$, —CN, $CF_3$, or halogen, G' is E', $C_1$-$C_{18}$ alkyl, or $C_1$-$C_{18}$ alkyl which is interrupted by —O—, $R^{28}$ is H; $C_6$-$C_{18}$ aryl; $C_6$-$C_{18}$ aryl which is substituted by $C_1$-$C_{18}$ alkyl, or $C_1$-$C_{18}$ alkoxy; $C_1$-$C_{18}$ alkyl; or $C_1$-$C_{18}$ alkyl which is interrupted by —O—, $R^{63}$ and $R^{64}$ are each independently $C_6$-$C_{18}$ aryl; $C_6$-$C_{18}$ aryl which is substituted by $C_1$-$C_{18}$ alkyl, or $C_1$-$C_{18}$ alkoxy; $C_1$-$C_{18}$ alkyl; or $C_1$-$C_{18}$ alkyl which is interrupted by —O—;

$R^{65}$ and $R^{66}$ are each independently $C_6$-$C_{18}$ aryl; $C_6$-$C_{18}$ aryl which is substituted by $C_1$-$C_{18}$ alkyl, or $C_1$-$C_{18}$ alkoxy; $C_1$-$C_{18}$ alkyl; or $C_1$-$C_{18}$ alkyl which is interrupted by —O—; or $R^{65}$ and $R^{66}$ together form a five or six membered ring, $R^{67}$ is $C_6$-$C_{18}$ aryl; $C_6$-$C_{18}$ aryl which is substituted by $C_1$-$C_{18}$ alkyl, or $C_1$-$C_{18}$ alkoxy; $C_1$-$C_{18}$ alkyl; or $C_1$-$C_{18}$ alkyl which is interrupted by —O—, $R^{68}$ is H; $C_6$-$C_{18}$ aryl; $C_6$-$C_{18}$ aryl which is substituted by $C_1$-$C_{18}$ alkyl, or $C_1$-$C_{18}$ alkoxy; $C_1$-$C_{18}$ alkyl; or $C_1$-$C_{18}$ alkyl which is interrupted by —O—, $R^{69}$ is $C_6$-$C_{18}$ aryl; $C_6$-$C_{18}$ aryl, which is substituted by $C_1$-$C_{18}$ alkyl, or $C_1$-$C_{18}$ alkoxy; $C_1$-$C_{18}$ alkyl; or $C_1$-$C_{18}$ alkyl which is interrupted by —O—, $R^{70}$ and $R^{71}$ are each independently $C_1$-$C_{18}$ alkyl, $C_6$-$C_{18}$ aryl, or $C_6$-$C_{18}$ aryl, which is substituted by $C_1$-$C_{18}$ alkyl, and $R^{72}$ is $C_1$-$C_{18}$ alkyl, $C_6$-$C_{18}$ aryl, or $C_6$-$C_{18}$ aryl, which is substituted by $C_1$-$C_{18}$ alkyl.

2. The polymer according to claim 1,

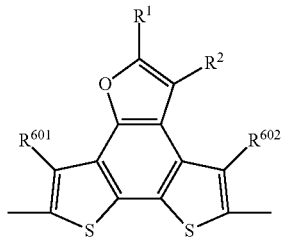

wherein
R¹ and R² are each independently a group of formula

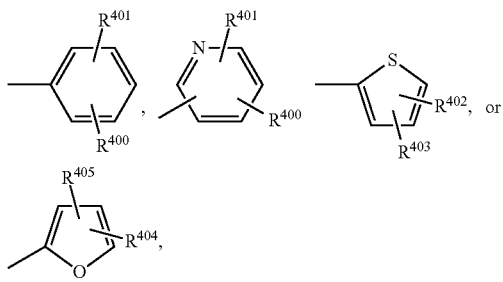

where $R^{400}$, $R^{401}$, $R^{402}$, $R^{403}$, $R^{404}$ and $R^{405}$ are each independently H, CN, F, CF$_3$, C$_1$-C$_{18}$ alkoxy; C$_1$-C$_{18}$ alkyl; or C$_1$-C$_{18}$ alkyl which is interrupted by —O—, or
R¹ and R² together form a group

and
$R^{601}$ and $R^{602}$ are each independently hydrogen, or C$_1$-C$_{25}$ alkyl.

3. The polymer according to claim 1, which is a polymer of formula

or a polymer, comprising repeating units of formulae

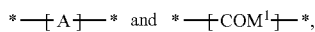

wherein
n ranges from 4 to 1000,
A is a repeating unit of the formula (I), and
—COM¹- is a repeating unit of

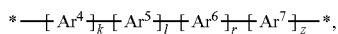

where k is 0, 1, 2, or 3; l is 1, 2, or 3; r is 0, 1, 2, or 3; z is 0, 1, 2, or 3; Ar⁴, Ar⁵, Ar⁶ and Ar⁷ are each independently of a formula:

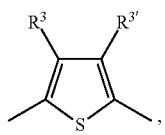 (XIa)

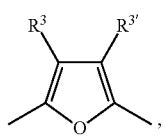 (XIb)

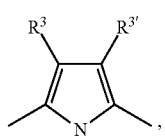 (XIc)

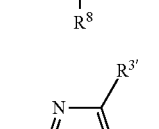 (XId)

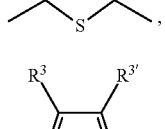 (XIe)

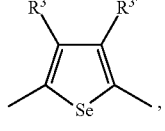 (XIf)

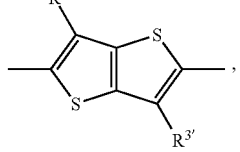 (XIg)

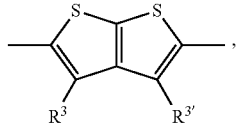 (XIh)

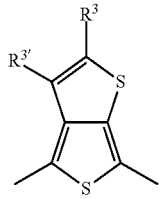 (XIi)

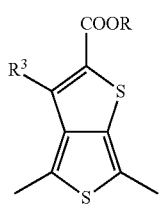 (XIj)

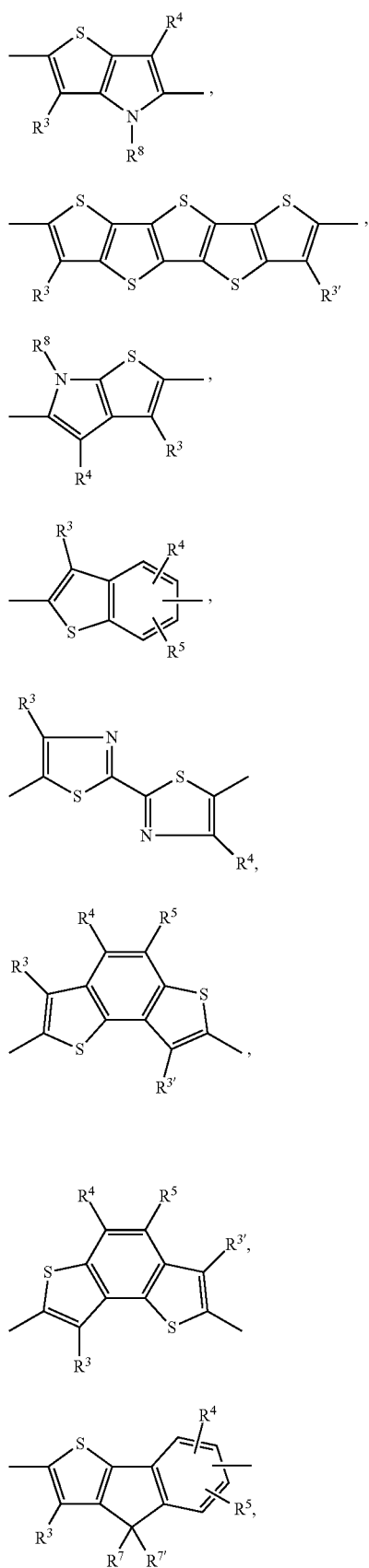
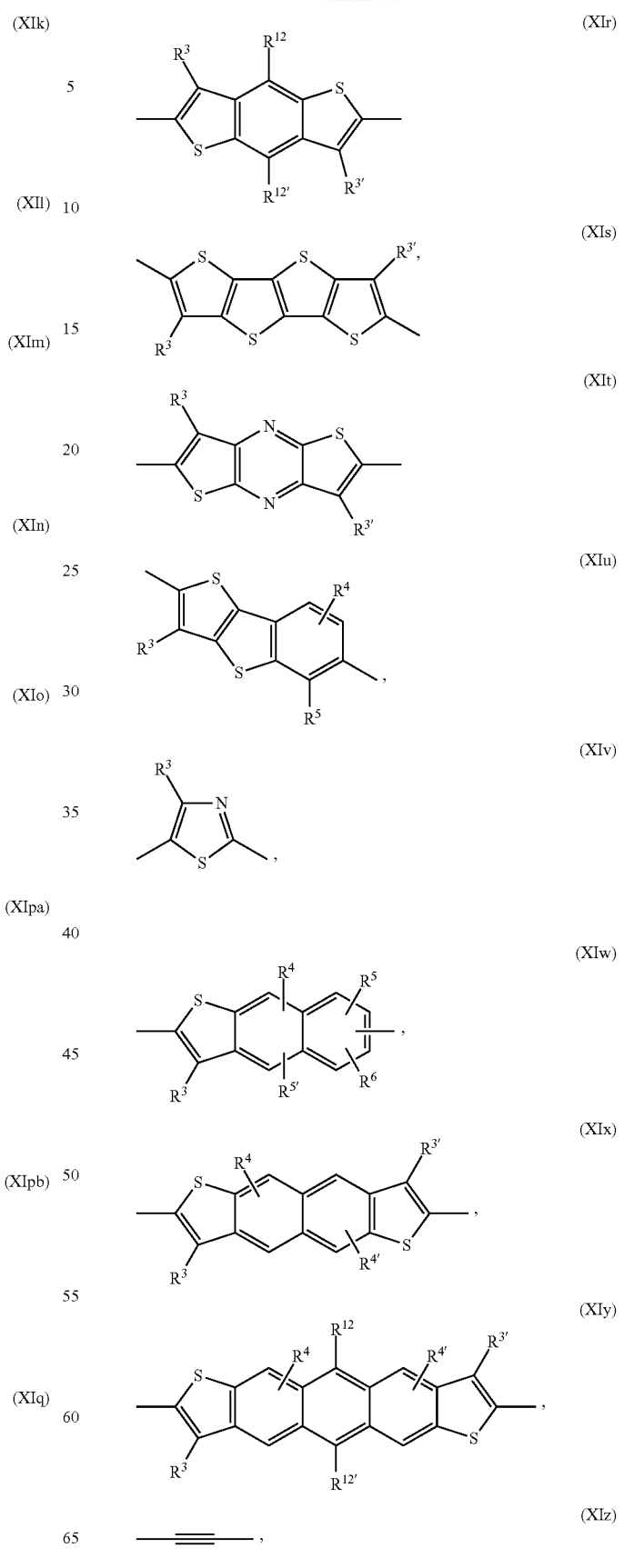

-continued
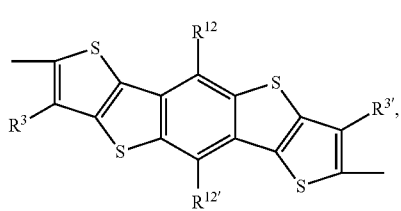
(XIIa)
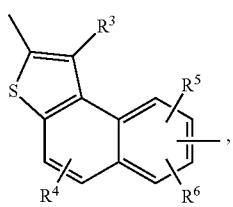
(XIIb)
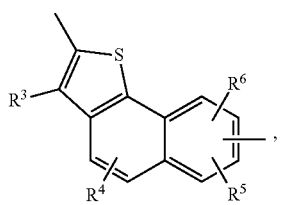
(XIIc)
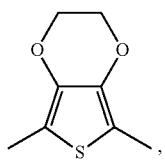
(XIId)
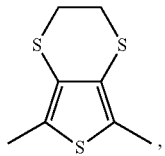
(XIIe)
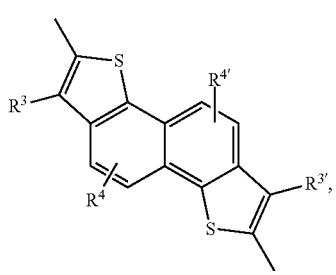
(XIIf)
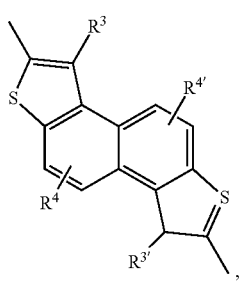
(XIIg)
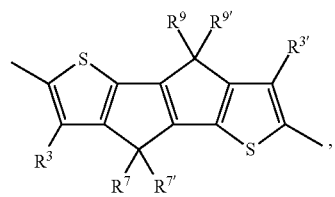
(XIIh)
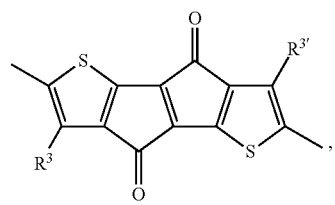
(XIIi)
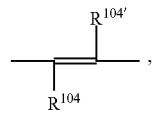
(XIIj)
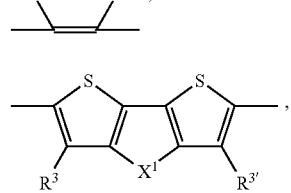
(XIIk)
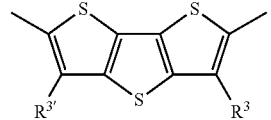
(XIII)
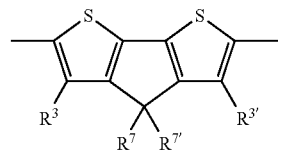
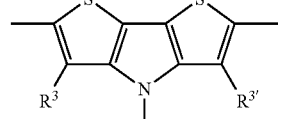
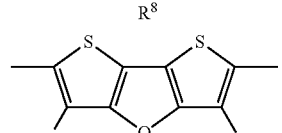
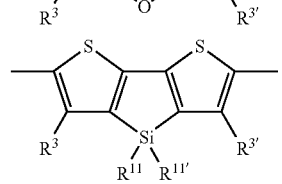

-continued
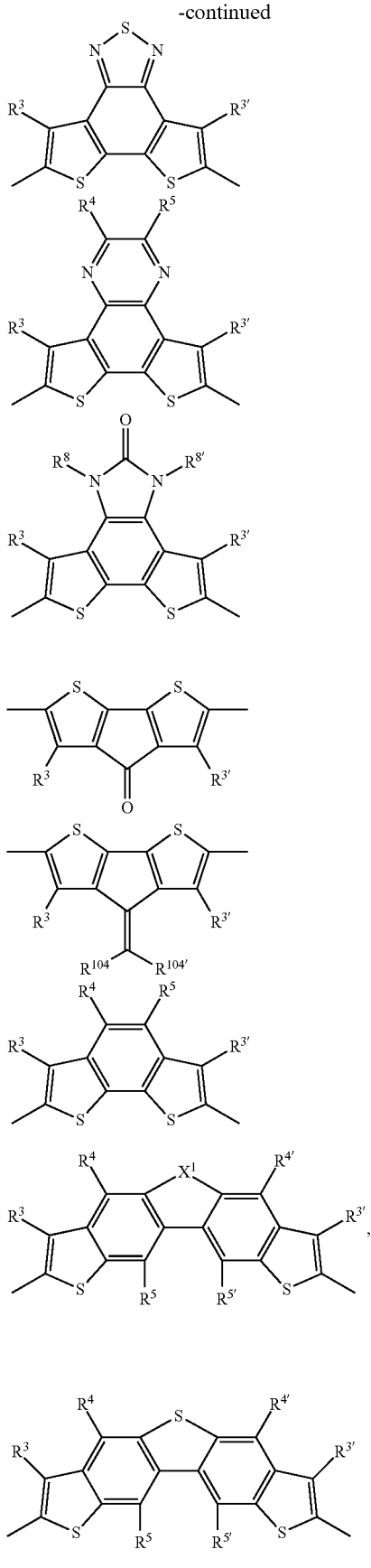
where
X¹ is —O—, —S—, —NR⁸—, —Si(R¹¹)(R¹¹')—, —Ge(R¹¹)(R¹¹')—, —C(R⁷)(R⁷')—, —C(=O)—, —C(=CR¹⁰⁴R¹⁰⁴')—,
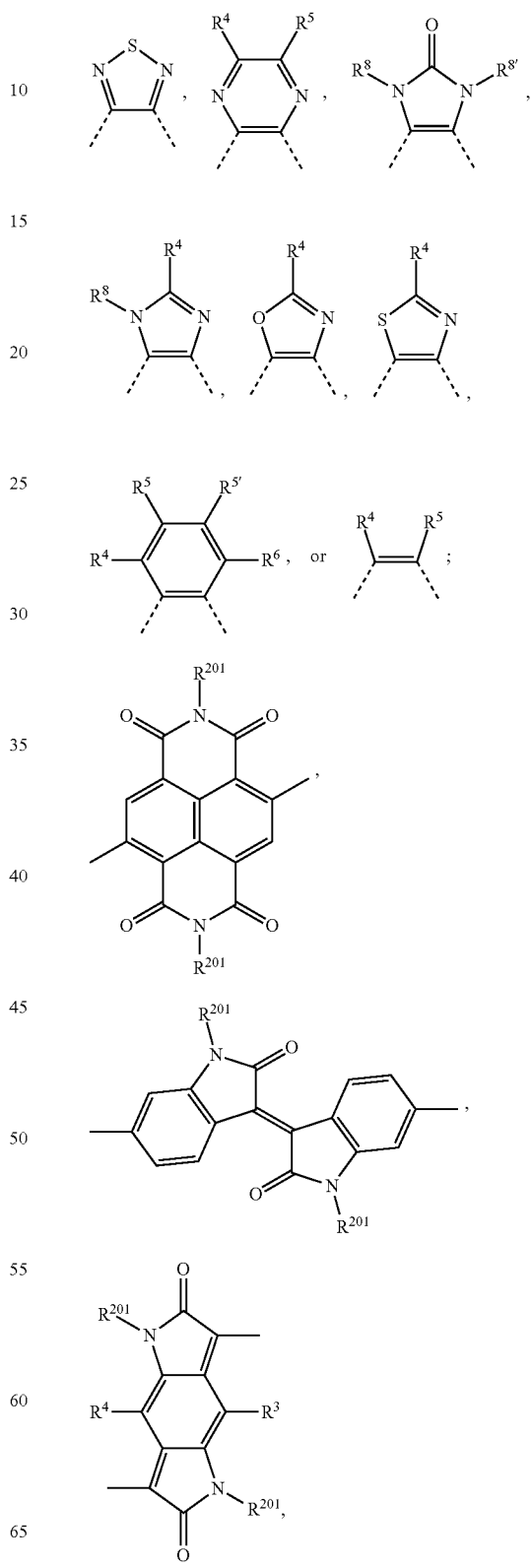

-continued
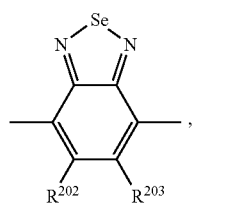
(XVd)
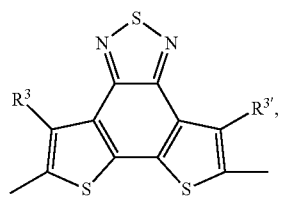
(XVe)
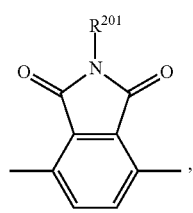
(XVf)
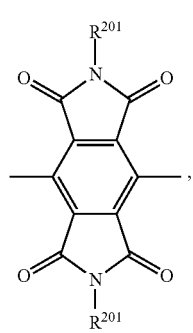
(XVg)
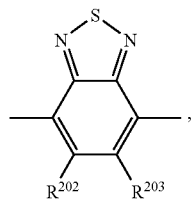
(XVh)
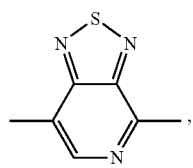
(XVi)
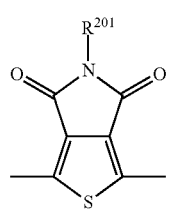
(XVj)
-continued
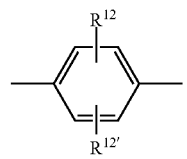
(XVk)
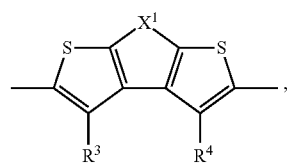
(XVl)
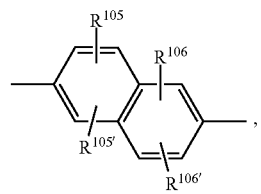
(XVm)
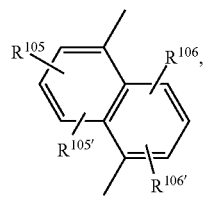
(XVn)
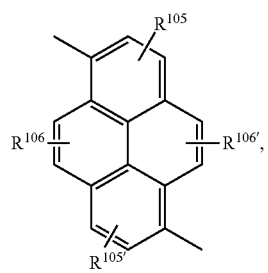
(XVo)
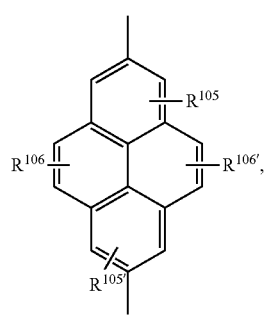
(XVp)
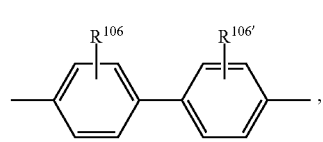
(XVq)

-continued

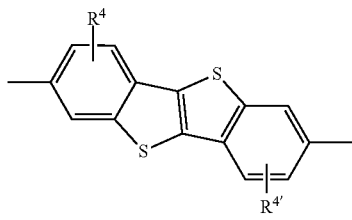
(XVr)

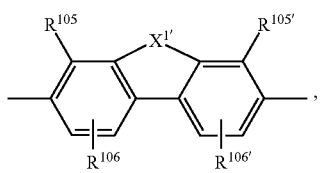
(XVs)

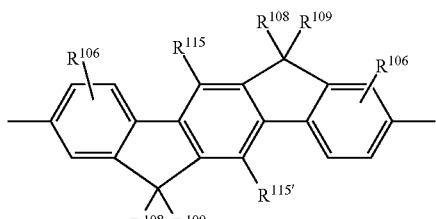

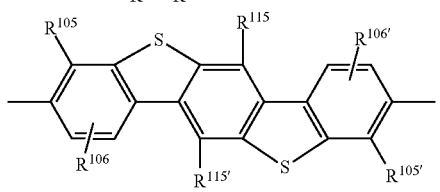 and

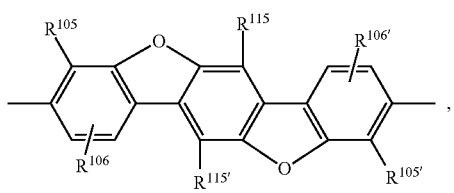
(XVuc)

where
X$^{1'}$ is S, O, NR$^{107}$—, —Si(R$^{117}$)(R$^{117'}$)—, —Ge(R$^{117}$)(R$^{117'}$)—, —C(R$^{106}$)(R$^{109}$)—, —C(=O)—, —C(=CR$^{104}$R$^{104'}$)—,

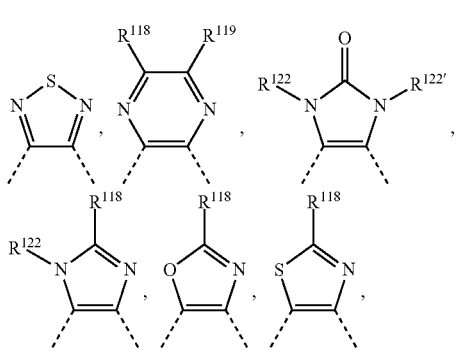
(XVu)

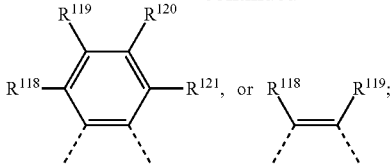

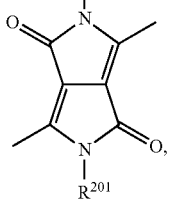

R$^3$ and R$^{3'}$ are each independently hydrogen, halogen, halogenated C$_1$-C$_{25}$ alkyl, cyano, C$_1$-C$_{25}$ alkyl, which is optionally interrupted by one or more oxygen or sulphur atoms; C$_7$-C$_{25}$ arylalkyl, or C$_1$-C$_{25}$ alkoxy;

R$^{104}$ and R$^{104'}$ are each independently hydrogen, cyano, COOR$^{103}$, C$_1$-C$_{25}$ alkyl, or C$_6$-C$_{24}$ aryl or C$_2$-C$_{20}$ heteroaryl, R$^4$, R$^{4'}$, R$^5$, R$^{5'}$, R$^6$, and R$^{6'}$ are each independently hydrogen, halogen, halogenated C$_1$-C$_{25}$ alkyl, cyano, C$_1$-C$_{25}$ alkyl, which is optionally interrupted by one or more oxygen or sulphur atoms; C$_7$-C$_{25}$ arylalkyl, or C$_1$-C$_{25}$ alkoxy;

R$^7$, R$^{7'}$, R$^9$ and R$^{9'}$ are each independently hydrogen, C$_1$-C$_{25}$ alkyl, which is optionally interrupted by one or more oxygen or sulphur atoms; or C$_7$-C$_{25}$ arylalkyl, R$^8$ and R$^{8'}$ are each independently hydrogen, C$_6$-C$_{18}$ aryl; C$_6$-C$_{18}$ aryl which is substituted by C$_1$-C$_{18}$ alkyl, or C$_1$-C$_{18}$ alkoxy; or C$_1$-C$_{25}$ alkyl, which is optionally interrupted by one or more oxygen or sulphur atoms; or C$_7$-C$_{25}$ arylalkyl, R$^{11}$ and R$^{11'}$ are each independently C$_1$-C$_{25}$ alkyl group, C$_7$-C$_{25}$ arylalkyl, or a phenyl group, which is optionally substituted one to three times with C$_1$-C$_8$ alkyl and/or C$_1$-C$_8$ alkoxy;

R$^{12}$ and R$^{12'}$ are each independently hydrogen, halogen, cyano, C$_1$-C$_{25}$ alkyl, which is optionally interrupted by one or more oxygen or sulphur atoms, C$_1$-C$_{25}$ alkoxy, C$_7$-C$_{25}$ arylalkyl, or $$\equiv\!\!-\!\!R^{13},$$

where R$^{13}$ is a C$_1$-C$_{10}$alkyl group, or a tri(C$_1$-C$_8$alkyl)silyl group; or R$^{104}$ and R$^{104'}$ are each independently hydrogen, C$_1$-C$_{18}$ alkyl, C$_6$-C$_{10}$ aryl, which is optionally substituted by G, or C$_2$-C$_8$ heteroaryl, which is optionally substituted by G, R$^{105}$, R$^{105'}$, R$^{106}$ and R$^{106'}$ are each independently hydrogen, halogen, cyano, C$_1$-C$_{25}$ alkyl, which is optionally interrupted by one or more oxygen or sulphur atoms; C$_7$-C$_{25}$ arylalkyl, or C$_1$-C$_{18}$ alkoxy, R$^{107}$ is hydrogen, C$_7$-C$_{25}$ arylalkyl, C$_6$-C$_{18}$ aryl; C$_6$-C$_{18}$ aryl which is substituted by C$_1$-C$_{18}$ alkyl, or C$_1$-C$_{18}$ alkoxy; C$_1$-C$_{18}$ perfluoroalkyl; C$_1$-C$_{25}$ alkyl; which is optionally interrupted by —O—, or —S—; or —COOR$^{103}$;

$R^{108}$ and $R^{109}$ are each independently H, $C_1$-$C_{25}$ alkyl, $C_1$-$C_{25}$ alkyl which is substituted by E and/or interrupted by D, $C_7$-$C_{25}$ arylalkyl, $C_6$-$C_{24}$ aryl, $C_6$-$C_{24}$ aryl which is substituted by G, $C_2$-$C_{20}$ heteroaryl, $C_2$-$C_{20}$ heteroaryl which is substituted by G, $C_2$-$C_{18}$ alkenyl, $C_2$-$C_{18}$ alkynyl, $C_1$-$C_{18}$ alkoxy, $C_1$-$C_{18}$ alkoxy which is substituted by E and/or interrupted by D, or $C_7$-$C_{25}$ aralkyl, or $R^{108}$ and $R^{109}$ together form a group of formula $=CR^{110}R^{111}$, where $R^{110}$ and $R^{111}$ are each independently H, $C_1$-$C_{18}$ alkyl, $C_1$-$C_{18}$ alkyl which is substituted by E and/or interrupted by D, $C_6$-$C_{24}$ aryl, $C_6$-$C_{24}$ aryl which is substituted by G, or $C_2$-$C_{20}$ heteroaryl, or $C_2$-$C_{20}$ heteroaryl which is substituted by G, or $R^{108}$ and $R^{109}$ together form a five or six membered ring, which is optionally substituted by $C_1$-$C_{18}$ alkyl, $C_1$-$C_{18}$ alkyl which is substituted by E and/or interrupted by D, $C_6$-$C_{24}$ aryl, $C_6$-$C_{24}$ aryl which is substituted by G, $C_2$-$C_{20}$ heteroaryl, $C_2$-$C_{20}$ heteroaryl which is substituted by G, $C_2$-$C_{18}$ alkenyl, $C_2$-$C_{18}$ alkynyl, $C_1$-$C_{18}$ alkoxy, $C_1$-$C_{18}$ alkoxy which is substituted by E and/or interrupted by D, or $C_7$-$C_{25}$ aralkyl, D is —CO—, —COO—, —S—, —O—, or —$NR^{112'}$—, E is $C_1$-$C_8$ thioalkoxy, $C_1$—C alkoxy, CN, —$NR^{112'}R^{113'}$, —$CONR^{112'}R^{113'}$, or halogen, G is E, or $C_1$-$C_{18}$ alkyl, and $R^{112'}$ and $R^{113'}$ are each independently H; $C_6$-$C_{18}$aryl; $C_6$-$C_{18}$ aryl which is substituted by $C_1$-$C_{18}$ alkyl, or $C_1$-$C_{18}$ alkoxy; $C_1$-$C_{18}$ alkyl; or $C_1$-$C_{18}$ alkyl which is interrupted by —O—, $R^{115}$ and $R^{115'}$ are each independently hydrogen, halogen, cyano, $C_1$-$C_{25}$ alkyl, which is optionally interrupted by one or more oxygen or sulphur atoms, $C_1$-$C_{25}$ alkoxy, $C_7$-$C_{25}$ arylalkyl, or

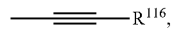

where $R^{116}$ is a $C_1$-$C_{10}$ alkyl group, or a tri($C_1$-$C_8$alkyl)silyl group;

$R^{117}$ and $R^{117'}$ are each independently $C_1$-$C_{25}$ alkyl group, $C_7$-$C_{25}$ arylalkyl, or a phenyl group, which is optionally substituted one to three times with $C_1$-$C_8$ alkyl and/or $C_1$-$C_8$ alkoxy;

$R^{118}$, $R^{119}$, $R^{120}$ and $R^{121}$ are each independently hydrogen, halogen, halogenated $C_1$-$C_{25}$ alkyl, cyano, $C_1$-$C_{25}$ alkyl, which is optionally interrupted by one or more oxygen or sulphur atoms; $C_7$-$C_{25}$ arylalkyl, or $C_1$-$C_{25}$ alkoxy;

$R^{122}$ and $R^{122'}$ are each independently hydrogen, $C_6$-$C_{18}$ aryl; $C_6$-$C_{18}$ aryl which is substituted by $C_1$-$C_{18}$ alkyl, or $C_1$-$C_{18}$ alkoxy; or $C_1$-$C_{25}$ alkyl, which is optionally interrupted by one or more oxygen or sulphur atoms; or $C_7$-$C_{25}$ arylalkyl, $R^{201}$ is selected from the group consisting of hydrogen, a $C_1$-$C_{100}$alkyl group, —$COOR^{103}$, a $C_1$-$C_{100}$ alkyl group substituted by one or more halogen atoms, a hydroxyl group, a nitro group, —CN, a $C_6$-$C_{18}$aryl group and/or interrupted by —O—, —COO—, —OCO— or —S—; a $C_7$-$C_{25}$ arylalkyl group, a carbamoyl group, a $C_5$-$C_{12}$ cycloalkyl group, which is optionally substituted one to three times with $C_1$-$C_{100}$alkyl and/or $C_1$-$C_{100}$alkoxy, a $C_6$-$C_{24}$aryl group, which is optionally substituted one to three times with $C_1$-$C_{100}$ alkyl, $C_1$-$C_{100}$ thioalkoxy, and/or $C_1$-$C_{100}$ alkoxy; and pentafluorophenyl;

$R^{103}$ and $R^{114}$ are each independently $C_1$-$C_{25}$ alkyl, which is optionally interrupted by one or more oxygen or sulphur atoms, and $R^{202}$ and $R^{203}$ are each independently selected from the group consisting of H, F, —CN, $C_1$-$C_{100}$alkyl, which is optionally interrupted by one or more oxygen or sulphur atoms; and $C_1$-$C_{100}$ alkoxy.

4. The polymer according to claim 1, comprising: units of

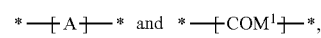

wherein

A is a repeating unit of the formula (I), and

—$COM^1$- is a repeating unit of

(XIa)

(XId)

(XIh)

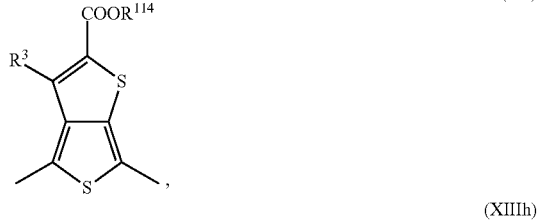

(XIi)

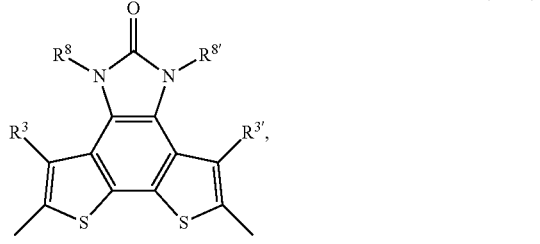

(XIIIh)

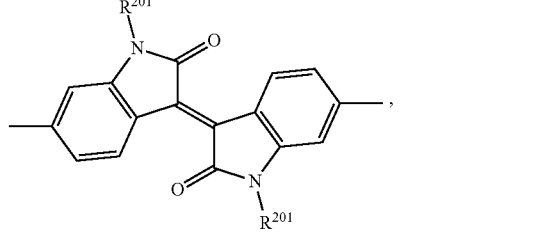

(XVb)

-continued

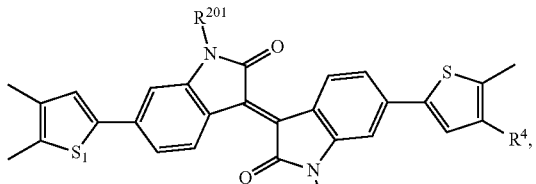
(XVb')

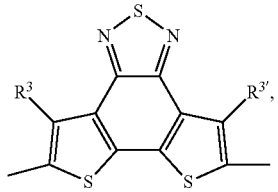
(XVe)

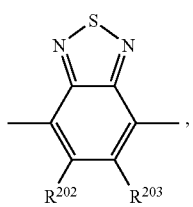
(XVh)

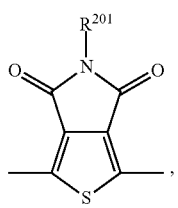
(XVj)

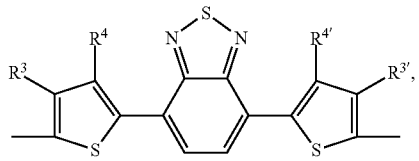
(XVh')

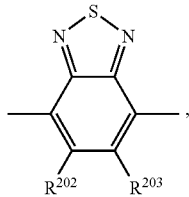
(XVh)

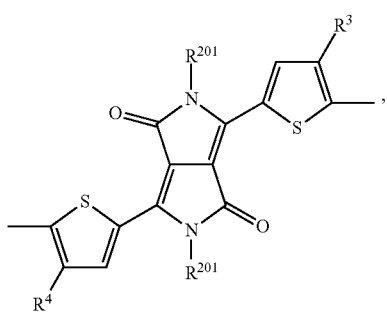
(XVu')

-continued (XVu")

(XVu''')

where
R³, R³', R⁴ and R⁴' are each independently hydrogen, or $C_1$-$C_{25}$ alkyl;
R⁸ and R⁸' are each independently hydrogen, or $C_1$-$C_{25}$ alkyl;
$R^{114}$ is a $C_1$-$C_{38}$ alkyl group;
$R^{201}$ is a $C_1$-$C_{38}$ alkyl group; and
$R^{202}$ and $R^{203}$ are each independently hydrogen or $C_1$-$C_{25}$ alkyl.

5. The polymer according to claim 3,
wherein
R¹ and R² are each independently of formula , or where
$R^{400}$, $R^{401}$, $R^{402}$, $R^{403}$, $R^{404}$ and $R^{405}$ are each independently H, CN, F, CF₃, $C_1$-$C_{18}$ alkoxy; $C_1$-$C_{18}$ alkyl; or $C_1$-$C_{18}$ alkyl which is interrupted by —O—, or
R¹ and R² together form a group

;

$R^{601}$ and $R^{602}$ are independently selected from the group consisting of a $C_1$-$C_{25}$alkyl group and hydrogen; and

*—[COM¹]—* is of formula
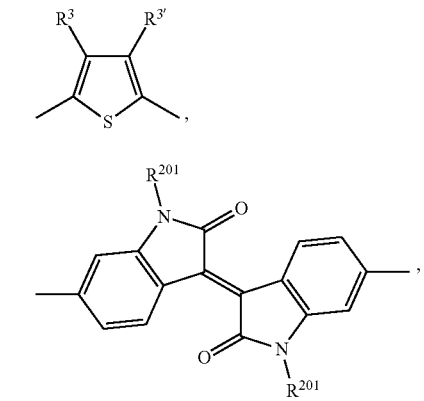
(XIa)
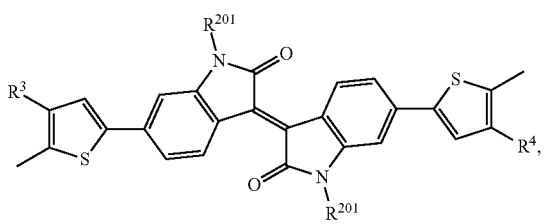
(XVb)
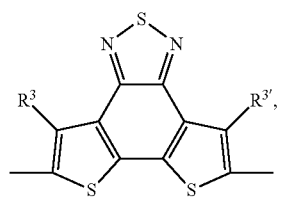
(XVb′)
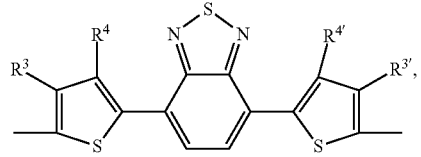
(XVe)
(XVh′)
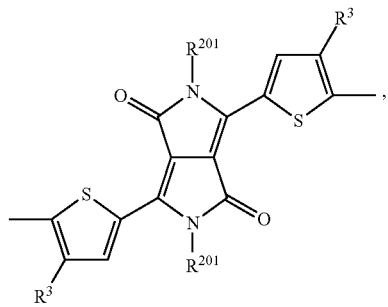
(XVu′)
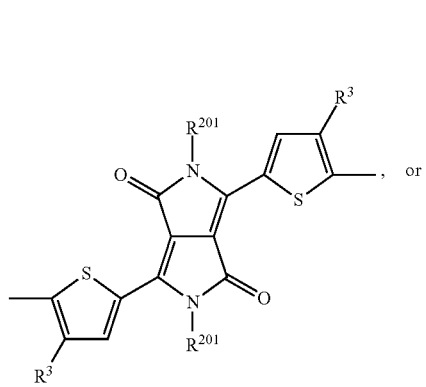
(XVu″) or
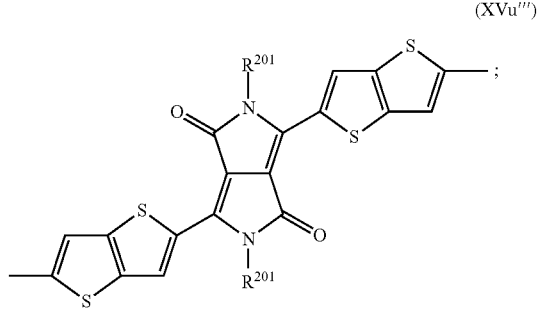
(XVu‴);
where $R^3$, $R^{3'}$, $R^4$ and $R^{4'}$ are each independently hydrogen or $C_1$-$C_{25}$ alkyl; and
$R^{201}$ is a $C_1$-$C_{38}$ alkyl group.
6. The polymer according to claim 4, which is a polymer of formula
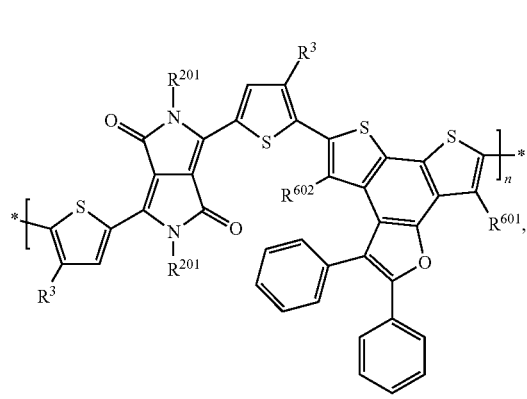
(Ia1)
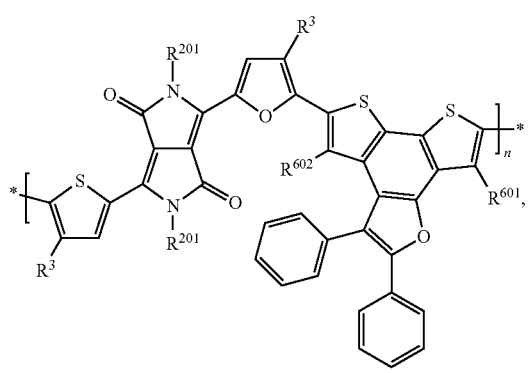
(Ia2)

-continued
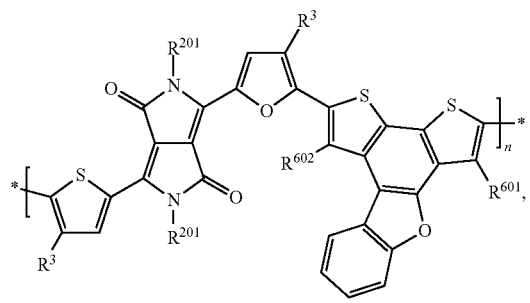
(Ia3)
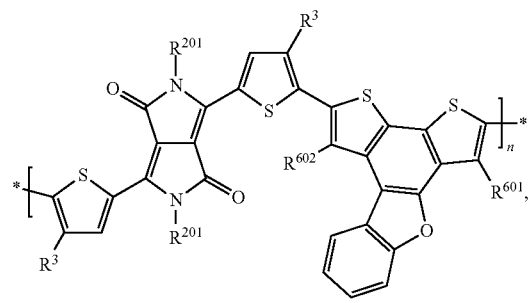
(Ia4)
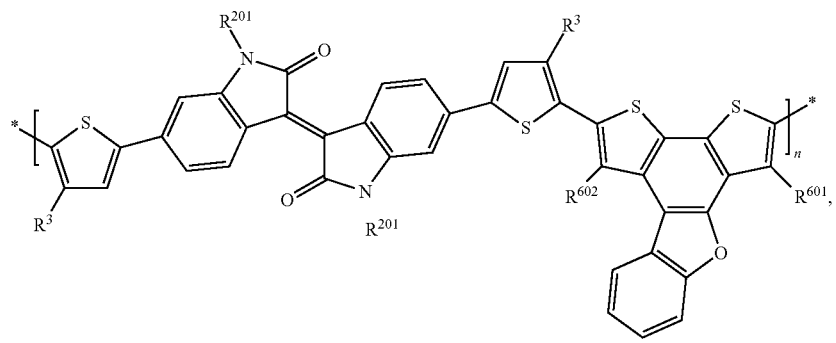
(Ia5)
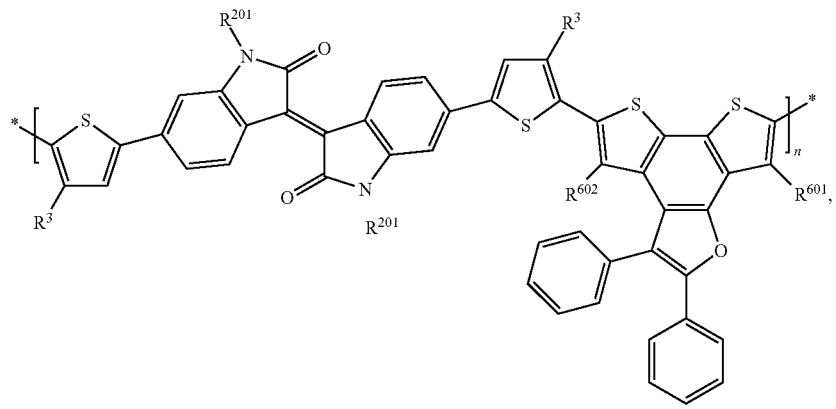
(Ia6)
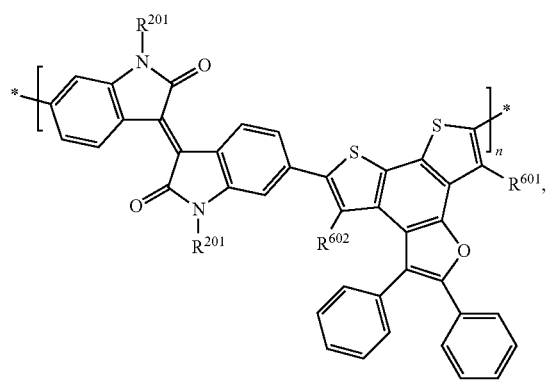
(Ia7)
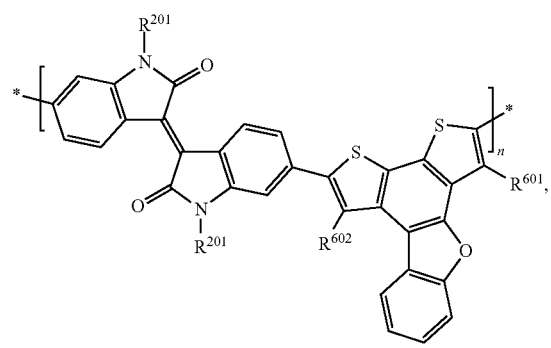
(Ia8)

-continued (Ia9)

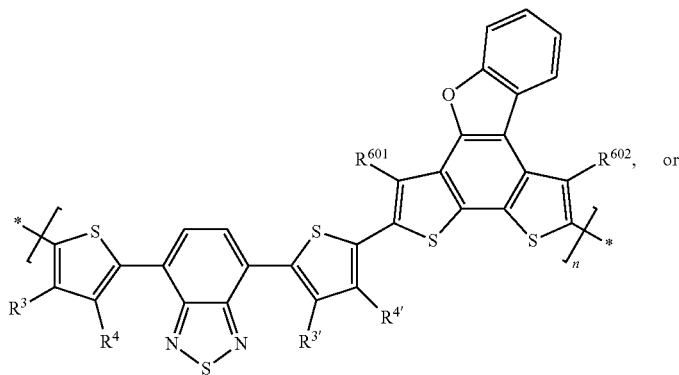

(Ia10)

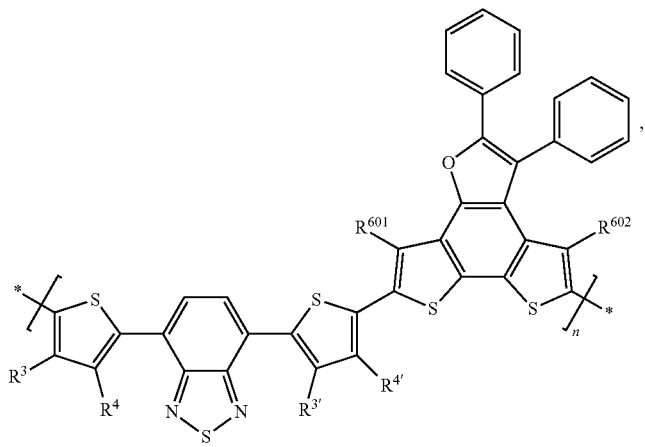

where
n is 4 to 1000;
$R^3$, $R^{3'}$, $R^4$ and $R^{4'}$ are each independently hydrogen or $C_1$-$C_{25}$ alkyl;
$R^{201}$ is a $C_1$-$C_{38}$ alkyl group, and
$R^{601}$ and $R^{602}$ are each independently hydrogen, or $C_1$-$C_{25}$ alkyl.

7. A compound of formula

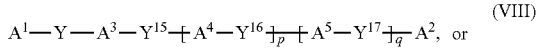 (VIII)

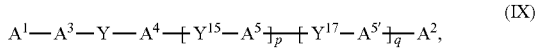 (IX)

where Y, $Y^{15}$, $Y^{16}$ and $Y^{17}$ are each independently of formula

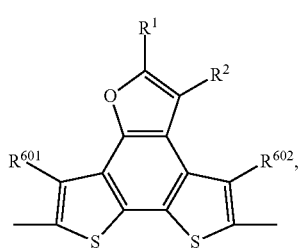 (I)

where $R^1$, $R^2$, $R^{601}$ and $R^{602}$ are as defined in claim 1;
p is 0, or 1, q is 0, or 1;
$A^1$ and $A^2$ are each independently of formula

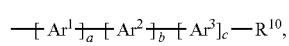

where
a is 0, 1, 2, or 3; b is 0, 1, 2, or 3; c is 0, 1, 2, or 3;
$A^3$, $A^4$, $A^5$ and $A^{5'}$ are each independently of formula

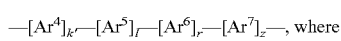, where k' is 0, 1, 2, or 3; l is 0, 1, 2, or 3; r is 0, 1, 2, or 3; z is 0, 1, 2, or 3;
$R^{10}$ is hydrogen, halogen, cyano, $C_1$-$C_{25}$ alkyl, $C_1$-$C_{25}$ alkyl which is substituted one or more times by E" and/or interrupted one or more times by D",

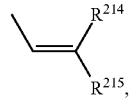

COO—$C_1$-$C_{18}$ alkyl, $C_4$-$C_{18}$ cycloalkyl group, $C_4$-$C_{18}$ cycloalkyl group, which is substituted by G", $C_2$-$C_{18}$ alkenyl, $C_2$-$C_{18}$ alkynyl, $C_1$-$C_{18}$ thioalkoxy, $C_1$-$C_{18}$ alkoxy, $C_1$-$C_{18}$ alkoxy which is substituted by E" and/or interrupted by D", $C_7$-$C_{25}$ aralkyl, $C_7$-$C_{25}$ aralkyl, which is substituted by G", or a group of formulae IVa to IVm,

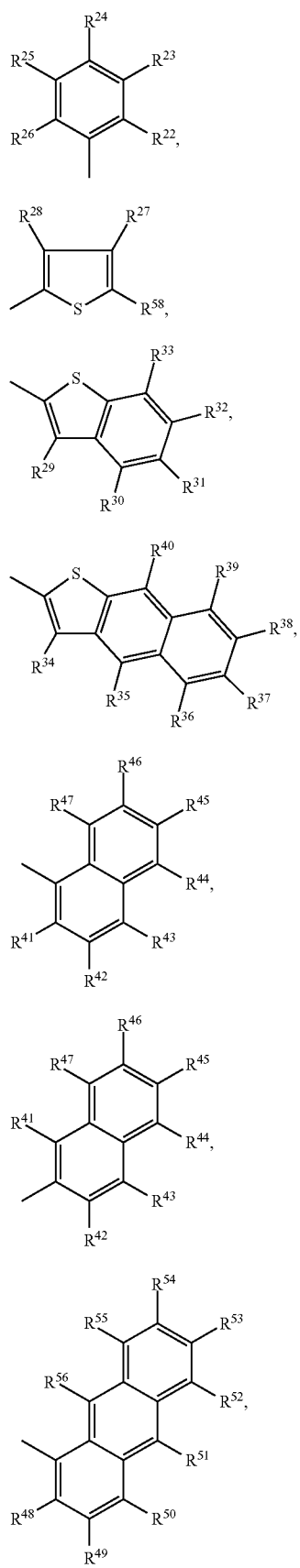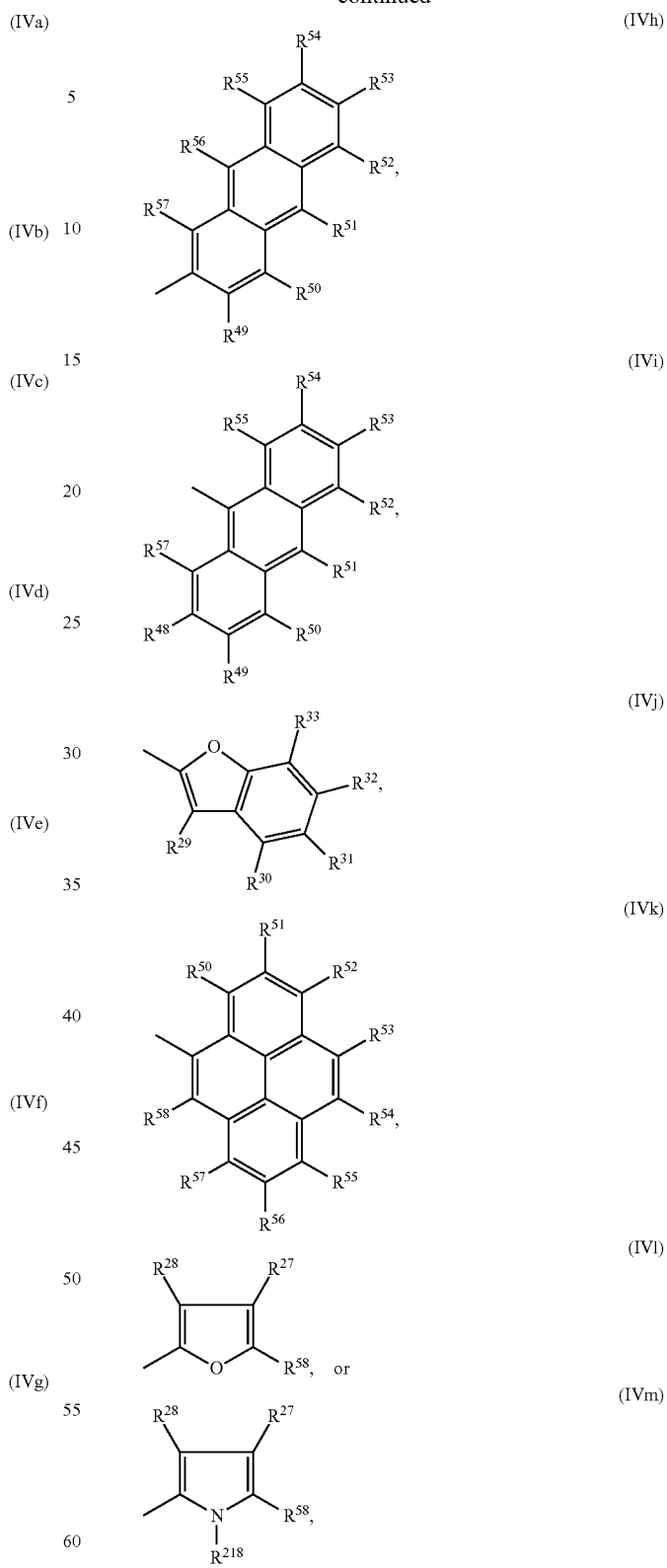
where $R^{22}$ to $R^{26}$ and $R^{29}$ to $R^{58}$ each independently represent H, halogen, cyano, $C_1$-$C_{25}$ alkyl, $C_1$-$C_{25}$ alkyl which is substituted by E" and/or interrupted by D", $C_6$-$C_{24}$ aryl, $C_6$-$C_{24}$ aryl which is substituted by G", $C_2$-$C_{20}$ heteroaryl, $C_2$-$C_{20}$ heteroaryl which is substituted by G", a $C_4$-$C_{18}$ cycloalkyl group, a $C_4$-$C_{18}$ cycloalkyl group, which is substituted by G", $C_2$-$C_{18}$ alkenyl, $C_2$-$C_{18}$ alkynyl, $C_1$-$C_{18}$ alkoxy, $C_1$-$C_{18}$ alkoxy which is substituted by E" and/or interrupted by D", $C_7$-$C_{25}$ aralkyl, or $C_7$-$C_{25}$ aralkyl, which is substituted by G", $R^{27}$ and $R^{28}$ are each independently hydrogen, $C_1$-$C_{25}$ alkyl, halogen, cyano or $C_7$-$C_{25}$ aralkyl, or $R^{27}$ and $R^{28}$ together represent alkylene or alkenylene which optionally are both bonded via oxygen and/or sulfur to the thienyl residue and which optionally both have up to 25 carbon atoms, $R^{59}$ is hydrogen, $C_6$-$C_{18}$ aryl; $C_6$-$C_{18}$ aryl which is substituted by $C_1$-$C_{18}$ alkyl, or $C_1$-$C_{18}$ alkoxy; or $C_1$-$C_{25}$ alkyl, which optionally is interrupted by one or more oxygen or sulphur atoms; or $C_7$-$C_{25}$ arylalkyl, D" is —CO—, —COO—, —S—, —O—, or $NR^{112''}$—, E" is $C_1$-$C_8$thioalkoxy, $C_1$-$C_8$ alkoxy, CN, —$NR^{112''}R^{113''}$, —$CONR^{112''}R^{113''}$, or halogen, G" is E", or $C_1$-$C_{18}$ alkyl, and $R^{112''}$ and $R^{113''}$ are each independently H; $C_6$-$C_{18}$ aryl; $C_6$-$C_{18}$ aryl which is substituted by $C_1$-$C_{18}$ alkyl, or $C_1$-$C_{18}$ alkoxy; $C_1$-$C_{18}$ alkyl; or $C_1$-$C_{18}$ alkyl which is interrupted by —O—;

$R^{214}$ and $R^{215}$ are each independently hydrogen, $C_1$-$C_{18}$ alkyl, $C_6$-$C_{24}$ aryl, $C_2$-$C_{20}$ heteroaryl, —CN or $COOR^{216}$; $R^{216}$ is $C_1$-$C_{25}$ alkyl, $C_1$-$C_{25}$ haloalkyl, $C_7$-$C_{25}$ arylalkyl, $C_6$-$C_{24}$ aryl or $C_2$-$C_{20}$ heteroaryl;

$R^{218}$ is hydrogen, $C_6$-$C_{18}$aryl; $C_6$-$C_{18}$aryl which is substituted by $C_1$-$C_{18}$ alkyl, or $C_1$-$C_{18}$ alkoxy; or $C_1$-$C_{25}$ alkyl, which optionally is interrupted by one or more oxygen or sulphur atoms; or $C_7$-$C_{25}$ arylalkyl, $Ar^1$, $Ar^2$, $Ar^3$ $Ar^4$, $Ar^5$, $Ar^6$ and $Ar^7$ are each independently of each other a group of formula (XIa), (XIb), (XIc), (XId), (XIe), (XIf), (XIg), (XIh), (XIi), (XIj), (XIk), (XIl), (XIm), (XIn), (XIo), (XIpa), (XIpb), (XIq), (XIr), (XIs), (XIt), (XIu), (XIv), (XIw), (XIx), (XIy), (XIz), (XIIa), (XIIb), (XIIc), (XIId), (XIIe), (XIIf), (XIIg), (XIIh), (XIIi), (XIIj), (XIIk), (XIII), (XIV), (XVa), (XVb), (XVc), (XVd), (XVe), (XVf), (XVg), (XVh), (XVi), (XVj), (XVk), (XVl), (XVm), (XVn), (XVo), (XVp), (XVq), (XVr), (XVs), (XVt), (XVuc), or (XVu).

8. The compound according to claim 7, which is a compound of formula $A^1$-Y-$A^3$-$Y^{15}$-$A^2$ (VIIIa), $A^1$-Y-$A^3$-$Y^{15}$-$A^4$-$Y^{16}$-$A^2$ (VIIIb), A-Y-$A^3$-$Y^{15}$-$A^4$-$Y^{16}$-$A^5$-$Y^{17}$-$A^2$ (VIIIc), $A^1$-$A^3$-Y-$A^4$-$A^2$ (IXa), $A^1$-$A^3$-Y-$A^4$-$Y^{15}$-$A^5$-$A^2$ (IXb), or $A^1$-$A^3$-Y-$A^4$-$Y^{15}$-$A^5$-$Y^{17}$-$A^{5'}$-$A^2$ (IXc), wherein where Y, $Y^{15}$, $Y^{16}$ and $Y^{17}$ are each independently of formula (I)

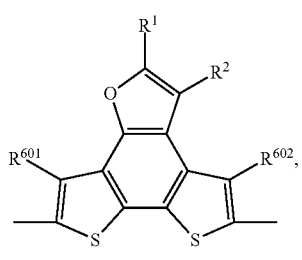

where $R^1$ and $R^2$ are each independently of formula

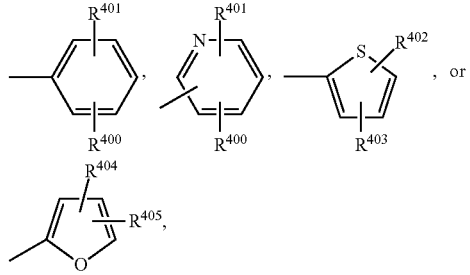

where $R^{400}$, $R^{401}$, $R^{402}$, $R^{403}$, $R^{404}$ and $R^{405}$ are each independently H, CN, F, $CF_3$, $C_1$-$C_{18}$ alkoxy; $C_1$-$C_{18}$ alkyl; or $C_1$-$C_{18}$ alkyl which is interrupted by —O—, or $R^1$ and $R^2$ together form a group

and $R^{601}$ and $R^{602}$ are each independently hydrogen, or $C_1$-$C_{25}$ alkyl, $A^3$, $A^4$, $A^5$ and $A^{5'}$ are each independently of formula

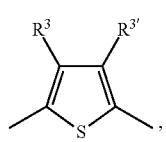

(XIa)

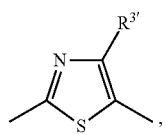

(XId)

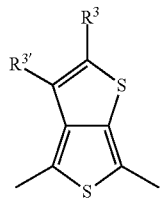

(XIh)

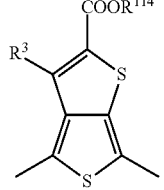

(XIi)

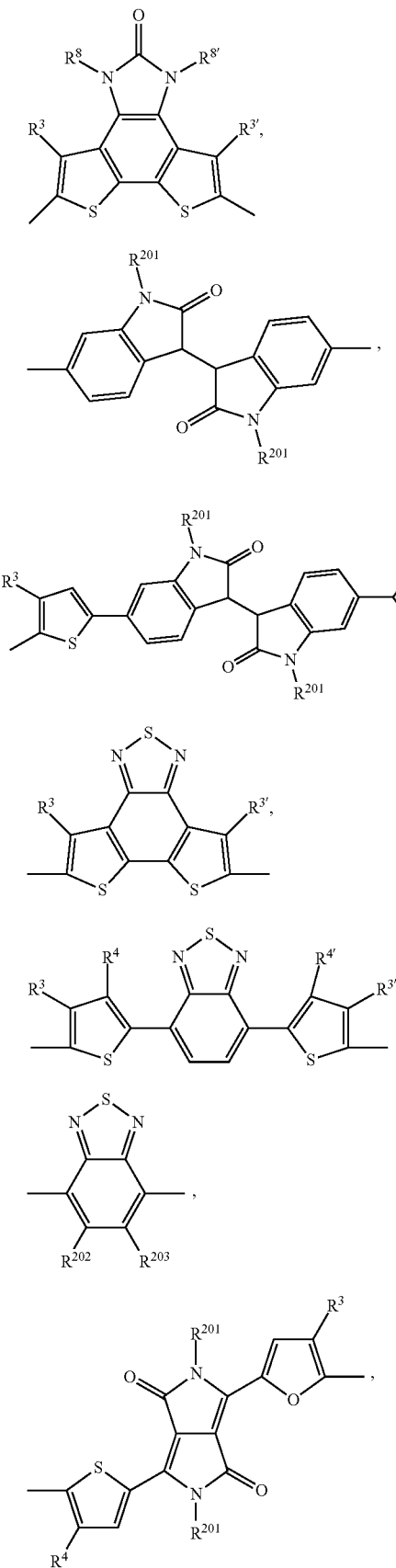

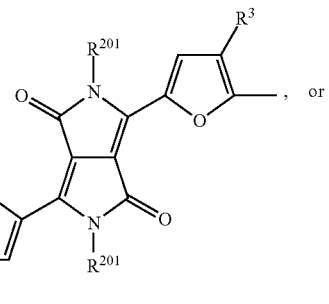

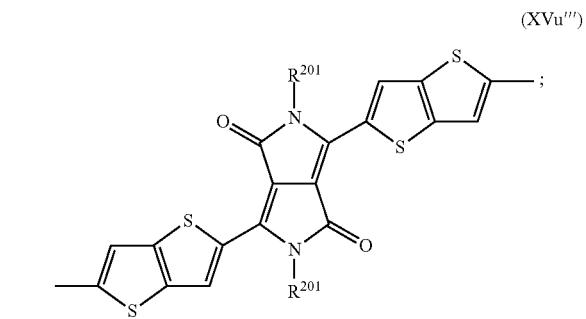

where
R³, R³', R⁴ and R⁴' are each independently hydrogen, or $C_1$-$C_{25}$ alkyl;
R⁸ and R⁸' are each independently hydrogen, or $C_1$-$C_{25}$ alkyl;
$R^{114}$ is a $C_1$-$C_{38}$ alkyl group;
$R^{201}$ is a $C_1$-$C_{38}$ alkyl group; and
$R^{202}$ and $R^{203}$ are each independently hydrogen or $C_1$-$C_{25}$ alkyl.

9. An organic semiconductor material, layer or component, comprising the polymer according to claim 1.

10. An electronic device, comprising the polymer according to claim 1.

11. The electronic device according to claim 10, which is an organic light emitting diode, an organic photovoltaic device, a photodiode, or an organic field effect transistor.

12. A process for preparing an electronic device, the process comprising:
applying a solution and/or dispersion of the polymer according to claim 1 in an organic solvent to a suitable substrate, and
removing the solvent.

13. A compound of formula $$X^2-A^{1'}-A^3-Y-A^4\!-\!\!\left[Y^{15}\!-\!A^5\right]_{\!p}\!\!-\!\!\left[Y^{17}\!-\!A^{5'}\right]_{\!q}\!\!-\!A^{2'}-X^{2'}, \text{ or} \quad (IV)$$

$$X^2-A^{1'}-Y-A^3-Y^{15}\!-\!\!\left[A^4\!-\!Y^{16}\right]_{\!p}\!\!-\!\!\left[A^5\!-\!Y^{17}\right]_{\!q}\!\!-\!A^{2'}-X^{2'}, \quad (V)$$

where
$A^{1'}$ and $A^{2'}$ are each independently of formula $$-\!\!\left[Ar^1\right]_{\!a}\!\!-\!\!\left[Ar^2\right]_{\!b}\!\!-\!\!\left[Ar^3\right]_{\!c}\!\!-\!,$$

where $X^2$ and $X^{2'}$ are each independently halogen, $ZnX^{12}$, $-SnR^{207}R^{208}R^{209}$, where $R^{207}$, $R^{208}$ and $R^{209}$ are each independently H or $C_1$-$C_6$ alkyl, wherein two radicals optionally form a common ring and these radicals are optionally branched or unbranched and $X^{12}$ is a halogen atom; or $-OS(O)_2CF_3$, $-OS(O)_2-$ aryl, $-OS(O)_2CH_3$, $-B(OH)_2$, $-B(OY^1)_2$,

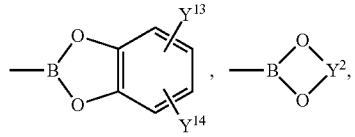

$-BF_4Na$, or $-BF_4K$, where $Y^1$ is independently in each occurrence a $C_1$-$C_{10}$ alkyl group and $Y^2$ is independently in each occurrence a $C_2$-$C_{10}$ alkylene group, and $Y^{13}$ and $Y^{14}$ are each independently hydrogen, or a $C_1$-$C_{10}$ alkyl group, and a, b, c, p, q, $Ar^1$, $Ar^2$, $Ar^3$, Y, $Y^{15}$, $Y^{16}$, $Y^{17}$, $A^3$, $A^4$, $A^5$ and $A^{5'}$ are as defined in claim 7.

14. A polymer, comprising a repeating unit of formula

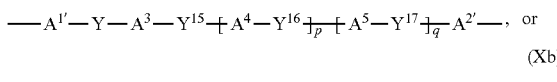

where $A^{1'}$ and $A^{2'}$ are each independently of formula

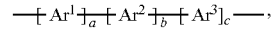

where a, b, c, p, q, $Ar^1$, $Ar^2$, $Ar^3$, Y, $Y^{15}$, $Y^{16}$, $Y^{17}$, $A^3$, $A^4$, $A^5$ and $A^{5'}$ are as defined in claim 7.

* * * * *